US006221582B1

(12) United States Patent
Giesendorf et al.

(10) Patent No.: US 6,221,582 B1
(45) Date of Patent: Apr. 24, 2001

(54) POLYNUCLEIC ACID SEQUENCES FOR USE IN THE DETECTION AND DIFFERENTIATION OF PROKARYOTIC ORGANISMS

(75) Inventors: Belinda Giesendorf, Nijmegen; Wilhelmus Quint, Nootdorp; Leendert-Jan Van Doorn, Ridderkerk, all of (NL)

(73) Assignees: Innogenetics N.V., Ghent (BE); Delft Diagnostic Laboratory B.V., Delft (NL)

( * ) Notice: Subject to any disclaimer, the term of this patent is extended or adjusted under 35 U.S.C. 154(b) by 0 days.

(21) Appl. No.: 08/836,261
(22) PCT Filed: Oct. 30, 1995
(86) PCT No.: PCT/EP95/04264
§ 371 Date: Aug. 7, 1997
§ 102(e) Date: Aug. 7, 1997
(87) PCT Pub. No.: WO96/13608
PCT Pub. Date: May 9, 1996

(30) Foreign Application Priority Data

Oct. 28, 1994 (EP) .................................................. 94870171

(51) Int. Cl.[7] .............................. C12Q 1/68; C07H 21/02
(52) U.S. Cl. ............................................... 435/6; 536/22.1
(58) Field of Search ........................ 435/6, 91.2; 536/22.1

(56) References Cited

FOREIGN PATENT DOCUMENTS

| WO91/12343 | 8/1991 | (WO) . |
| WO92/01055 | 1/1992 | (WO) . |
| WO92/03051 | 3/1992 | (WO) . |
| WO93/03759 | 3/1993 | (WO) . |
| WO93/12230 | 6/1993 | (WO) . |
| WO93/17341 | 9/1993 | (WO) . |
| WO94/03612 | 2/1994 | (WO) . |
| WO95/07362 | 3/1995 | (WO) . |

OTHER PUBLICATIONS

Jaswinder Grewal et al., "Effect of Mutational Alteration of Asn–128 in the Putative GTP–Binding Domain of Tetracycline Resistance Determinant Tet(O) from *Campylobacter jejuni*," *Antimicrobial Agents and Chemotherapy*, vol. 37, No. 12, pp. 2645–2649, Dec. 1993.

Mark Eyers et al., "Discrimination Among Thermophilic Campylobacter Species by Polymerase Chain Reaction Amplification of 23S rRNA Gene Fragments," *Journal of Clinical Microbiology*, vol. 31, No. 12, pp. 3340–3343, Dec. 1993.

Belinda A. J. Giesendorf et al., "Development of Species–Specific DNA Probes for *Campylobacter jejuni*, *Campylobacter coli*, and *Campylobacter lari* by Polymerase Chain Reaction Fingerprinting," *Journal of Clinical Microbiology*, vol. 31, No. 6, pp. 1541–1546, Jun. 1993.

Thomas E. Dever et al., "GTP–Binding Domain: Three Consensus Sequence Elements with Distinct Spacing," *Proc. Natl. Acad. Sci. USA*, vol. 84, pp. 1814–1818, Apr. 1987.

*Primary Examiner*—Eggerton A. Campbell
(74) *Attorney, Agent, or Firm*—Howrey Simon Arnold & White, LLP

(57) ABSTRACT

The invention relates to the use of the GTPase gene family as a target for nucleic acid based assays for the detection and differentiation of prokaryotic organisms. The invention relates to polynucleic acids derived from gene sequences encoding prokaryotic GTPase (=GTP-binding) proteins, as well as their use in the detection and identification of prokaryotic organisms; primers and probes derived from said polynucleic acid sequences, for specific amplification and detection of prokaryotic DNA in a biological sample; as well as methods and kits allowing the detection and identification of at least one micoroorganism, and preferentially several microorganisms simultaneously in a sample. More specifically, the invention relates to new polynucleic acid sequences encoding GTPase proteins from Campylobacter species, primers and probes derived from them, and methods and kits comprising these reagents for the detection and differentiation of species belonging to the genus Campylobacter.

19 Claims, 34 Drawing Sheets

FIG. 2A

Figure 1:
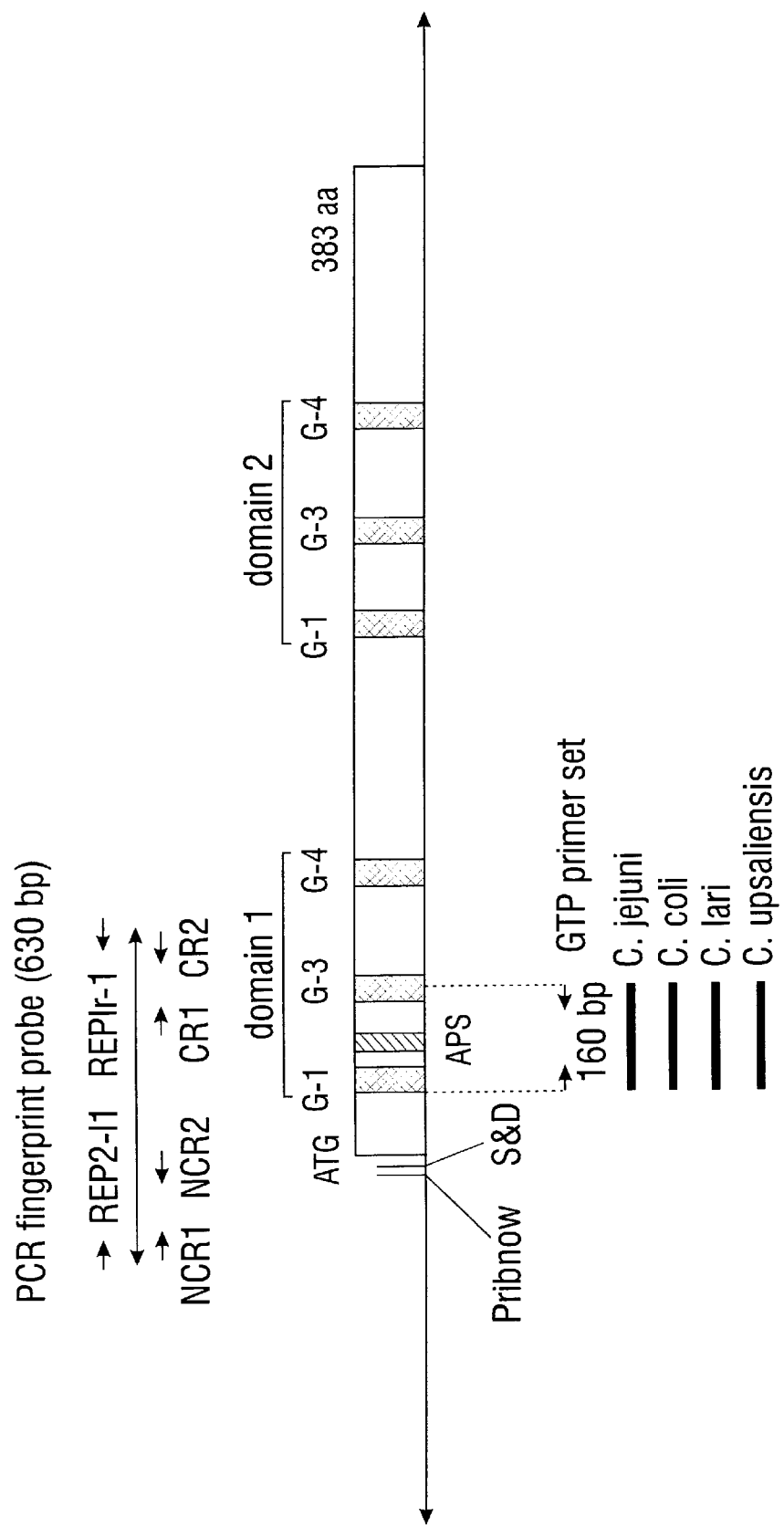

```
         10         20         30         40         50         60
         |          |          |          |          |          |
GATATCAAGCTTTAGTGACATGAATTTGATAAATGGTGCCTAAAGTTCCCATAATGGCAA 70         80         90        100        110        120
         |          |          |          |          |          |
TGATAAGCCAAGCTGTAAGACTTGGCATCACAAAAGGTGCTAGAATGAAATCTAAATGTA 130        140        150        160        170        180
         |          |          |          |          |          |
AAGAATCAAGATGCTGTGGTTCAAAAAATTCAGCACTGATCATAGAAATTAAAGGCATTA 190        200        210        220        230        240
         |          |          |          |          |          |
AGGTTCCTAAAAGGATAAAAGAAAAGGCAATTTGTTCTGTAGTGTAAGATTTTCTAAGTT 250        260        270        280        290        300
         |          |          |          |          |          |
CTCTTACACTTGTAAGAGCTAAGCAGCTAAAAAATCCACTGTGATACCTATAACTGAATT
```

```
         310       320       330       340       350       360
          |         |         |         |         |         |
TTTTAAAATCAAAGCCTGAATGATTTAAATTAATGAGCCCAAGGCTGAGCAATTAAAAGCA 370       380       390       400       410       420
          |         |         |         |         |         |
CTCCACCAAATGCTATTAAAATTCCTACTCCAGCCTTTGATGCCAATATTTCTTTAAAA 430       440       450       460       470       480
          |         |         |         |         |         |
ACAACAAAAGCTATTAAAGTAATAAAAATAGGAGCAGTTTTTTGAAAAGCAAAAGCTCCG 630 bp
         490       500       510       520 ┌──▶ 530       540
          |         |         |         |         |         |
CCTAGTGTAATATTTGAAACATTATAGAAAAACATATATAGTGAAAGGCGTGCCTACTACT
```

FIG. 2B

FIG. 2C

```
        550       560       570       580       590       600
         |         |         |         |         |         |
CCACGAAATACCAAGAGCCAAAAATGTCCCCCTTCTTTATGTGCCTTAGATCGTTTTAAA 610       620       630       640       650       660
         |         |         |         |         |         |
AGATAGACTATGAAAAAAAATTCCTATGATATTTCTAAAAACATAATTTCTATAGAACTCA 670       680       690       700       710       720
         |         |         |         |         |         |
TTTCCTTGCTAAGAATTTTTCCACAAGCNCCCATAAGTGCAAAATCCAAACATGCTAAAA 730       740       750       760       770       780
         |         |         |         |         |         |
TCATGAAATAAATTCCTAAATTATGCTTGATTACTTTTAGCATTTTTTTCCTTGACTAA 790       800       810       820       830       840
         |         |         |         |         |         |
AATCTGTGTTAATTCTAGTCTTTTTTTGCTTAATATTAAGCCAAATTTTATATAATTTA
```

FIG. 2D

```
850        860        870        880        890    G-1  900
AAAATATAATTTTCTAGGAAAAAAAATGCAAAGAATCATACTTATAGG|CAAGCCAAATGT
                                    METGlnSerIleIleLeuIleGl|yLysProAsnVal 910        920        930        940        950        960
GGAAAA|TCAAGTCTTTTAATAGAATGGCAAGGCAAAGAATAGCTATTACAAGTGATATT
GlyLysSerSerLeuPheAsnArgMETAlaArgGlnArgIleAlaIleThrSerAspIle 970        980        990       1000       1010       1020
TCAGGTACAACTAGAGATACAAATAAAACGCAAATTCATATTCATTCAAAAAAAGCCATG
SerGlyThrThrArgAspThrAsnLysThrGlnIleHisIleHisSerLysLysAlaMET

1030   G-3  1040       1050       1060       1070       1080
CTTATT|GATAGTGGAGGG|CTTGATGAAAGTGATGAACTTTTTAAAAATGTGAAAAAAAAC
LeuIle|AspSerGlyGly|LeuAspGluSerAspGluLeuPheLysAsnValLysLysAsn 1090       1100       1110       1120       1130       1140
ACTTTAAAAAGTAGCTAAAGAAAAGGCGATATCATACTTTATCTAGTTGATGGGAAATTAGCG
ThrLeuLysValAlaLysGluSerAspIleIleLeuTyrLeuValAspGlyLysLeuAla
```

DOMAIN 1

FIG. 2E

```
630 bp
         1150       1160       1170       1180       1190       1200
          |          |          |          |          |          |
CCTGATGATGAGGATAGACAGTTTTTTATTCTTTAAAAAACTTGGAAAACCTATAGCC
ProAspAspGluAspArgGlnPhePheTyrSerLeuLysLysLeuGlyLysProIleAla 1210       1220       1230       1240       1250       1260
          |          |          |          |          |          |
TTAGTGGTTAATAAAGTAGATAATAAAAAAGATGAAGAAAGGGCTTGGGAGTTTGCAAAT
         G-4    LeuValValAsnLysValAspAsnLysLysAspGluGluArgAlaTrpGluPheAlaAsn 1270       1280       1290       1300       1310       1320
          |          |          |          |          |          |
TTTGGAGTAAAGGAAATCTTCAATCTTTCAGTAACCCATAATGTAGGCTTAGATGAACTT
PheGlyValLysGluIlePheAsnLeuSerValThrHisAsnValGlyLeuAspGluLeu 1330       1340       1350       1360       1370       1380
          |          |          |          |          |          |
TATGAATGGCTTGAAAAATTTTACATGAAGAGTTTTTAATCCCTGATGAAGAAGAAAAT
TyrGluTrpLeuGluLysPheTyrMetLysSerPheLeuIleProAspGluGluGluAsn 1390       1400       1410       1420       1430       1440
          |          |          |          |          |          |
TTAGAAGATTTTTTAGAGCATTATGAAGAAGGGAAAAGAATTCAATTTAAAGAAGTCGAT
LeuGluAspPheLeuGluHisTyrGluGluGlyLysGluPheGlnPheLysGluValAsp
```

```
      1450           1460           1470          1480           1490           1500
       |              |              |             |              |              |
CAAAATCATATCAGAGTGGGTATTGTA GGGCGTGTAAATGTTGGAAAATCAAGTCTTTA
GlnAsnHisIleArgValGlyIleVal GlyArgValAsnValGlyLysSerSerLeuLeu
                              G-1

1510           1520           1530          1540           1550           1560
       |              |              |             |              |              |
AATGCTTTGGTTAAACAAGAACGCAGTGTTGTAAGTTCTATCGCAGGAACTACTATAGAT
AsnAlaLeuValLysGlnGluArgSerValValSerSerIleAlaGlyThrThrIleAsp 1570           1580           1590          1600           1610           1620
       |              |              |             |              |              |                G-3
CCTGTTAATGAAAGTGTAGTTCATAAAGATAAAGTGATAGAATTTGT GATACTGCAGGT
ProValAsnGluSerValValHisLysAspLysValIleGluPheVal AspThrAlaGly 1630           1640           1650          1660           1670           1680
       |              |              |             |              |              |
ATTAGAAAAAGGGGTAAAATTCAAGGACTCGAACGCTTTGCCCTAAATCGCACGGAAAAA
IleArgLysArgGlyLysIleGlnGlyLeuGluArgPheAlaLeuAsnArgThrGluLys 1690           1700           1710          1720           1730           1740
       |              |              |             |              |              |
ATTTATCTCATTCTCAAATAGCACTTTTGGTTTTAGATGGCGCATGAGGGCTTTAACGAA
IleLeuSerHisSerGlnIleAlaLeuLeuValLeuAspAlaHisGluGlyPheAsnGlu
```

DOMAIN 2

FIG. 2F

```
         1750         1760         1770         1780         1790         1800
          |            |            |            |            |            |
CTTGATGAACGCATTGCTGGGCTTGTGGCTAAGCATTATTTGGGTGTGATTATTGTTTA
LeuAspGluArgIleAlaGlyLeuValAlaLysHisTyrLeuGlyValIleIleValLeu 1810         1820         1830         1840         1850         1860
          |            |            |            |            |            |
AATAAATGGGATAAAAGTGAGATGGATTTTGATAAAACTGTAAAAGAATTGCATCTTGAT
AsnLysTyrAspLysSerGluMETAspPheAspLysThrValLysGluLeuHisLeuAsp
G-4

1870         1880         1890         1900         1910         1920
          |            |            |            |            |            |
CGTTTTAAATTCTAGCTTACGCACCTGTGATTAGCGTATCGGCTTAAGTGGAAAAAGG
ArgPheLysPheLeuAlaTyrAlaProValIleSerValSerAlaLeuSerGlyLysArg 1930         1940         1950         1960         1970         1980
          |            |            |            |            |            |
GTGCATGTTTTACTCGATAAAATTTGCAAATTTTGAGAATTTCACTCAAAAAATCCAA
ValHisValLeuLeuAspLysIleLeuGlnIlePheGluAsnPheThrGlnLysIleGln 1990         2000         2010         2020         2030         2040
          |            |            |            |            |            |
ACTTCTAAGCTTATGAAAATTTCTTCATACTTAAATTTAGGGGTGAATTACATTTTAC
ThrSerLysLeuMETLysIleSerPheIleLeu---

CAGGAGC
```

FIG. 2G

LANES 1-36

LANES 37-72

LANES 1-36

LANE 36

LANES 37-72 lanes 42-47

LANES 1-36

LANES 37-72

LANES 1-36

LANES 37-72

LANES 1-36

LANES 37-72

LANES 1-36

LANES 37-72

```
rinvshort       CCAAATGTTGGAAAAATCAAGTCTTTTTAATAGAATGGCAAGACAAAGAATAGCTATTACAAGTGATATTT
1. (892-1044)

3.  CAMJEJLI04    ------------------C----------------------------------------------------
4.  CAMJEJLI030   -----------------------------------------------------------------------
4.  CAMJEJLI061   -----------------------------------------------------------------------
4.  CAMJEJLI038   -----------------------------------------------------------------------
5.  CAMJEJLI036   ------------------C----------------------------------------------------
6.  CAMJEJLI039   -----------------------------------------------------------------------
7.  CAMJEJLI049   ------------------C----------------------------------------------------
8.  CAMJEJLI023   -----------------------------------------------------------------------
9.  CAMJEJLI028   ------------------C----------------------------------------------------
10. CAMJEJLI07    -----------------------------------------------------------------------
11. CAMCOLLI08    ----T-A------C-------------------G-------------------------------A---N
12. CAMCOLLI029   ----T-A------C-------------------G-------------------------------A----
12. CAMCOLLI078   ----T-A------C-------------------G-------------------------------A----
13. CAMCOLLI021   ----T-A------C-------------------G-------------------------------A----
13. CAMCOLLI024   ----T-A------C-------------------G-------------------------------A----
14. CAMCOLLI080   ----T-A------C----------C--------G-------------------------------A----
15. CAMCOLLI047   ----T-A------C-------------------G-------------------------------A----
```

FIG. 8A

```
rinvshort
         CAGGTACAACTAGAGATACAAATAAAACGCAAATTCATATTCATTCAAAAAAAGCCATGCTTATTGATAGTGGAGGGCTTGAT 3.CAMJEJLI04    ------C------- ---------------- ------------------------- -----------------------
4.CAMJEJLI030   -------------- ---------------- ------------------------- -----------------------
4.CAMJEJLI061   -------------- ---------------- ------------------------- -----------------------
4.CAMJEJLI038   -------------- ---------------- ------------------------- -----------------------
5.CAMJEJLI036   N------------- ---------------- ------------------------- -----------------------
6.CAMJEJLI039   -------------- ---------------- ------------------------- -----------------------
7.CAMJEJLI049   ------C------- -----------AG--- ------------------------- -----------------------
8.CAMJEJLI023   ------C------- -----------AG--- -----------------A------- -----------------------
9.CAMJEJLI028   -------------- -----------AG--- ------------------------- -----------------------
10.CAMJEJLI07   N------------- --------AG--G--- ------------------------- -----------------------
11.CAMCOLLI08   N----------N-- --------AG--G--- ---------------------C--- -----------------------
12.CAMCOLLI029  ----T--A------ --------AG--G--- ----TT----AA---T--------- -------C--AT--G-------
12.CAMCOLLI078  ----T--A------ --------AG--G--- ----TT----AA---T--------- -------C--AT--G-------
13.CAMCOLLI021  ----T--A------ --------AG--G--- ----TT----AA---T--------- -------C--AT--G-------
13.CAMCOLLI024  ----T--A------ --------AG--G--- ----TT----AA------G------ -------C--AT--G-------
14.CAMCOLLI080  ----T--A------ --------AG--G--- ----TT----AA------G------ -------C--AT--G----C--
15.CAMCOLLI047  ----T--A------ --------AG--G--- ----TT----AA---T--------- -------C--AT--G-------
```

FIG. 8B

| | | | | | | | | | |
|---|---|---|---|---|---|---|---|---|---|
| 16.CAMCOLLI012 | ---TNN- | ------C- | -------- | -------- | ----G--- | -------- | -------- | ----A--- | ---N |
| 17.CAMLARLI031 | -------- | -------- | ---C-T-- | -------- | -A-GC-C- | -------- | ----N--- | ----C--- | --NN |
| 18.CAMLARLI035 | -------- | -------- | ---C-T-- | -------- | -A-GC-C- | -------- | ----N--- | ----C--- | --AA |
| 19.CAMLARLI073 | -------- | -------- | ---C-T-- | -------- | -A-GC-C- | -------- | ----C--- | ----C--- | --AA |
| 20.CAMLARLI064 | -------- | -------- | ---C-T-- | -------- | -A-GC-C- | -------- | ----C--- | ----C--- | --AA |
| 21.CAMLARLI056 | -------- | -------- | -------- | -------- | -A-GC-C- | -------- | ----N--- | ----C--- | --AA |
| 22.CAMUPS37_5 | -C------ | ---C-C-A | -------G | -------- | -------- | ----C--- | ----C--- | ----A--- | ---- |
| 22.CAMUPS38_4 | -C------ | ---C-C-A | -------G | -------- | -------- | ----C--- | ----C--- | ----A--- | ---- |
| 22.CAMUPS39_3 | -C------ | ---C-C-A | -------G | -------- | -------- | ----C--- | ----C--- | ----A--- | ---- |
| 22.CAMUPS40_4 | -C------ | ---C-C-A | -------G | -------- | -------- | ----C--- | ----C--- | ----A--- | ---- |
| 23.CAMUPS41_4 | -------- | ---AC-C- | -A------ | -------- | -------- | ----C--- | ----C--- | ----A--- | ---- |
| 82.CJGTP2_13 | ------A- | --GCTT-- | -TT-A--- | -GA-CGCAG | -G--GT-- | --TC---- | -CG | | |

FIG. 8C

```
16.CAMCOLLI012    N-------T--A--------------N-------AG---G-
17.CAMLARLI031    GT---A--N--A--------------N-------TAG--G--
18.CAMLARLI035    GT---A--N--A--------------N-------TAG--G-A
19.CAMLARLI073    GT---A--C--A--------------C-------TAG--G-A--A---G--GGC----------T-------A
20.CAMLARLI064    GT---A--C--A--------------C-------TAG--G-A--A---S--GGC----------T-------A
21.CAMLARLI056    GT---A--N--A--------------N-------TAG--G-
22.CAMUPS37_5     ----C--G----------------------------TAA--G--A----CA--GGT---G-------T------C
22.CAMUPS38_4     ----C--G----------------------------TAA--G--A----CA--GGT---G-------T------C
22.CAMUPS39_3     ----C--G----------------------------TAA--G--A----CA--GGT---G-------T------C
22.CAMUPS40_4     ----C--G----------------------------TAA--G--A----CA--GGT---G-------T------C
23.CAMUPS41_4     ----C--G----------------------------TAA--G--A----CA--GGT---G-------T------

82.CJGTP2_13      ----A--T-----C-TGT---TGAAAGTG-AGT-CA-A-AGAT---GTGATAGAAT--G--
```

FIG. 8D

FIG. 10

```
                                                                              domain 1
                                                                          ←─────────────

G-1
1. MQS------------------------IILIGKPNVGKSSLFNRMARQRIA              27
2. MA-----------------------TPVVALVGRPNVGKSTLFNRLTRTRDA             29
3. MSQDGTWSDESDWELDDSDLAEFGPVVAVGRPNVGKSTLVNRILGRREA                 50
   *                       .   .******.*.**.*  *  *

G-3
1. ITSDISGTTRDDTNKTQIHIHSKKAMLIDSGGLDESDELFKN-VKKNTLKV              76
2. LVADFPGLTRDRKYGHAHIAGYDFIVIDTGGIDGTEEGVEEKMAEQSLLA               79
3. VVQDVPGVTRDRVSYDAMWTGRRFVVQDTGGWEPDAKGLKRLVAEQASVA              100
   .  *  * .*** .          . *.**     .     .*  ..

G-4
1. AKESDIILYLVDGKLAPDDEDRQFFYSLK-KLGKPIALVVNKVDNKKDEE              125
2. IDEADIVLFLVDARAGLTAADIGIANYLRQRQNKITVVVANKTDGIDADS              129
3. MRTADAVILVVDGVGVGATDADEAAAARIL-LRSGKLVFLAANKVDGEKGES            149
     .   * *  .                      .   ** *  .
```

FIG. 11A

```
1. RAWEFANFGVKEIFNLSVTHNVGLDELYEWLEKFLHEEFLIPDE-----E       170
2. HCAEFYQLGLGEIEQIAASQGRGVTQLMEQVLAPFAEKMENADENDRTSE        179
3. DASALWSLGLGEPHAISAMHGRGVADLLDKVLAALPNVAEST-------         191
   .    *          . *     .             *
```

```
                                       G-1
1. ENLEDFLEHYE----------EGKEFQFKEVDQNHIRVGIVGRVNVGKS        209
2. EEQDEWEQEFDFDSEEDTALIDDALEEEQDKNIKIAIVGRPNVGKS            229
3. ---------------------SLDGGLR------RVALVGKPNVGKS          211
   .  .  . .  .             *.       **.* *****
```

→ domain 2 →

```
                           G-3
1. SLLNALVKQERSVVSSIAGTTIDPVNESVVHKDKVIEFVDTAGIRKRGKI        259
2. TLTNRILGEDRVVVFDMPGTTRDSIYIPMERDGQQYTLIDTAGVRKRGKV        279
3. SLLNKLAGDQRSVVHEAAGTTVDPVDSLIEMGGRVWRFVDTAGLRRKVGQ        261
   .* **   .* **    * ***  *       *    ****  .
```

```
1. Q-GLERFALNRTEKILSHSQIALLVLDAHEGFNELDERIAGLVAKHYLGV        308
2. HLAVEKFSVIKTLQAIQDANVVLLTIDARENISDQDLSLLGFILNAGRSL        329
3. ASGHEFYASVRTHGAIDSAEVVIMLIDASEPLTGQDQRVLSMVIDAGRAL        311
    *  **      .         *.*  *         . .  * *
```

FIG. 11B

```
         G-4
1. IIVLNKWDKSEMDFDKTVKELHLDRFKFLAYAPVISVSALSGKRVHVLLD   358
2. VIVVNKWDGLDQDVKDRVKSELDRRLDFIDFARVHFISALHGSGVGNLFD   379
3. VLAFNKWDLVDEDRCDLLEREIDRELVQVRWAQRVNISAKTGRAVQKLVP   361
        ****       *        .   **   * * *       *

1. KILQIFENFTQKIQTSKLMKI-----------------------------   379
2. SIKEAYACATQKMTTSLLTRILQMATDEHQPPMIGGRRIKLKYAHPGGYN   429
3. AMENSLASWDTRIATGPLNIWIKAVVAATPPPVRGGKQPRILFATQATAR   411
        *.    .   .   :    *

1. --SFIL--------------------------------------------   383
2. PPIIVVHGNQMDKLPDSYKRYLSNYYRKSLKIIGSPIRLLFQEGSNPFAG   479
3. PPTFVLFTTGF--LEACYRRFLERRLRETFGFEGSPIRI-----------   448

1. -------------------   383
2. RKNKLTPNQLRKRKRLMKFIKKAKR   504
3. ------NVRVREKRGLKR-----R   461
```

FIG. 11C

| Seq. id. no | | | |
|---|---|---|---|
| 83. | CFETUS17_B | AACGACTTTTAATGCGTTAACAAAAGCTAGCAATGCAGAATCTGCAAACT | 50 |
| 83. | CFETUS_16 | AACGACTTTTAATGCGTTAACAAAAGCTAGCAATGCAGAATCTGCAAACT | 50 |
| 83. | CFETUS_18_B | AACGACTTTTAATGCGTTAACAAAAGCTAGCAATGCAGAATCTGCAAACT | 50 |
| 85. | CRECT7_13 | AACCACATTTAACGCGCTAACGAAGGGCAAAACGCCGAGAGCGCGAACT | 50 |
| 87. | CHYOI14_13 | AACGACTTTTAATGCTCTAACAAAAGCTAGTAACGCAGAGAGGCNGCAAACT | 50 |
| 89. | ACIN2627 | TACCCTTTTCAATGCATTAACGAAAGCAGGATTGCAG---CGGAAAACT | 47 |
| 89. | ACIN2284 | TACCCTTTTCAATGCATTAACGAAAGCAGGATTGCAG---CGGAAAACT | 47 |
| 91. | ACIN468 | TACCCTTTTCAATGCATTAACGAAAGCAGCAGGATTGCAG---CGGAAAACT | 47 |
| 93. | ACIN1163 | TACCCTTTTCAATGCATTAACGAAAGCAGCAGGATTGCAG---CGGAAAACT | 47 |
| 95. | ACIN45 | TACACTTTTCAATGCCTTAACCAAAGCTGCTATTGCTG---CAGAAAACT | 47 |
| 95. | ACIN548 | TACACTTTTCAATGCCTTAACCAAAGCTGCTATTGCTG---CAGAAAACT | 47 |
| | HI0393NUSH | TACTCTTTTAACGCACTCACTAAAGCTGGCATTGAAG---CCGCAAACT | 47 |
| | ECPTHGSH | TACCCTGTTCAACGCGCTGACCAAAGCCGGTATTGAAG---CGGCCAACT | 47 |
| | |  .  ** * ** *  .** * * **** | |

FIG. 16A

| | | | |
|---|---|---|---|
| 83. | CFETUS17_B | ATCCATTTTGCACTATAGAGCCAAATAAAAGCCATAGTTCCGGXTCCAGAT | 100 |
| 83. | CFETUS_16 | ATYYATYTTGCACTATAGAGCCAAATAAAAGCCATAGTTCCGGTTCCAGAT | 100 |
| 83. | CFETUS18_B | ATCCATTTTGCACTATAGAGCCAAATAAAAGCCATAGTTCCGGTTCCAGAT | 100 |
| 85. | CRECT7_13 | ATCCGTTYTGCACGATCGAGCCRAATAAAGCCGTCGTGCCGGTGCCCGAT | 100 |
| 87. | CHYOI14_13 | ATCNGTTTTGTACTATNGAGCCAAATAAAGCTATAGTTNNTGTTNNTGAT | 100 |
| 89. | ACIN2627 | TCCCTTTCTGTACCATTGAACCAAACACAGGTATTGTTCCTGTACCAGAT | 97 |
| 91. | ACIN468 | TCCCTTTCTGTACCATTGAACCAAACACAGGTATTGTTCCTGTACCAGAT | 97 |
| 93. | ACIN1163 | TCCCTTTCTGTACCATTGAACCAAACACAGGTATTGTTCCTGTACCAGAT | 97 |
| 95. | ACIN45 | TCCCTTTCTGTACGATCGAACCAAACACCGGGATTGTACCTGTTCCTGAT | 97 |
| 95. | ACIN548 | TCCCTTTCTGTACGATCGAACCAAACACCGGGATTGTACCTGTTCCTGAT | 97 |
| 95. | ACIN549 | TCCCTTTCTGTACGATCGAACCAAACACCGGGATTGTACCTGTTCCTGAT | 97 |
| 95. | HI0393NUSH | ATCCATTCTGTACTATCGAACCAAATACGGGTGTCGTGCCAATGCCAGAT | 97 |
| | ECPTHGSH | TTCCATTCTGCACCATTGAGCCGAACACAGGCGTCGTGCCAATGCCTGAT | |
| | | . * .* ** ** ** ** ** * .* * ** * . . | |

FIG. 16B

| | | |
|---|---|---|
| 83. | CFETUS17_B | ATACGCTTAAAATGAGCTWRCAAAAATAGTAAATCCA----AATAAAATCC 146 |
| 83. | CFETUS_16 | ATACGCTTAAAATGAGCTWRCAAAAATAGTAAATCCA----AATAAAATCC 146 |
| 83. | CFETUS18_B | ATACGCTTAAAATGAGCTWRCAAAAATAGTAAATCCA----AATAAAATCC 146 |
| 85. | CRECT7_13 | AAGCKCCTAGGCNTGCTARCCAAAATCGTAAATCCA----AATAAAATCC 146 |
| 87. | CHYOI14_13 | GCGCGTTTGAATGAGCTTTCAAAAA------------------------- 125 |
| 89. | ACIN2627 | CCACGTTTAGACAAACTTGCTGCGATTGTTAAACCACAGGTATTTTGCC 147 |
| 89. | ACIN2284 | CCACGTTTAGACAAACTTGCTGCGATTGTTAAACCACAGGTATTTTGCC 147 |
| 91. | ACIN468 | CCACGTTTAGACAAACTTGCTGCGATTGTTAAACCACAGGTATTTTGCC 147 |
| 93. | ACIN1163 | CCACGTTTAGACAAACTTGCTGCGATTGTTAAACCACAGGTATTTTGCC 147 |
| 95. | ACIN45 | CCACGTTTAGACAAATTGACTGCAATTGTTAAACCGCAACGTGTTATTCC 147 |
| 95. | ACIN548 | CCACGTTTAGACAAATTGACTGCAATTGTTAAACCGCAACGTGTTATTCC 147 |
| 95. | ACIN549 | CCACGTTTAGACAAATTGACTGCAATTGTTAAACCGCAACGTGTTATTCC 147 |
| | HI0393NUSH | CCACGTTTAGACGCATTGGCAGAAATCGTTAAGCCTGAAATCGTAAACC 147 |
| | ECPTHGSH | CCTCGCCTGGATCAACTGGCTGAAATCGTAAACCGCAGCGTACGCTTCC 147 |
| | | * * * * . * . . * . . |

FIG. 16C

| | | |
|---|---|---|
| 83. | CFETUS17_B | AACATTCGACTATCGAATTTGTA 169 |
| 83. | DFETUS_16 | AACATTCGACTATCGAATTTGTA 169 |
| 83. | CFETUS18_B | AACATTCGACTATCGAATTT--- 166 |
| 85. | CRECT7_13 | AATACTCCACTATCGAATTCGTC 169 |
| 87. | CHYOI14_13 | ----------------------- 125 |
| 89. | ACIN2627 | AACC-ACAATGGAATTTGT---- 165 |
| 89. | ACIN2284 | AACC-ACAATGGAATTTGT---- 165 |
| 91. | ACIN468 | AACW-ACAATGGAATTTGT---- 165 |
| 93. | ACIN1163 | AACATACAATGGAATTTGT---- 166 |
| 95. | ACIN45 | GAC-TTCTATGGAATTTGT---- 165 |
| 95. | ACIN548 | GAC-TTCTATGGAATTTGT---- 165 |
| 95. | ACIN549 | GAC-TTCTATGGAATTTGT---- 165 |
| | HI0393NUSH | TAC-TACGATGGAATT---CGTG 166 |
| | ECPTHGSH | CAC-GACCATGGAATTTGTCGAT 169 |

FIG. 16D

| seq id no | | | |
|---|---|---|---|
| 84. | CFET17BPR | TTFNALTKASNAESANYPFCTIEPNKAIVPXPDIRLNEXXKIVNPNKIQH | 50 |
| 84. | CFET18BPR | TTFNALTKASNAESANYPFCTIEPNKAIVPVPDIRLNEXXKIVNPNKIQH | 50 |
| 84. | CFET16PR | TTFNALTKASNAESANYXXCTIEPNKAIVPVPDIRLNEXXKIVNPNKIQH | 50 |
| 86. | CRECT7PR | TTFNALTKAQNAESANYPXCTIEXNKAVVPDKXLGXLXKIVNPNKIQY | 50 |
| 88. | CHYOIN14PR | TTFNALTKASNAEXANYXFCTXEPNKAIVXVXDARLNELSK------ | 41 |
| 90. | ACIN2627PR | TLFNALTKAAIA-AENFPFCTIEPNTGIVPVPDPRLDKLAAIVKPQRILP | 49 |
| 92. | ACIN468PR | TLFNALTKAAIA-AENFPFCTIEPNTGIVPVPDPRLDKLAAIVKPQRILP | 49 |
| 94. | ACIN1163PR | TLFNALTKAAIA-AENFPFCTIEPNTGIVPVPDPRLDKLAAIVKPQRILP | 49 |
| 96. | ACIN45PR | TLFNALTKAAIA-AENFPFCTIEPNTGIVPVPDPRLDKLTAIVKPQRVIP | 49 |
| 96. | ACIN548PR | TLFNALTKAAIA-AENFPFCTIEPNTGIVPVPDPRLDKLTAIVKPQRVIP | 49 |
| 96. | ACIN549PR | TLFNALTKAAIA-AENFPFCTIEPNTGIVPVPDPRLDKLTAIVKPQRVIP | 49 |
| 96. | HI0393PR | TLFNALTKAGIE-AANYPFCTIEPNTGVVPMPDPRLDALAEIVKPERILP | 49 |
| | ECPTHGPR | TLFNALTKAGIE-AANFPFCTIEPNTGVVPMPDPRLDQLAEIVKPQRTLP | 49 |
| | | * ******* * . ** .** .. * * . | |

FIG. 17A

| | | |
|---|---|---|
| 84. | CFET17BPR | STIEFV- 56 |
| 84. | CFET18BPR | STIEF-- 55 |
| 84. | CFET16PR | STIEFV- 56 |
| 86. | CRECT7PR | STIEFV- 56 |
| 88. | CHYOIN14PR | ------ 41 |
| 90. | ACIN2627PR | TTMEF-- 54 |
| 90. | ACIN2284PR | TTMEF-- 54 |
| 92. | ACIN468PR | XTMEF-- 54 |
| 94. | ACIN1163PR | TYNGIC- 55 |
| 96. | ACIN45PR | TSMEF-- 54 |
| 96. | ACIN548PR | TSMEF-- 54 |
| 96. | ACIN549PR | TSMEF-- 54 |
| | HI0393PR | TTMEFV- 55 |
| | ECPTHGPR | TTMEFVD 56 |

FIG. 17B

```
                            G-1 like
            5          10          15          20          25          30
  1   M G F K C G I V G L P N V G K S T L F N A L T K A G I E A A
 31   N Y P F C T I E P N T G V V P M P D P R L D A L A E I V K P
                            G-3 like
 61   E R I L P T T M E F V D I A G L V A G A S K G E G L G N K F
 91   L A N I R E T D A I G H V V R C F E N D D I V H V A G K I D
121   P L D D I D T I N T E L A L A D L D S C E R A I Q R L Q K R
151   A K G G D K E A K F E L S V M E K I L P V L E N A G M I R S
181   V G L D K E E L Q A I K S Y N F L T L K P T M Y I A N V N E
211   D G F E N N P Y L D R V R E I A A K E G A V V V P V C A A I
241   E S E I A E L D D E E K V E F L Q D L G I E E P G L N R V I
271   R A G Y A L L N L Q T Y F T A G V K E V R A W T V S V G A T
301   A P K A A A V I H T D F E K G F I R A E V I A Y E D F I Q F
331   N G E N G A K E A G K W R L E G K D Y I V Q D G D V M H F R
361   F N V
```

FIG. 18

POLYNUCLEIC ACID SEQUENCES FOR USE IN THE DETECTION AND DIFFERENTIATION OF PROKARYOTIC ORGANISMS

The present invention relates to the use of the GTPase gene family as a target for nucleic acid based assays for the detection and differentiation of prokaryotic organisms.

The present invention relates to polynucleic acids derived from gene sequences encoding prokaryotic GTPase (=GTP-binding) proteins, as well as their use in the detection and identification of prokaryotic organisms; primers and probes derived from said polynucleic acid sequences, for specific amplification and detection of prokaryotic DNA in a biological sample; as well as methods and kits allowing the detection and identification of at least one micro-organism, and preferentially several micro-organisms simultaneously in a sample.

More specifically, the invention relates to new polynucleic acid sequences encoding GTPase proteins from Campylobacter species, primers and probes derived from them, and methods and kits comprising these reagents for the detection and differentiation of species belonging to the genus Campylobacter.

GTP-binding proteins (also called GTPases because of the GTP hydrolysis that they catalyze) constitute a large family of proteins that all have a similar GTP-binding globular domain. When its bound GTP is hydrolysed to GDP, this domain undergoes a conformational change that inactivates the protein. It is well known that GTP-binding proteins in pro- and eukaryotic organisms show conserved structures and contain common amino acid sequence motifs at their GTP-binding sites (for a review see: Bourne et al., 1991). Although GTP-binding sites show a conserved motif at the amino acid level, sequences are only partially conserved at the nucleic acid level. Prokaryotic GTP-binding proteins have been amply described in literature, and often they are responsable for vital molecular functions in the cell, e.g. they function as elongation and initiation factors in protein synthesis (e.g. for *E. coli*; Zengel et al., 1984; March and Inouye, 1985; Laursen et al., 1981; Sacerdot et al., 1984) and they may have a role in protein translocation across membranes (e.g. for *E. coli*; Bernstein et al., 1989; Römisch et al., 1989; Gill et al. 1986). Some prokaryotic GTP-binding proteins have a still unknown function, like the era-protein from *E. coli* (Ahnn et al. 1986) or the spoOB-associated protein from *Bacillus subtilis* (Trach and Hoch, 1989).

It is an aim of the present invention to use the GTPase gene family as a target for nucleic acid based assays for the detection and differentiation of prokaryotic organisms.

It is an aim of the present invention to provide polynucleic acids derived from the GTPase gene family to be used for the detection and identification of one or several micro-organisms simultaneously in a sample. The use of the polynucleic acids of the invention can be embodied by the use as an oligonucleotide primer, capable of amplifying the prokaryotic polynucleic acids present in the sample, or by the use as an oligonucleotide probe, capable of hybridizing specifically to the polynucleic acids of the different micro-organisms present in the sample.

It is therefore an aim of the present invention to select primer sequences derived from the polynucleic acid sequences encoding prokaryotic GTPase proteins, said primer sequences allowing amplification of part of a GTPase gene of one micro-organism, or of several micro-organisms simultaneously.

It is a more specific aim of the present invention to select primer sequences from the polynucleic acid sequences encoding the GTP-binding sites, said primer sequences allowing the simultaneous amplification of part of a GTPase gene of several micro-organisms.

Another aim of the present invention is to select probe sequences from the polynucleic acid sequences encoding prokaryotic GTPase proteins, said probe sequences allowing specific detection and identification of one or several micro-organisms.

It is a more specific aim of the present invention to select probe sequences from the polynucleic acid sequences encoding the GTP-sites enclosed region, said probe sequences allowing the specific detection and differentiation of several micro-organisms.

It is also an aim of the present invention to provide a rapid and reliable method for the detection and identification of one or several micro-organisms simultaneously in a sample, using the above-mentioned polynucleic acids and/or oligonucleotides derived from them as principle reagents.

It is moreover an aim of the present invention to provide a kit enabling the detection and identification of one or several micro-organisms simultaneously in a sample, comprising the above-mentioned polynucleic acids and/or oligonucleotides derived from them as principle reagents.

In particular, it is an aim of the present invention to provide new polynucleic acid sequences encoding novel GTP-binding proteins, or part of them, from Campylobacter species.

It is more specifically an aim of the present invention to use said new GTPase genes as a target for the detection and differentiation of Campylobacter species.

It is in particular an aim of the present invention to provide for oligonucleotides, primers and probes, derived from said new polynucleic acid sequences, to be used in the specific detection and differentiation of Campylobacter species.

It is also a specific aim of the present invention to provide for a method and a kit enabling the detection and differentiation of Campylobacter species in a sample, and using the above-mentioned new polynucleic acids and/or oligonucleotides derived from them, as principle reagents.

All of these aims are achieved by the polynucleic acids of this invention.

The current invention makes use of the semi-conserved nature of the GTPase gene family, a property which proved to be advantageous for use in nucleic acid based assays applied to bacterial detection, differentiation and identification. Said nucleic acid based assays consist of amplification of the target sequences and/or hybridization to the target sequences. It is shown in the current invention that both universal as well as specific oligonucleotides can be derived from the polynucleic acid sequences encoding GTPases. Both kinds of oligonucleotides have their proper place in bacterial diagnosis, depending on the application.

The term "GTPase gene family" encompasses genes encoding GTPase (GTP binding) proteins (E.C.3.6.1.) in different prokaryotic organisms. These GTPase proteins are structurally related, especially at their GTP-binding sites which show conserved sequence motifs, but they may have different functions in vivo. Although GTPase proteins show a structural relatedness on the protein level, the relatedness on the DNA level may be much less clear.

The term "universal" oligonucleotide (probe and/or primer) signifies that this oligonucleotide hybridizes to and/or allows amplification of part of the GTPase genes from different taxa.

The term "specific" oligonucleotide (probe and/or primer) means that this oligonucleotide hybridizes to and/or allows amplification of part of the GTPase genes from only one taxon.

The term "taxon" may refer to a complete genus, or a subgroup within a genus, a species, or even a subtype within a species.

Depending on the application, the term "universal" oligonucleotide may thus refer to an oligonucleotide allowing the amplification of and/or the hybridization to part of the GTP-ase genes of most of the organisms of one genus, while, in that same application, the term "specific" oligonucleotide may refer to oligonucleotides allowing the amplification of and/or the hybridization to part of the the GTPase gene(s) of only one species of that genus (species-specific oligonucleotides).

The current invention shows that "universal" oligonucleotides may be derived from the polynucleic acid sequences encoding the GTP-binding sites of GTPase proteins, while "specific" oligonucleotides may be derived from the polynucleic acids sequences encoding the GTP-sites enclosed region. It is shown in the current invention that the polynucleic acid sequences encoding the "GTP-sites enclosed regions" are sufficiently variable between different species, and at the same time sufficiently conserved within one species, to allow the selection of species-specific probes from that region. This unique feature, combined with the rather conserved nature of the flanking regions encoding the GTP-binding sites, which allows the selection of universal primer sequences, make the GTPase gene family a particularly good target for nucleic acid based assays for the detection and differentiation of different prokaryotic organisms. This particular application of GTPase encoding nucleic acid sequences in the field of bacterial detection, identification and differentiation has not been suggested uptil now.

The abbreviation GTP stands for guanosine 5'-triphosphate.

The wording "GTP-binding sites" are those regions in the GTP-binding protein responsible for the binding of GTP. GTP-binding sites show evolutionary conserved amino acid motifs. According to Dever et al., 1987 most GTP-binding proteins show 3 to 4 conserved motifs, showing the following consensus sequences:

G-1: GXXXXGK
G-2: D(X)$_{10}$T
G-3: DXXG
G-4: NKXD

The expression "GTP-sites enclosed region" refers to the regions bracketed (flanked) by the GTP-binding sites. Since every GTPase usually contains several GTP-binding sites (see above), they also contain different GTP-sites enclosed regions (e.g. G1–G2, G2–G3, G3–G4, G1–G3 . . . ).

The Examples section describes the isolation and sequencing of new putative GTPase genes, or parts thereof, from Campylobacter species, said genes and the encoded proteins being called from now on c-gtp genes and c-gtp proteins. The examples section further shows the existence of corresponding gene sequences in other prokaryotic species. These corresponding gene and protein sequences, in species other than Campylobacter will be called from now on c-gtp-like genes and proteins.

The wording "c-gtp-like proteins and genes" thus refers to functionally and structurally related proteins to the c-gtp proteins, in prokaryotic organisms other than Campylobacter, and genes coding for the same. The c-gtp-like proteins are substantially homologous to the c-gtp proteins of Campylobacter, with a homology degree on the protein level in excess of 70%, preferably in excess of 80%, most preferably in excess of 90%. The homology on the DNA level may be much less, and preferably more than 50%. The c-gtp-like proteins and genes constitute the "c-gtp-family" of proteins and genes.

Examples I and II of the current invention describe the identification and sequencing of the full gene encoding a new putative GTP-binding protein of *Campylobacter jejuni*, called from now on the c-gtp-1 gene (and protein), the sequence of which is depicted in FIG. 2 (SEQ ID NO 1 and 2). Corresponding gene sequences are shown to exist in other Campylobacter species, as well as in other prokaryotic organisms (like *Haemophilus influenzae* and *Mycobacterium leprae*). Example III further demonstrates that oligonucleotide primers derived from the region encoding the GTP-binding sites in this protein allow the amplification of the target sequence in different thermophylic Campylobacter species, while oligonucleotide probes derived from the region encoding the GTP-sites enclosed region allow the differentiation between different thermophylic Campylobacter species. These experiments show that the c-gtp-1 gene family is a particular good target for the detection and differentiation of prokaryotic organisms, more particularly of Campylobacter species, and even more specifically of thermophylic Campylobacter species.

The wording "thermophylic Campylobacter species" comprises strains belonging to or being highly related to one of the following species: *Campylobacter jejuni, C. coli, C. lari* and *C. upsaliensis*. Thermophylic Campylobacter species are human pathogens commonly involved in infections causing diarrhea, usually as a result of digestion of contaminated food.

The wording "c-gtp-1 gene family" encompasses gene sequences encoding structurally and functionally related proteins to the c-gtp-1 protein of *C. jejuni* as depicted in FIG. 2 (SEQ ID NO 1), also called c-gtp-1 like genes and proteins. Examples of gene sequences from the c-gtp-1 family are depicted in FIG. 8 (SEQ ID NO 3–23) and may originate from organisms belonging to the genus Campylobacter or from other prokaryotic organisms.

Example V describes the identification and partial sequencing of another new putative GTPase gene isolated from Campylobacter species, from now on called c-gtp-2 gene (and protein). The sequence of part of this gene in different veterinary Campylobacter species is shown in the alignment of FIG. 16 (SEQ ID NO 83, 85 and 87). It is shown that analogues of this gene exist in other prokaryotic species (like *Haemophilus influenzae, Eschericia coli* and Acinetobacter). These analogue genes in species other than Campylobacter will from now on be called c-gtp-2 like genes (and proteins). It is further shown that oligonucleotides derived from the GTP-sites enclosed region of the c-gtp-2 like genes allow the detection and differentiation of different veterinary Campylobacter species. These experiments show that the c-gtp-2 gene family is a particular good target for the detection and differentiation of prokaryotic organisms, more particulary of Campylobacter species, and even more specifically of veterinary Campylobacter species.

The wording "veterinary Campylobacter species" encompasses species which are important in veterinary infections, like *Campylobacter fetus, Campylobacter hyointestinalis* and *Campylobacter mucosalis*.

The wording "c-gtp-2 gene family" encompasses gene sequences encoding structurally and functionally related proteins to the c-gtp-2 proteins of Campylobacter species, fragments of which are shown in FIG. 16 (SEQ ID NO 83, 85, 87, 89, 91, 93, 95). These related c-gtp-2 like genes and proteins may originate from organisms belonging to the genus Campylobacter or from other prokaryotic organisms.

Based on the fact that
- the newly described GTPase genes and gene fragments have their homologous counterparts in organisms other than Campylobacter,
- primers can be derived from these GTPase sequences allowing amplification of a corresponding gene fragment in different prokaryotic organisms,
- probes can be derived from these GTPase gene sequences allowing differentiation between species belonging to the same genus (e.g. Campylobacter), the current invention considers it fair to expect that this GTPase gene family is an ideal candidate target for the development of a quasi-universal prokaryotic detection and identification system, consisting of the simultaneous amplification of the GTPase gene, or at least a fragment thereof, from a number of different micro-organisms, followed by the specific detection of the different micro-organisms by hybridisation to specific probes, having this gene, or at least a fragment of it, as a target.

Since the advent of the polymerase chain reaction and some other nucleic acid amplification techniques, the impact of DNA-probe technology on the diagnosis of micro-organisms in samples of different origins is increasing. Being often more specific and potentially more sensitive—if an adequate amplification and/or detection system is used—the DNA probe approach may eventually replace the conventional identification techniques.

The reliability of polynucleic acid based tests essentially depends on the sensitivity and specificity of the probes and/or primers used. Thus the corner-stone of this type of assay is the identification of polynucleic acid sequences which are unique to the group of organisms of interest.

Most of the polynucleic acid based tests described in literature and/or commercially available aim at the detection of just one particular organism in a biological sample. Since certain samples may contain a variety of relevant micro-organisms, a multitude of separate assays would need to be performed to detect all relevant organisms possibly present. This is the case e.g. in biological samples, taken from human subjects suspected to be infected, or in food samples, originating from a contaminated food source, where a number of clinically relevant micro-organisms may be present. Performing a set of assays for each of the different pathogens separately would be expensive, laborious and time-consuming. Consequently, die number of tests actually performed in most routine diagnostic labs on a particular sample is restricted to just a few of the most relevant organisms. Therefore it would be extremely convenient to have access to a system which enables the fast, easy and simultaneous detection of a multitude of different organisms. The more organisms that can be screened for in the same assay, the more cost-effective the procedure would be.

The following definitions serve to illustrate the terms and expressions used in the different embodiments of the present invention as set out below:

The term "target" in the current invention means a polynucleic acid sequence which is amplified by the primers of the current invention and/or hybridized to the probes of the current invention. The target sequences aimed at in the current invention are the GTPase gene sequences or parts thereof.

The term "polynucleic acid" corresponds to either double-stranded or single-stranded cDNA or genomic DNA or RNA, containing at least 10, 20, 30, 40 or 50 contiguous nucleotides. Single stranded polynucleic acid sequences are always represented in the current invention from the 5' end to the 3' end.

Polynucleic acids according to the invention may be prepared by any method known in the art for preparing polynucleic acids (e.g. the phosphodiester method for synthesizing oligonucleotides as described by Agarwal et al. (1972), the phosphotriester method of Hsiung et al. (1979), or the automated diethylphosphoroamidite method of Baeucage et al. (1981)). Alternatively, the polynucleic acids of the invention may be isolated fragments of naturally occurring or cloned DNA or RNA.

The term "oligonucleotide" refers to a single stranded nucleic acid comprising two or more nucleotides, and less than 100 nucleotides. The exact size of an oligonucleotide depends on the ultimate function or use of said oligonucleotide. For use as a probe or primer the oligonucleotides are preferably about 5–50 nucleotides long.

The oligonucleotides according to the present invention can be formed by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, e.g. by automatic synthesis on commercial instruments sold by a variety of manufacturers.

The nucleotides as used in the present invention may be ribonucleotides, deoxyribonucleotides and modified nucleotides such as inosine or nucleotides containing modified groups which do not essentially alter their hybridisation characteristics. Moreover, it is obvious to the man skilled in the art that any of the below-specified probes can be used as such, or in their complementary form, or in their RNA form (wherein T is replaced by U).

The oligonucleotides used as primers or probes may also comprise or consist of nucleotide analogues such as phosphorothioates (Matsukura et al., 1987). alkylphosphorothioiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention, these variations will necessitate adaptions with respect to the conditions under which the oligonucleotide should be used to obtain the required specificity and sensitivity. However the eventual results of the hybridisation or amplification will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The term "probe" refers to single stranded sequence-specific oligonucleotides which have a sequence which is sufficiently complementary to hybridize to the target sequence to be detected.

Preferably said probes are 70%, 80%, 90%, or more than 95% homologous to the exact complement of the target sequence to be detected. These target sequences are either genomic DNA or messenger RNA, or amplified versions thereof.

Preferably, these probes are about 5 to 50 nucleotides long, more preferably from about 10 to 30 nucleotides.

The term "hybridizes to" refers to preferably stringent hybridizations conditions, allowing hybridisation between sequences showing at least 70%, 80%, 90%, 95% or more homology with each other.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA targets, as well as on the conditions of primer use such as temperature and ionic strength. The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR: Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et at., 1989), strand displacement amplification (SDA: Duck, 1990; Walker et al., 1992) or amplification by means of Qβ replicase (Lizardi et al., 1988; Lomeli et al., 1989) or any other suitable method to amplify nucleic acid molecules.

The term "labelled" refers to the use of labelled nucleic acids. This may include the use of labelled nucleotides incorporated during the polymerase step of the amplification such as illustrated by Saiki et al. (1988) or Bej et al. (1990) or labelled primers, or by any other method known to the person skilled in the art. Labels may be isotopic ($^{32}P$, $^{35}S$, etc.) or non-isotopic (biotin, digoxigenin, etc.).

The term "complementary" nucleic acids as used in the current invention means that the nucleic acid sequences can form a perfect base paired double helix with each other.

The term "homologous" as used in the current application is synonymous for identical; this means that polynucleic acids (proteins) which are said to be e.g. 80% homologous show 80% identical base pairs (amino acids) in the same position upon alignment of the sequences.

The term "sample" refers to any biological material taken either directly from an infected human being (or animal), or after culturing (enrichment), or a sample taken from food or feed. Biological material may be e.g. faecal samples, urine, expectorations of any kind, broncheolavages, blood, skin tissue, biopsies, lymphocyte blood culture material, colonies, etc. Said samples may be prepared or extracted according to any of the techniques known in the art.

The term "solid support" can refer to any substrate to which an oligonucleotide probe can be coupled, provided that it retains its suitable hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

As described above, the present invention thus relates to the use of the GTPase gene family as a target for nucleic acid based assays for the detection and/or differentiation of prokaryotic organisms.

The present invention more particularly relates to the use of the GTPase gene family as a target for nucleic acid based assays for the differentiation of prokaryotic organisms.

Nucleic acid based assays may include the amplification of the target nucleic acids and/or the hybridization of the (amplified) target nucleic acids, and the detection of the resulting amplification and/or hybridization products.

In particular, the current invention relates to the use of the GTPase gene family as a target for nucleic acid based assays for the detection and/or differentiation of different Campylobacter species.

More specifically, the current invention relates to the use of the c-gtp gene family as a target for nucleic acid based assays for the detection and/or differentiation of different Campylobacter species.

In a very specific embodiment the invention relates to the use of the c-gtp-1 family as a target for the detection and/or differentiation of thermophylic Campylobacter species.

Figure 12:
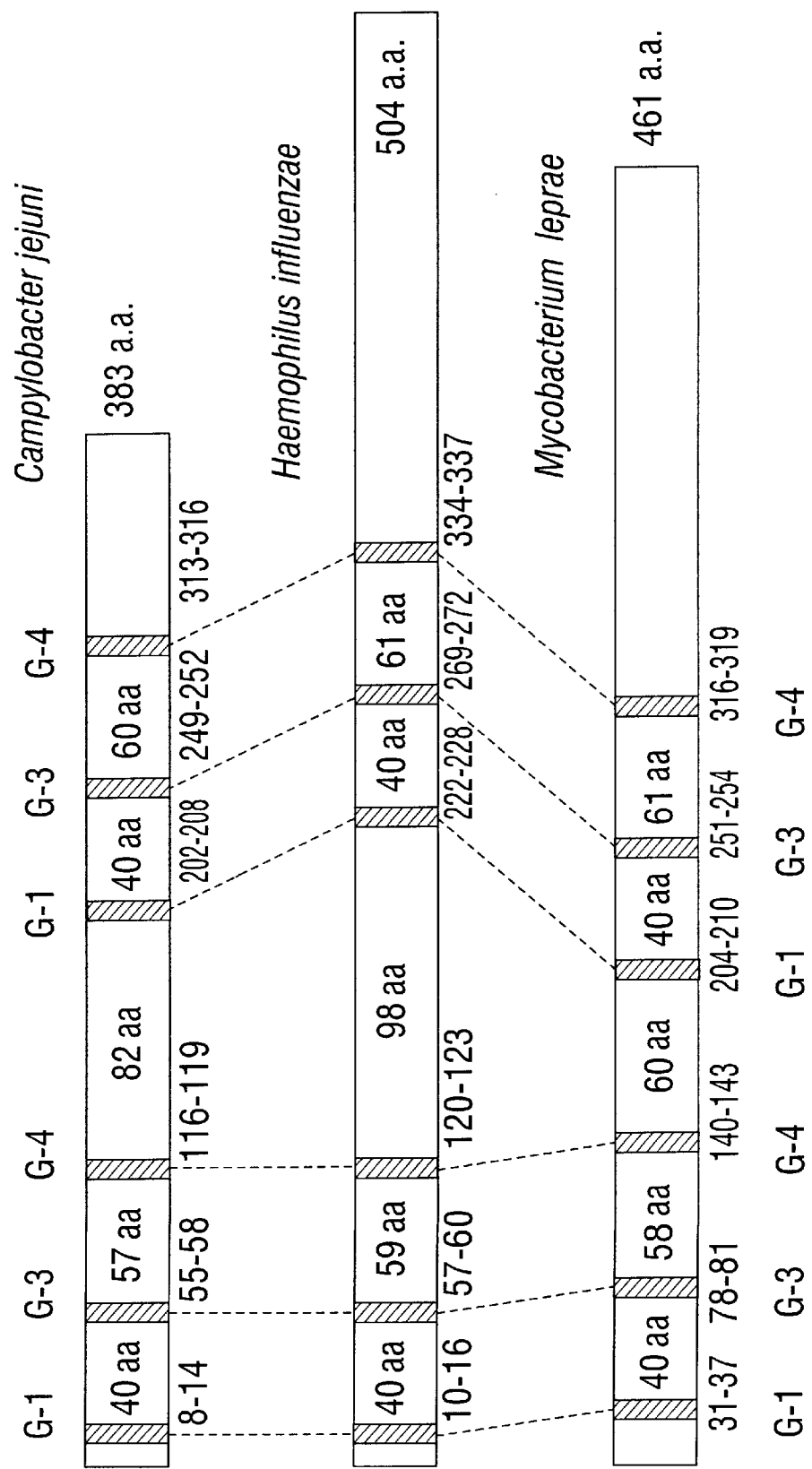

The c-gtp-1 gene of *Campylobacter jejuni* is represented in FIG. 2 (SEQ ID NO 1). The different GTP-binding motifs in the corresponding c-gtp-1 protein are boxed. A characteristic feature of the c-gtp 1 protein is the repeat of the GTP-binding domain in the protein, which is clear from the structural organisation of the c-gtp-1 gene shown in FIG. 1. The presence of two GTP-binding domains in one protein is quite exceptional. After searching the protein data banks, only two other putative GTP-binding proteins were found to show an analogous repeat structure, i.e., a putative GTP-binding protein of *Haemophilus influenzae* (H10136) and a putative GTP-binding protein of *Mycobacterium leprae* (u0247e). An alignment of these three proteins, both on the structural level as on the sequence level is shown in FIGS. 12 and 11, respectively.

Part of the c-gtp-1 gene is also sequenced in other Campylobacter species, more specificalyy in the thermophylic Campylobacter species. *C. coli, C. lari* and *C. upsaliensis*. The sequences of the GTP-sites (G1–G3) enclosed region of the first GTP-binding domain in these different organisms, are represented in the alignment of FIG. 8 (SEQ ID NO 3–23).

All the above-mentioned c-gtp-1 like genes (and gene fragments) belong to the c-gtp-1 gene family.

Another embodiment of the invention relates to the use of the c-gtp-2 gene family as a target for nucleic acid based assays for the detection and/or differentiation of different Campylobacter species.

In a very specific embodiment the invention relates to the use of the c-gtp-2 gene family as a target for nucleic acid based assays for the detection and differentiation of different veterinary Campylobacter species.

The sequence of one of the GTP-sites (G1–G3) enclosed regions of the c-gtp-2 gene in different veterinary Campylobacter species is shown in FIG. 16 (SEQ ID NO 83, 85, 87). The corresponding fragments of the homologous genes from other prokaryotic organisms are aligned with it. These homologous sequences all belong to the c-gtp-2 gene family.

The present invention relates in particular to a polynucleic acid comprising one of the following sequences:
(i) the polynucleic acid sequence extending from nucleotide position 865 to position 2016 of SEQ ID NO 1, or
(ii) one of the polynucleic acid sequences represented by SEQ ID NO 3, 4, 5, 6, 7, 8, 9, 10, 11, 12, 13, 14, 15 16, 17, 18, 19, 20, 21, 22, or 23, or
(iii) one of the polynucleic acid sequences represented by SEQ ID NO 83, 85, 87, 89, 91, 93, or 95, or
(iv) a polynucleic acid sequence consisting of a fragment containing at least 8 contiguous nucleotides of any of the sequences as specified in (i) to (iii), or
(v) a polynucleic acid sequence complementary to any of the sequences as specified in (i) to (iv), or (vi) a polynucleic acid sequence hybridizing to any of the sequences as specified in (i) to (v), or (vii) a polynucleic acid sequence showing at least 50%, 60%, 70%, 80%, 90%, 95% or more homology to any of the sequences represented by (i) to (v), or (viii) a polynucleic acid sequence as specified in any of (i) to (vii) wherein T is replaced by U, or other variants of the above specified sequences.

Other variants of the above-specified polynucleic acid sequences may contain modified nucleotides, such as inosine or nucleotides containing modified groups which do not alter essentially their hybridisation characteristics. They may also contain nucleotide analogues, such as phosphorothioates (Matsukura et al., 1987), alkylphosphorothioates (Miller et at., 1979) or peptide nucleic acids (Nielsen et al., 1991; Nielsen et al., 1993) or may contain intercalating agents (Asseline et al., 1984).

The "fragments" as defined in point (iv) of the above-mentioneded embodiment may be used in different applications. e.g. as a probe or as a primer, in different hybridization and/or amplification reactions.

More particularly, the present invention relates to the use of the above-mentioned polynucleic acid sequences for use in a diagnostic method. Even more particularly, the present invention relates to the preparation of a medicament for diagnosing at least one micro-organism, and preferably several micro-organisms simultaneously in a biological sample. The expression "the preparation of a medicament for diagnosing . . . " refers to the preparation of a diagnostic composition.

The invention more particularly provides for said polynucleic acids to be used in the detection and identification of at least one micro-organism, and preferably several micro-organisms simultaneously in a biological sample.

The polynucleic acids of the invention as specified above encode c-gtp-1 proteins and the likes, or fragments thereof (SEQ ID NO 1, 3–23), or c-gtp-2 proteins and the likes, or fragments thereof (SEQ ID NO 83, 85, 87, 89, 91, 93 or 95) or the homologues of these proteins in other prokaryotic organisms.

It should be understood that the polynucleic acids of the invention are different from the gene encoding a hypothetical protein H10136 of *H. influenzae* the gene encoding a hypothetical protein u0247e of *M. leprae* the gene encoding a hypothetical protein H10393 of *H. influenzae* the gene encoding a hypothetical protein ECPTHGSH of *E. coli*.

These sequences encode c-gtp-1 and c-gtp-2 homologous proteins which have already been disclosed in the prior art, as described further in the Examples section.

It is clear that the polynucleic acids of the invention may also contain polynucleic acid sequences degenerate to any of the sequences SEQ ID NO 1, 3–23 and 83, 85, 87, 89, 91, 93, 95 as a result of the genetic code degeneracy, said degenerate sequences still encoding a prokaryotic c-gtp-like protein or part of it.

The polynucleic acids of the invention may also encode functional analogues of the above-mentioned proteins, said functional analogues being substantially homologous to the proteins encoded by any of the sequences represented by SEQ ID NO 1, 3 to 23, 83, 85, 87, 89, 91, 93 or 95.

By "substantially homologous" as used throughout the specification and the claims to describe proteins and peptides, is meant a degree of homology in the amino acid sequence to the proteins or peptides of the invention. Preferably the degree of homology is in excess of 80, preferably in excess of 90, with a particulary preferred group of proteins being in excess of 95 with the proteins and peptides of the invention.

From the above it is clear that the degree of homology within the family of polypeptides and the polynucleic acids of the invention is significantly higher on the protein level (70% or more) than on the DNA level (50% or more). It is therefor more appropiate to define the family of polynucleic acids of the invention by means of the polypeptides that they are encoding.

The term "functional analogue" refers to any protein or peptide having an amino acid sequence substantially identical to the sequence from which they are derived, whereby one or more amino acid residues have been conservatively substituted with a biologically equivalent residue. Examples of conservative substitutions include the substitution of one apolar (hydrophobic) residue such as isoleucine, valine leucine or methionine for another, the substitution of one polar (hydrophylic) residue for another such as between argininine and lysine, between glutamine and asparagine, between glycine and serine, the substitution of one basic residue such as lysine, arginine, or histidine, for another, or the substitution of one acidic residue, such as aspartic acid, or glutamic acid, for another. Examples of allowable mutations according to the present invention can be found in Table 1. Functional analogues may comprise isolates of the c-gtp genes in organisms other than Campylobacter, or may comprise muteins prepared in vitro from the above-specified sequences.

TABLE 1

Overview of the amino acid substitutions which could form the basis of functional analogues as defined above.

| Amino acids | Synonymous groups |
|---|---|
| Ser (S) | Ser, Thr, Gly, Asn |
| Arg (R) | Arg, His, Lys, Glu, Gin |
| Leu (L) | Leu: Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, lle, Tyr, Phe, Leu, Val |
| Gly (C) | Gly, Ala, Thr, Pro, Ser |
| Ile (I) | Ile, Met, Leu, Phe, Val, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

The present invention thus relates to a polynucleic acid comprising one of the following sequences, or fragments thereof:

(a) a polynucleic acid sequence encoding a c-gtp-like protein or fragment thereof, as defined above, or (b) a polynucleic acid sequence encoding a functional analogue of the above-mentioned c-gtp-like protein, or (c) a polynucleic acid sequence which is degenerate as a result of the genetic code degeneracy to the polynucleic acid sequences as defined in (a) or (b), or (d) a polynucleic acid sequence hybridizing to any of the polynucleic acid sequences as defined in (a) to (c).

It should be understood that fragments of the above-mentioned polynucleic acids should contain a contiguous sequence of at least 8 nucleotides selected from the original polynucleic acid sequence.

It should be understood that the above-mentioned c-gtp-like genes and proteins originate from prokaryotic organisms.

In a more specific embodiment, the invention relates to polynucleic acids and the use thereof as described above, said polynucleic acids encoding c-gtp-like genes originating from Campylobacter species.

In a particular embodiment said polynucleic acids are used for detection and identification of one or several Campylobacter species simultaneously in a biological sample.

Another embodiment of the invention provides for an oligonucleotide primer derived from the GTPase gene family of sequences and hybridizing to the polynucleic acid sequences encoding the GTP-binding sites, said GTP-binding sites being represented by the following consensus sequences:

G-1: GXXXXGK$^S_T$
G-3: DXXG
G-4: NKXD.

Combination of two such primers, in a primerset, allows the amplification of the GTP-sites enclosed region.

The selection of the primer sequences should result preferentially in an oligonucleotide sequence capable of amplifying the GTP-sites enclosed regions of different taxa (e.g. different genera, different species, different subspecies) simultaneously.

A specific embodiment of the invention provides for an oligonucleotide primer selected from the c-gtp-gene family of sequences, and hybridizing to part of a polynucleic acid sequence as described above.

Preferably said primer comprises an oligonucleotide sequence containing from 5 to the maximum number of contiguous nucleotides, more preferably from 10 to 30 contiguous nucleotides of any of the sequences represented by SEQ ID NO 1, 3–23, 83, 85, 87, 89, 91, 93, 95 or their complementary sequences, or variants of said sequences, provided that said variants still allow the amplification of the c-gtp-like gene fragment of the taxon of interest.

The term "variants" of a primer includes variants differing in sequence by changing, adding or deleting one or more nucleotides, or by substituting one or more nucleotides withing said sequence, provided that said variants still allow amplification of the same nucleic acid fragments as the primers from which they are derived. The fact that amplification primers do not have to match perfectly with the corresponding template sequence to warrant proper amplification is amply documented in literature (e.g. Kwok et al. 1990).

Special note should be taken of the fact that the primers of the current invention can be used both as sense and as antisense primers. In the latter case, the sequence of the oligonucleotide primer should be the reverse complement of the sequences as specified in the current invention.

In a particular embodiment, the invention provides for a primer as described above, comprising or consisting of an oligonucleotide sequence which specifically hybridizes to the polynucleic acid fragments encoding the GTP-binding sites in the c-gtp-like genes as defined above, or their complementary sequences. This particular type of primer allows amplification of the GTP-sites enclosed regions of the c-gtp-like genes. Moreover, this type of primer may amplify the GTP-sites enclosed fragments of the gene in different prokaryotic micro-organisms, due to its conserved nature. Therefore, this type of primer will be preferentially used in a method for detection and identification of several micro-organisms simultaneously in a sample.

In a more specific embodiment of the invention a primer is provided as described above, comprising at least one of the following oligonucleotide sequences:
SEQ ID NO 24: CCAAATGTTGGAAAATCA
SEQ ID NO 25: GCCAAATGTTGGiAARTC
SEQ ID NO 26: AAiCCAAATGTTGGiAAR
SEQ ID NO 27: GGCAAiCCAAATGTiGG
SEQ ID NO 28: ATGTTGGAAAATCAAGYC
SEQ ID NO 29: ATCAAGTTTATTTAAC
SEQ ID NO 30: TAGACTTCGAAGAAAGCGC
SEQ ID NO 31: CATAGCAAGGCAAAGAATCGCC
SEQ ID NO 32: GATAGTGGAGGGCTTGAT
SEQ ID NO 33: GAYAGiGGAGGGCTTGAT
SEQ ID NO 34: GAYAGiSSAGGiCTiGAT
SEQ ID NO 35: GGGCTTGATGAAAGTGAT
SEQ ID NO 36: GGCTTTTTTTGAATGAATATGAAT
SEQ ID NO 37: CCCTCCACTATCAATAATAG
SEQ ID NO 38: GCCATCAATTTGTACTTCTA
SEQ ID NO 39: TTAAAAGCTCAGGCTTC
SEQ ID NO 80: AATAAAGTAGATAATAAAAAA
SEQ ID NO 81: AAYAARGTIGRiAAYAAAAAA
or variants of these primers, provided that said variants are still able to amplify part of the c-gtp-like gene(s) of the taxon of interest.

Primers represented by SEQ ID NO 24, 25, 26, 27 32, 33, 34, 35, 80 and 81 or variants thereof are derived from the GTP-sites and allow amplification of the GTP-sites enclosed region in one or several micro-organisms simultaneously.

Primers represented by SEQ ID NO 28, 29, 30, 31, 36, 37, 38, 39 or variants thereof are derived from the regions flanking the GTP-sites and allow species-specific amplification of part of the c-gtp genes.

In a specific embodiment, the invention provides for a set of primers as described above, able to amplify part of the c-gtp-like gene(s) in different prokaryotic organisms, and comprising at least one of the following sets of sequences:
A: SEQ ID NO 24 and SEQ ID NO 32
B: SEQ ID NO 25 and (SEQ ID NO 33 and SEQ ID NO 34)
C: SEQ ID NO 26 and (SEQ ID NO 33 and SEQ ID NO 34)
D: SEQ ID NO 27 and (SEQ ID NO 33 and SEQ ID NO 34)
E: SEQ ID NO 25 and SEQ ID NO 35
F: SEQ ID NO 26 and SEQ ID NO 35
and most preferably comprising the following set of primers:
B: SEQ ID NO 25 and (SEQ ID NO 33 and SEQ ID NO 34),
or variants of these primers, provided that said variants are still able to amplify part of the c-gtp-like gene(s) in different prokaryotic organisms.

In a more specific embodiment, the invention provides for a set of primers as described above, able to amplify the GTP-sites enclosed region of the c-gtp gene of Campylobacter species, and comprising at least one of the following sets of primers:
A: SEQ ID NO 24 and SEQ ID NO 32
B: SEQ ID NO 25 and (SEQ ID NO 33 and SEQ ID NO 34)
C: SEQ ID NO 26 and (SEQ ID NO 33 and SEQ ID NO 34)
and most preferably comprising the following set of primers:
C: SEQ ID NO 26 and (SEQ ID NO 33 and SEQ ID NO 34).
or variants of these primers, provided that said variants are still able to amplify the GTP-sites enclosed region of the c-gtp gene(s) in Campylobacter species.

In a more particular embodiment, the invention provides for a set of primers as described above, able to amplify part of the c-gtp-1 gene of *Campylobacter jejuni*, and comprising at least one of the following sets of primers:

SEQ ID NO 25 and (SEQ ID NO 33 and SEQ ID NO 34)
SEQ ID NO 26 and (SEQ ID NO 33 and SEQ ID NO 34)
SEQ ID NO 28 and SEQ ID NO 36,
or variants of these primers, provided that said variants are still able to amplify part of the c-gtp-1 gene in *Campylobacter jejuni.*

In a more particular embodiment, the invention provides for a set of primers as described above, able to amplify part of the c-gtp-1-like gene of *Campylobacter coli*, and comprising at least one of the following sets of primers:
SEQ ID NO 25 and (SEQ ID NO 33 and SEQ ID NO 34)
SEQ ID NO 26 and (SEQ ID NO 33 and SEQ ID NO 34)
SEQ ID NO 29 and SEQ ID NO 37,
or variants of these primers, provided that said variants are still able to amplify part of the c-gtp-1 like gene in *Campylobacter coli.*

In a more particular embodiment, the invention provides for a set of primers as described above, able to amplify part of the c-gtp-1 like gene of *Campylobacter lari*, and comprising at least one of the following sets of primers:
SEQ ID NO 25 and (SEQ ID NO 33 and SEQ ID NO 34)
SEQ ID NO 26 and (SEQ ID NO 33 and SEQ ID NO 34)
SEQ ID NO 30 and SEQ ID NO 38,
or variants of these primers, provided that said variants are still able to amplify part of the c-gtp-1 like gene in *Campylobacter lari.*

In a more particular embodiment, the invention provides for a set of primers as described above, able to amplify part of the c-gtp-1 like gene of *Campylobacter upsaliensis*, and comprising at least one of the following sets of primers:
SEQ ID NO 25 and (SEQ ID NO 33 and SEQ ID NO 34)
SEQ ID NO 26 and (SEQ ID NO 33 and SEQ ID NO 34)
SEQ ID NO 31 and SEQ ID NO 39.
or variants of these primers, provided that said variants are still able to amplify part of the c-gtp-1 like gene in *Campylobacter upsaliensis.*

In another embodiment, the invention provides for a set of primers as described above, able to amplify part of the c-gtp-2 gene of veterinary Campylobacter species, and comprising at least the following primer set:
SEQ ID NO 26 and (SEQ ID NO 33 and SEQ ID NO 34
or variants of these primers, provided that said variants are still able to amplify part of the c-gtp-2 like gene in veterinary Campylobacter species.

In another embodiment, the invention provides for a set of primers as described above, able to amplify part of the c-gtp-2 gene of Acinetobacter species, and comprising at least the following primer set:
SEQ ID NO 26 and (SEQ ID NO 33 and SEQ ID NO 34
or variants of these primers, provided that said variants are still able to amplify part of the c-gtp-2 like gene in Acinetobacter species.

The invention also provides for a combination of different primersets, said combination to be used simultaneously or consecutively in the amplification reaction. A combination of primersets can be used e.g. in a nested PCR reaction, aimed at a more sensitive and/or more specific detection.

Another embodiment of the invention provides for an oligonucleotide probe hybridizing with the GTPase gene family sequences, more specifically hybridizing with the GTP-sites enclosed region.

The selection of the probes according to the present invention occurs via a method as defined further, and results in probes allowing the identification of one taxon, and the differentiation towards other closely related taxa (=closest neighbours).

The term "closest neighbour" means the taxon which is known or expected to be most closely related in terms of DNA homology with the organism of interest and which has to be differentiated from it.

Another embodiment of the invention provides for an oligonucleotide probe hybridizing specifically with any of the above-defined polynucleic acids, said probe to be used for the specific detection of one or more micro-organisms by hybridisation to their polynucleic acids, either directly or after amplification of the polynucleic acids of the respective micro-organisms.

The invention further provides for an oligonucleotide probe as defined above selected from the c-gtp gene family of sequences and comprising part of any of the polynucleic acid sequences as defined above, or variants of said sequences, provided that said variants still hybridize specifically with the c-gtp-like gene fragment of the taxon of interest.

More particularly, the invention provides for a probe as described above, characterized by the fact that its sequence is contained in the region bracketed by the sequences coding for the GTP-binding sites of the c-gtp-like protein, this region being called the "GTP-sites enclosed region". This region shows sufficient sequence diversity to allow differentiation of the species concerned from its closest neighbours and, on the other hand, sufficient sequence conservation to allow the detection of all strains of the species concerned.

The invention relates to an oligonucleotide probe as defined above obtainable by a process comprising the steps of:

(a) amplifying, using a pair of primers as described above, a GTP-sites enclosed region(s) present in the GTPase gene(s) of the organism to be determined, and repeating the same for a number of other organisms, phylogenetically closely related to the organism to be determined (=closest neighbours), or suspected of being present in the same type of sample as the organism to be determined, (b) determining the sequences of the amplified regions, (c) aligning the sequences obtained to allow mutual comparison, and selecting a region in the sequence of the organism to be determined, said region being characterized by a maximal sequence conservation within the organism to be determined, and a maximal sequence divergence (minimum 1 basepair mismatch) towards the other organisms, (d) generating a probe comprising a sequence of at least 8 contiguous nucleotides from the region selected in (c), (e) defining the hybridization conditions required to obtain the desired hybridization characteristics for the probe selected in (d).

It should be understood that probes obtained by the above-mentioned process may still need minor modifications to obtain the desired hybridization characteristics. Said modifications may include addition to and/or removal from any of their respective extremities of one or more nucleotides, or changing one or more nucleotides within said sequence.

The term "variants" of a probe refers to modified probe sequences as specified above. or probe sequences containing modified nucleotides, such as inosine or nucleotides containing modified groups which do not alter essentially their hybridisation characteristics. They may also contain nucleotide analogues, such as phosphorothioates (Matsukura et al., 1987), alkylphosphorothioates (Miller et al., 1979) or peptide nucleic acids (Nielsen et al., 1991; Nielsen et al., 1993) or may contain intercalating agents (Asseline et al., 1984).

In addition, it should be clear that all probes mentioned in the current invention can also be used in their complementary form.

The invention also relates to the above-mentioned method for the selection and generation of probes from the GTPase target gene family.

The expression "desired hybridisation characteristic" means that the probe only hybridizes to the DNA or RNA from organisms for which it was designed, and not to DNA or RNA from other organisms (closest neighbours or organisms liable to be present in the same sample). In practice, this means that the intensity of the hybridization signal is at least two, three, four, five, ten or more times stronger with the target DNA or RNA from the organisms for which the probes were designed, as compared to non-target sequences.

The hybridization conditions can be partially predicted from the oligonucleotide sequence of the probe according to principles known in the art. The conditions can be further monitored experimentally relying upon several parameters, such as the nature and concentration of the components of the media, and the temperatures under which the hybrids are formed and washed.

In a preferred hybridization medium, containing 5×SSC, hybridization temperatures can range from 35° to 65°, and more preferably from 40° to 50°. A preferred wash medium contains 2×SSC.

However, when modifications are introduced, be it either in the probes or the media, the temperatures at which the probes can be used to obtain the required specificity should be changed according to known relationships, such as those described in the following reference:

Hames B and Higgins S (eds.), Nucleic acid hybridization, A practical approach, IRL Press, Oxford, U.K., 1985.

Particularly, the invention provides for a probe as described above, hybridizing specifically to the DNA of thermophylic Campylobacter species, and comprising at least one of the sequences represented by SEQ ID NO 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70, or any oligonucleotide probe selected from any of the sequences represented by SEQ ID NO 1, 3, 4, 5, 6, 7, 8, 9, 10, 11, 12, 13, 14, 15, 16, 17, 18, 19, 20, 21, 22, 23 or 82 as long as said probe can be caused to hybridize specifically to DNA of thermophylic Campylobacter species, or variants of said probes, provided that said variants still hybridize specifically to the DNA of thermophylic Campylobacter species.

In a specific embodiment, the invention provides for an oligonucleotide probe as described above, hybridizing specifically to the DNA of *Campylobacter jejuni*, and comprising at least one of the sequences represented by SEQ ID NO 41, 42, 43, 44, 45, 61, 62, 63, 64, or any oligonucleotide probe selected from any of the sequences represented by SEQ ID NO 1, 3, 4, 5, 6, 7, 8, 9 or 10 as long as said probe can be caused to hybridize specifically to *C. jejuni* DNA, or variants of said probes, provided that said variants still hybridize specifically to the DNA of *C. jejuni*.

Another specific embodiment of the invention provides for an oligonucleotide probe as described above, hybridizing specifically to the DNA of *C. coli* and comprising at least one of the sequences represented by SEQ ID NO 46, 47, 48, 65, 66, 67, 68, or any oligonucleotide probe selected from any of the sequences represented by SEQ ID NO 11, 12, 13, 14, 15 or 16 as long as said probe can be caused to hybridize specifically to *C. coli* DNA, or variants of said probes, provided that said variants still hybridize specifically to the DNA of *C. coli*.

Another specific embodiment of the invention provides for an oligonucleotide probe as described above, hybridizing specifically to the DNA of *C. lari* and comprising at least one of the sequences represented by SEQ ID NO 49, 50, 51, 52, 53, 54, 55, 56, or any oligonucleotide probe selected from any of the sequences represented by SEQ ID NO 17, 18, 19, 20 or 21 as long as said probe can be caused to hybridize specifically to *C. lari* DNA, or variants of said probes, provided that said variants still hybridize specifically to the DNA of *C. lari*.

Another specific embodiment of the invention provides for an oligonucleotide probe as described above, hybridizing specifically to the DNA of *C. upsaliensis* and comprising at least one of the sequences represented by SEQ ID NO 57, 58, 59, 60, 69, 70, or any oligonucleotide probe selected from any of the sequences represented by SEQ ID NO 22 or 23 as long as said probe can be caused to hybridize specifically to *C. upsaliensis* DNA, or variants of said probes, provided that said variants still hybridize specifically to the DNA of *C. uspsaliensis*.

In another embodiment of the invention an oligonucleotide probe is provided as described above, hybridizing specifically to the DNA of veterinary Campylobacter species, and comprising at least one of the sequences represented by SEQ ID NO 71, 72, 73, 74, 75, 76, 77, 78, or 79, or any oligonucleotide probe selected from any of the sequences represented by SEQ ID NO 83 or 87, as long as said probe can be caused to hybridize specifically to DNA of veterinary Campylobacter species, or variants of said probes, provided that said variants still hybridize specifically to the DNA of veterinary Campylobacter species.

Another embodiment of the invention provides for an oligonucleotide probe as described above, hybridizing specifically to the DNA of *Campylobacter fetus*, and comprising at least one of the sequences represented by SEQ ID NO 71, 72, 73, 74, or 75, or any oligonucleotide probe selected from the sequence represented by SEQ ID NO 83 as long as said probe can be caused to hybridize specifically to DNA of *Campylobacter fetus*, or variants of said probes, provided that said variants still hybridize specifically to the DNA of *Campylobacter fetus*.

Another specific embodiment of the invention provides for an oligonucleotide probe as described above, hybridizing specifically to the DNA of *Campylobacter hyointestinalis*, and comprising an oligonucleotide sequence represented by at least one of the sequences represented in any of SEQ ID NO 76, 77, 78 or 79 or any oligonucleotide probe selected from the sequence represented by SEQ ID NO 87 as long as said probe can be caused to hybridize specifically to DNA of *Campylobacter hyointestinalis*, or variants of said probes, provided that said variants still hybridize specifically to the DNA of *Campylobacter hyointestinalis*.

Another embodiment of the invention provides for an oligonucleotide probe as described above, hybridizing specifically to the DNA of Acinetobacter species, and comprising part of any of the polynucleotide sequences represented by SEQ ID NO 89, 91, 93 or 95, as long as said probe can be caused to hybridize specifically to DNA of Acinetobacter species, or variants of said probes, provided that said variants still hybridize specifically to the DNA of Acinetobacter species.

Furthermore, the invention provides for a method for the detection and identification of at least one micro-organism, or the simultaneous detection of several micro-organisms in a biological sample, said method comprising the steps of:

(i) if need be releasing, isolating or concentrating the polynucleic acids present in the sample, (ii) if need be amplifying part of the genomic DNA, with a set of primers as described above, (iii) hybridizing the polynucleic acids of (i) or (ii) with at least one of the probes as described above, (iv) detecting the hybrids formed in step (iii) with each of the probes under appropiate hybridization and wash conditions, (v) identification of the micro-organisms present in the sample from the differential hybridisation signals obtained in (iv).

Detection and identification of the amplified products can be conveniently performed by using one of the many electrophoresis methods, hybridization methods or sequencing methods described in literature and currently known by men skilled in the art. However, a very convenient and advantageous technique for the simultaneous detection of nucleic acids possibly present in biological samples is the Line Probe Assay technique. The Line Probe Assay (LiPA) is a reverse hybridization format (Saiki et al., 1989) using membrane strips onto which several oligonucleotide probes (including negative or positive control oligonucleotides) can be conveniently applied as parallel lines.

The LiPA technique, as described by Stuyver et al. (1993) and in international Application WO 94/12670, provides a very rapid and user-friendly hybridization test. Results can be read within approximately 4 h, after the start of the amplification. After amplification during which usually a non-isotopic label is incorporated in the amplified product, and alkaline denaturation, the amplified product is contacted with the probes on the membrane and the hybridization is carried out for about 0.5 to 1.5 h. Consequently,, the hybrids formed are detected by an enzymatic procedure resulting in a visual purple-brown precipitate. The LiPA format is completely compatible with commercially availabe scanning devices, thus rendering automatic interpretation of the results very reliable. All those advantages make the LiPA format liable for use in a routine setting. The LiPA format therefore is particularly advantageous for detecting simulaneously the presence of different pathogens possibly present in a sample.

The LiPA format is not only an advantageous tool for identification and detection of pathogens at the species level but also at higher or lower taxonomical levels. For instance, probe-configurations on LiPA strips can be selected in such a manner that they allow the detection of a complete genus (e.g. Campylobacter) or can identify species within a genus (e.g. *C. jejuni, C. coli* . . . ) or can in some cases even detect subtypes (subspecies, serovars, sequevars, biovars, etc. whatever is clinically relevant) within a species.

The fact that different probes can be combined on one strip also offers the possibility to conveniently cope with lack of sensitivity due to sequence heterogenity in the target region of the group of organisms to be detected. Due to this heterogenity, two or more probes may be required to positively detect all organisms of the particular group. These probes can be applied to membrane strips at different locations and the result is interpreted as positive if one of these probes is positive. Alternative these probes can be applied as a mixture at the same location, hereby reducing the number of lines on a strip. This reduction may be convenient in order to make the strip more concise or to be able to extend the total number of probes on one strip. An alternative advantage, in view of its practical benefits, is the synthesis of oligonucleotides harbouring the sequences of two (or more) different probes which can then be further processed and applied to the strip as one oligonucleotide molecule. This approach would considerably simplify the manufacturing procedures of the LiPA-strips. For example, probes with nucleotide sequences A and B are both required to detect all strains of taxon X. A probe can be synthesized having the nucleotide sequence AB. This probe will have the combined characteristics of probes A and B.

As an example, the procedure to be followed for the detection of a particular pathogen in a sample using the LiPA format is outlined below:

Firstly, the nucleic acid in the sample in which the infectious agent or agents present should be identified, is made available for amplification and/or hybridization.

Secondly, the nucleic acids are, if need be, amplified with one or another target amplification system. By using universal primers the GTP-sites enclosed region of most if not all organisms of eubacterial origin will be amplified.

The same result might be obtained by using a combination of different sets of primers with reduced universality. For some amplifications it might be convenient to amplify not all organisms present in the sample but more specifically, beforehand defined taxa. This might be achieved using either primers located in less conserved parts of the GTP-binding sites encoding regions or primers located in the GTP-sites enclosed region itself.

Usually, amplification is needed to enhance the subsequent hybridization signal. However for some samples or some organisms amplification might not be necessary. This might also be the case if, for the detection of the hybrids formed, highly sensitive signal-amplification systems are used.

Thirdly, after a denaturation step, the nucleic acids present in the sample or the resulting amplified product are contacted with LiPA strips onto which one or more DNA-probes are immobilized, allowing the detection of the organisms of interest, and hybridization is allowed to proceed.

Finally, after having performed a wash step, the hybrids are detected using a convenient and compatible detection system. From the hybridization signals or patterns observed the presence or absence of one or several organisms screened for in that particular biological sample can be deduced.

In a more particular embodiment, the invention provides for a method as described above, for detection of one or more thermophylic Campylobacter species, with said primer set comprising at least one set selected from the following sets of primers:

A: SEQ ID NO 24 and SEQ ID NO 32
B: SEQ ID NO 25 and (SEQ ID NO 33 and SEQ ID NO 34)
C: SEQ ID NO 26 and (SEQ ID NO 33 and SEQ ID NO 34)
and with said probes comprising least one of the sequences represented by SEQ ID NO 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70, or any oligonucleotide probe selected from any of the sequences represented by SEQ ID NO 1, 3, 4, 5, 6, 7, 8, 9, 10, 11, 12, 13, 14, 15, 16, 17, 18, 19, 20, 21, 22, 23 or 82 as long as said probe can be caused to hybridize specifically to DNA of thermophylic Campylobacter species, or variants of said probes, provided that said variants still hybridize specifically to the DNA of thermophylic Campylobacter species.

In a preferred embodiment, the invention provides for a method as described above, for detection of one or more thermophylic Campylobacter species, with said primer set comprising at least the following set of primers:

B: SEQ ID NO 25 and (SEQ ID NO 33 and SEQ ID NO 34) and with said probes comprising at least one of the sequences represented by SEQ ID NO 40, 42, 50, 51, 62, 64, 66, 68, 69, or 70.

In another embodiment, the invention provides for a method as described above, for detection of one or more veterinary Campylobacter species, with said primer set comprising at least the following set of primers:
B: SEQ ID NO 25 and (SEQ ID NO 33 and SEQ ID NO 34) and with said probes comprising at least one of the sequences represented by SEQ ID NO 71 to 79, or any probe derived from at least one of the sequences represented by SEQ ID NO 83 or 87.

The invention also provides for a method as described above, for detection and/oe differentiation of other species belonging to the genus Campylobacter, or belonging to other genera, in a biological sample, comprising at least one of the above-mentioned primers or probes.

In yet another particular embodiment the invention provides for a reverse hybridization method comprising any of the probes as described above, wherein said probes are immobilized on a known location on a solid support, more preferably on a membrane strip.

Other suitable assay methods for purposes of the present invention to detect hybrids formed between the oligonucleotide probes and the nucleic acid sequences in a sample may comprise any of the assay formats known in the art. For example, the detection can be accomplished using a conventional dot blot format, or by using sandwich hybridisation, competition hybridisation, strand displacement etc.

The invention also provides for a kit for detection and identification of at least one micro-organism, or the simultaneous detection and/or differentiation of several micro-organisms in a sample, comprising the following components:

(i) when appropiate, at least one suitable primer set as described above to allow amplification of part of the genomic DNA of said micro-organism(s), (ii) at least one of the probes as described above, (iii) a buffer, or components necessary to produce the buffer, enabling a hybridisation reaction between these probes and the nucleic acids present in the sample, or the amplified product.

(iv) a solution, or components necesary to produce the solution, enabling washing of the hybrids formed under the appropiate wash conditions, (v) when appropiate, a means of detecting the hybrids resulting from the preceding hybridisation.

In a more particular embodiment, the invention provides for a kit as described above for detection and/or differentiation of thermophylic Campylobacter species in a sample, wherein said primerset comprises at least one set selected from the following sets of primers:
A: SEQ ID NO 24 and SEQ ID NO 32
B: SEQ ID NO 25 and (SEQ ID NO 33 and SEQ ID NO 34)
C: SEQ ID NO 26 and (SEQ ID NO 33 and SEQ ID NO 34)
and wherein said probes comprise at least one of the sequences represented by SEQ ID NO 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70, or any oligonucleotide probe selected from any of the sequences represented by SEQ ID NO 1, 3, 4, 5, 6, 7, 8, 9, 10, 11, 12, 13, 14, 15, 16, 17, 18, 19, 20, 21, 22, 23 or 82 as long as said probe can be caused to hybridize specifically to DNA of thermophylic Campylobacter species, or variants of said probes, provided that said variants still hybridize specifically to the DNA of thermophylic Campylobacter species.

In a more particular embodiment, the invention provides for a kit as described above for detection and/or differentiation of veterinary Campylobacter species in a sample, wherein said primerset comprises at least the following set of primers:
B: SEQ ID NO 25 and (SEQ ID NO 33 and SEQ ID NO 34) and wherein said probes comprise at least one of the sequences represented by SEQ ID NO 71 to 79, or any oligonucleotide probe selected from any of the sequences represented by SEQ ID NO 83 or 87 as long as said probe can be caused to hybridize specifically to DNA of veterinary Campylobacter species, or variants of said probes, provided that said variants still hybridize specifically to the DNA of veterinary Campylobacter species.

FIGURE LEGEND

FIG. 1: Schematic representation of the organisation of the *Campylobacter jejuni* c-gtp-1 gene.
G1–G3–G4: regions corresponding to the GTP-binding sites, numbering according to Bourne et al., 1991.
Domain 1 and Domain 2: the 2 putative GTP-binding domains in the c-gtp-1 protein.
APS: autophosphorylation site
PRIBNOW: Pribnow consensus sequence
S&D: Shine and Delgarno consensus sequence
PCR fingerprint probe: 630 bp fragment isolated and described in Example 1
CR1: *C. jejuni* specific probe as described in example 1.
CR2, NCR1, NCR2: see Giesendorf et al. 1993
GTP-primerset: localization of the primersets used for amplification of a 160 bp fragment of the c-gtp-1 gene in thermophylic Campylobacter species as described in Example 1.

FIG. 2: c-gtp-1 gene of *Campylobacter jejuni*
Nucleic acid sequence of the full c-gtp-1 gene of *C. jejuni* (SEQ ID NO 1), and amino acid sequence of the corresponding protein (SEQ ID NO 2). Nucleic acid regions coding for the GTP-binding sites are boxed. The sequence corresponding to the 630 bp fragment of example 1 is delineated with arrows. GTP-binding domains 1 and 2 are also delineated. Pribnow and S&D sequences are underlined.

FIGS. 3–7: Amplification of the DNA of different thermophylic Campylobacter species using different primersets and different amplification conditions
lanes 1–33 and lanes 54–72: not relevant
lane 34: *Campylobacter lari* 70
lane 35: *Campylobacter lari* 79
lane 36: *Campylobacter jejuni* 87
lane 37: *Campylobacter upsaliensis* B542
lane 38: *Campylobacter upsaliensis* B572
lane 39: *Campylobacter upsaliensis* D391
lane 40: *Campylobacter upsaliensis* D432
lane 41: *Campylobacter upsaliensis* D457
lane 42: *Campylobacter jejuni* CW20
lane 43: *Campylobacter jejuni* CW31
lane 44: *Campylobacter jejuni* CW36
lane 45: *Campylobacter jejuni* CW38
lane 46: *Campylobacter jejuni* CW41
lane 47: *Campylobacter jejuni* (Inno nr 11284)
lane 48: *Campylobacter coli* 29
lane 49: *Campylobacter coil* 32
lane 50: *Campylobacter coil* 53
lane 51: *Campylobacter coli* 86
lane 52: *Campylobacter coli* 94 lane 53: *Campylobacter coil* (Inno nr 11283)

Figure 3A:
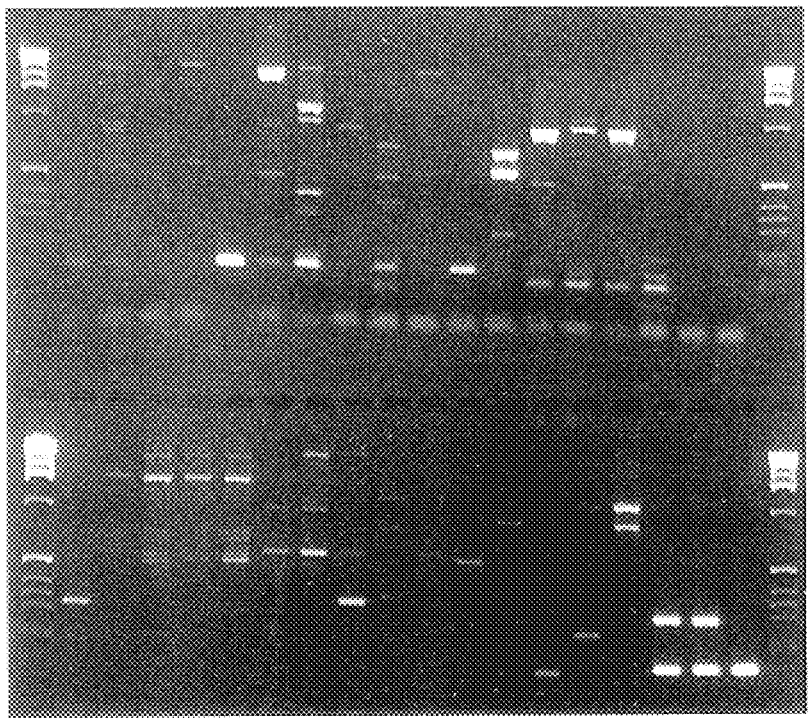
Figure 3B:
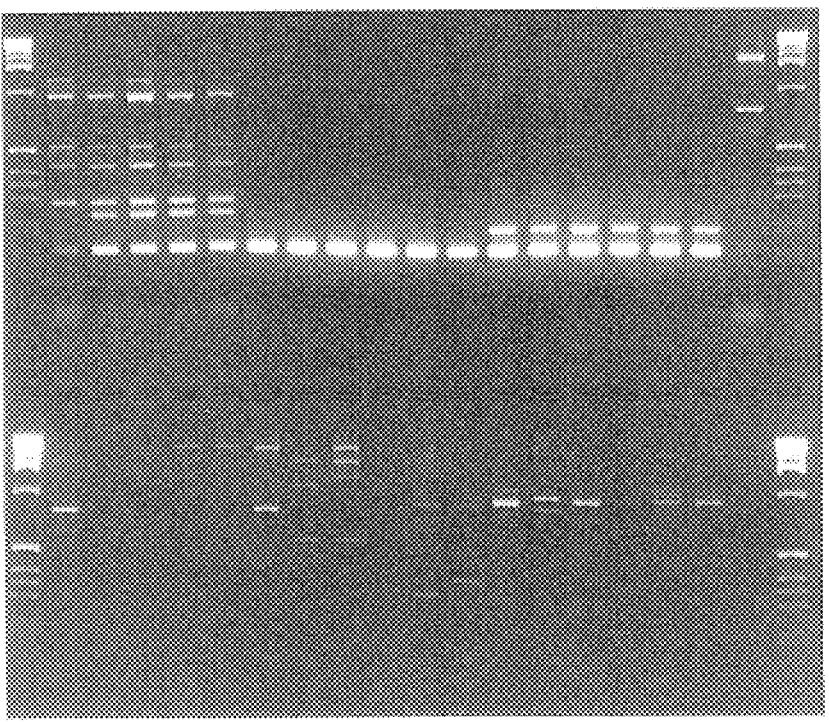
Figure 3C:
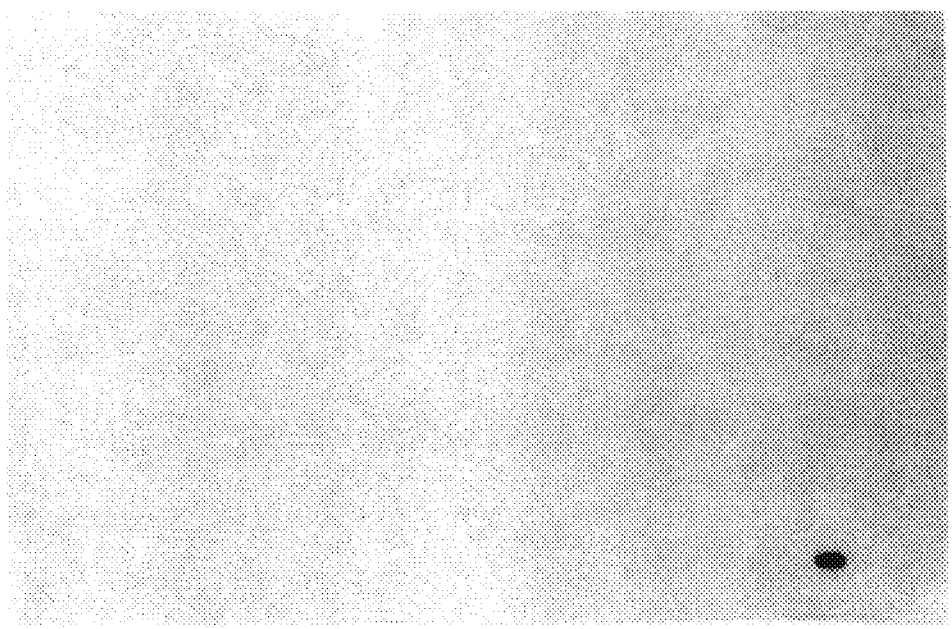
Figure 3D:
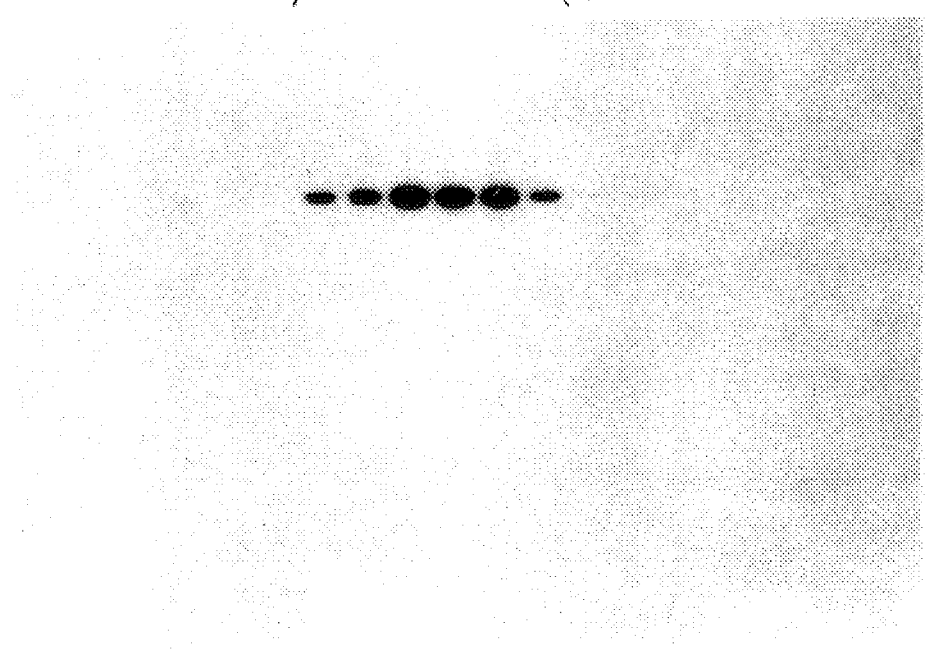

FIGS. 3A–3B: primerset A; annealing temperature: 50° C.
3a: agarose gel
3b: Southern blot of the gel in 3a using CR1 as a probe.

Figure 4A:
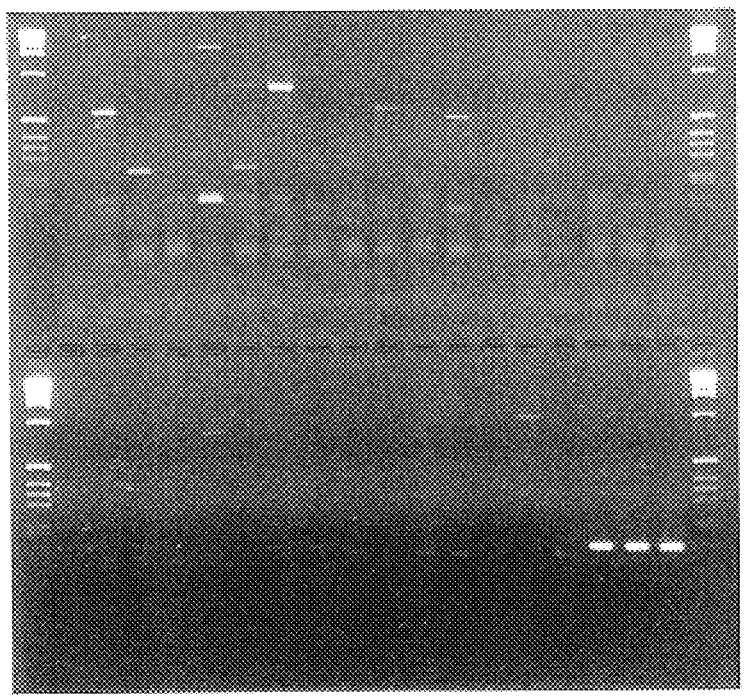
Figure 4B:
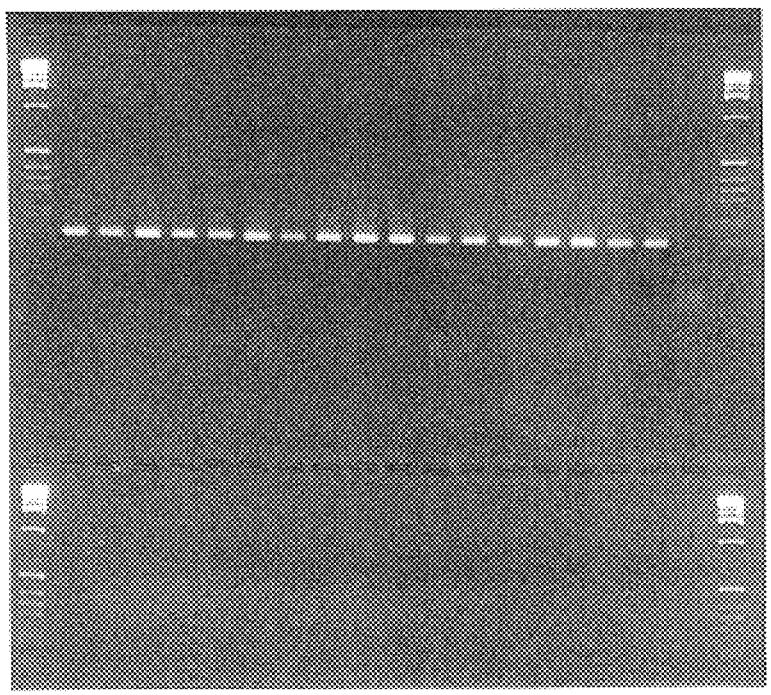

FIG. 4: primerset B; annealing temperature: 50° C., agarose gel

Figure 5A:
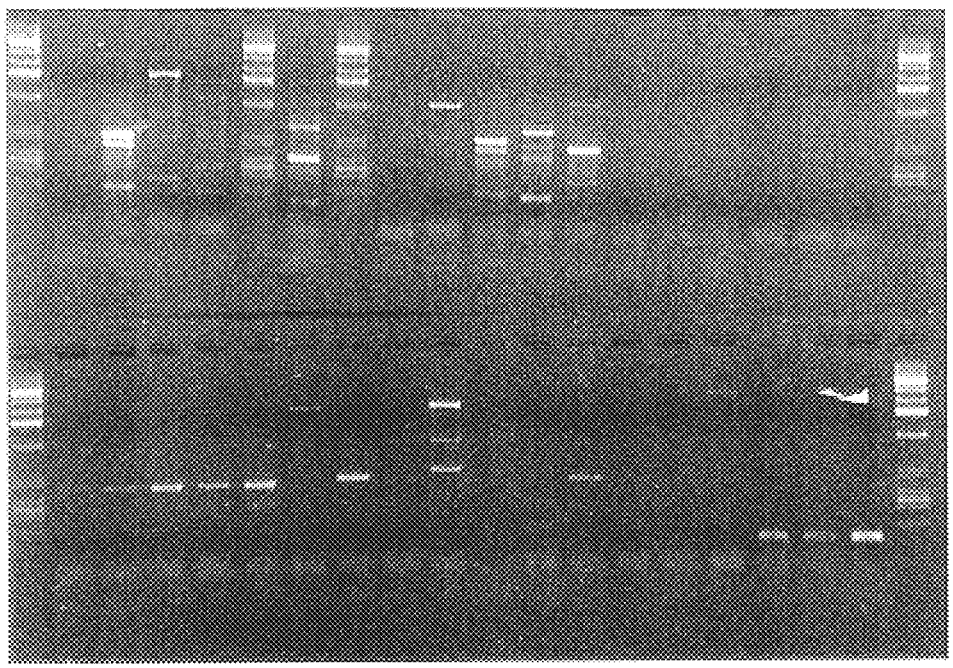
Figure 5B:
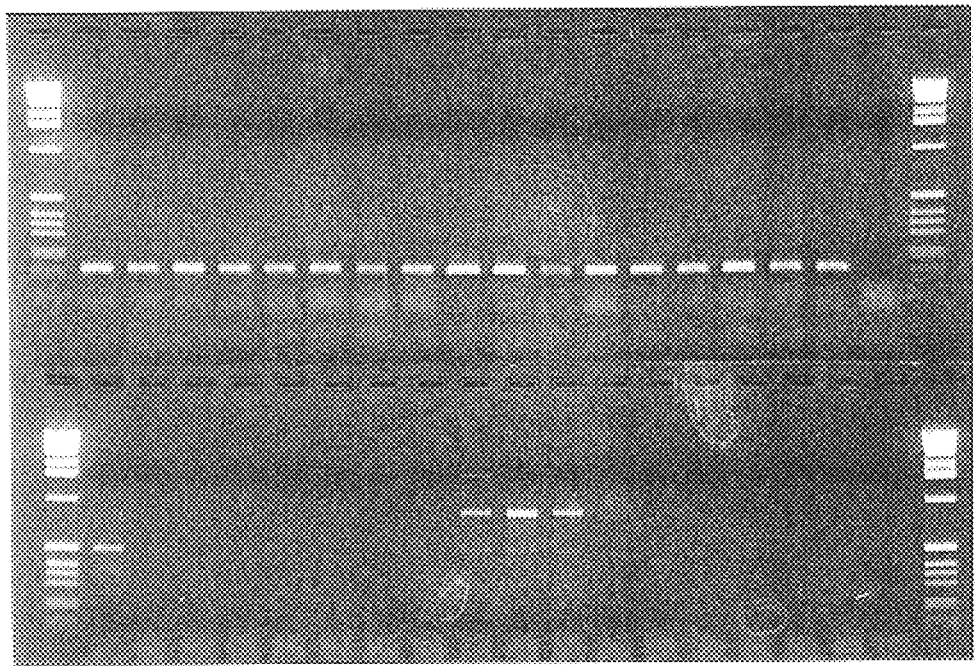

FIG. 5: primerset C; annealing temperature: 50° C., agarose gel

Figure 6A:
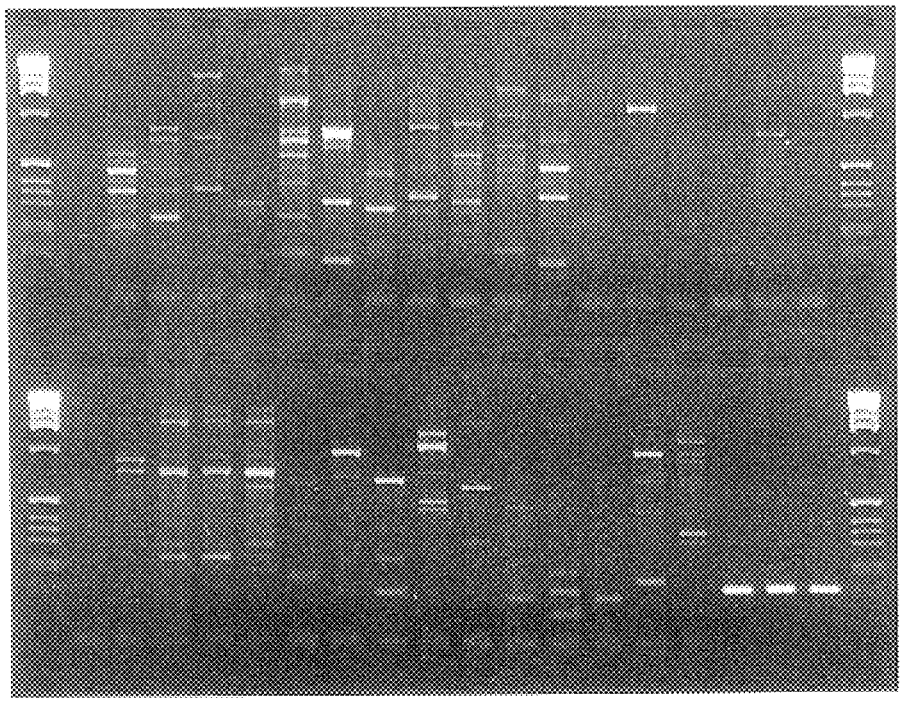
Figure 6B:
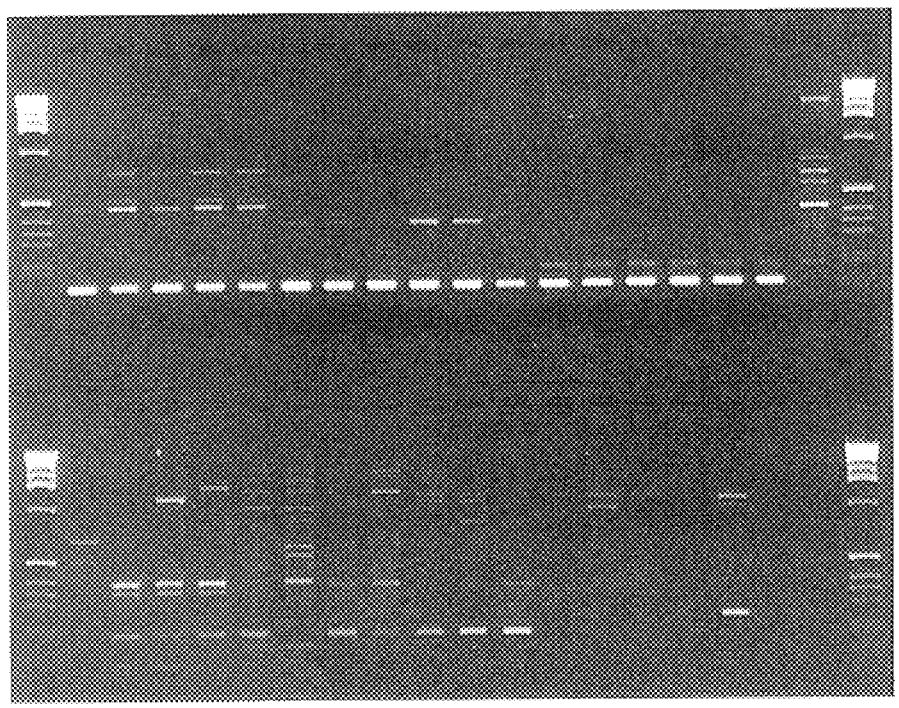

FIG. 6: primerset B; annealing temperature: 40° C., agarose gel

Figure 7A:
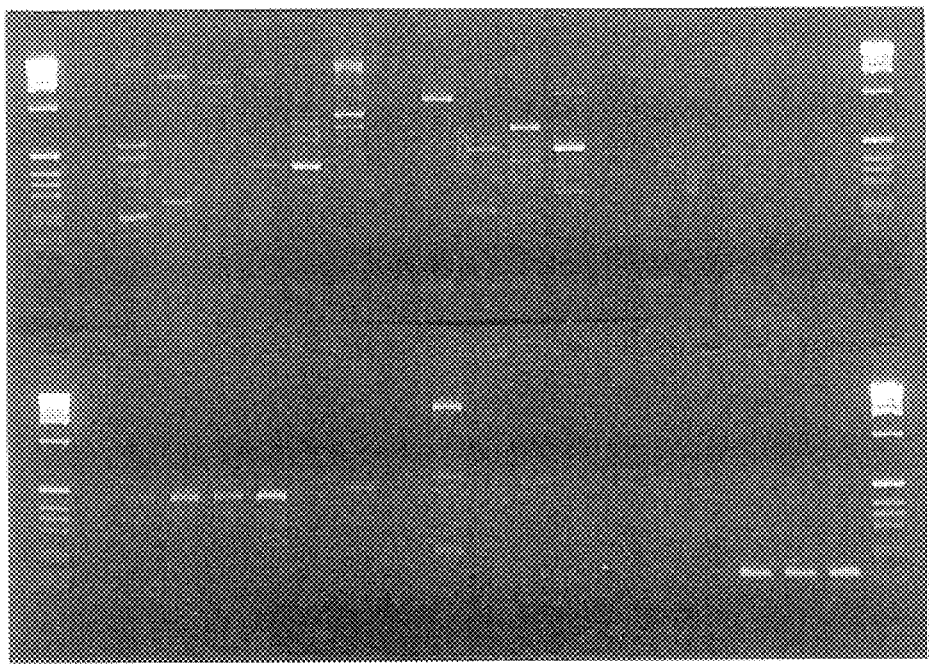
Figure 7B:
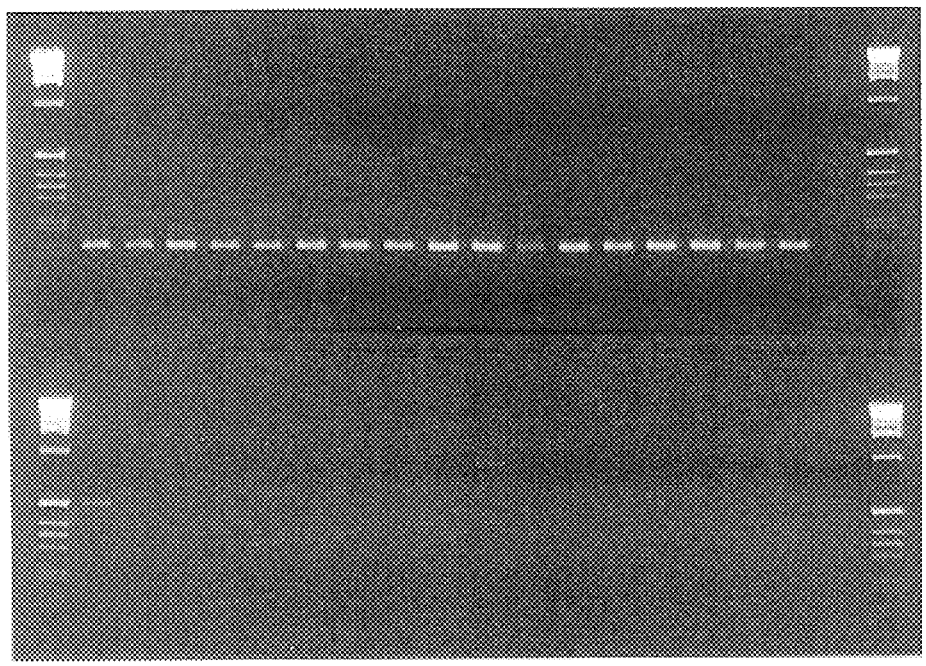

FIG. 7: primerset C; annealing temperature: 45° C., agarose gel

FIG. 8: Alignment of different GTP-sites enclosed regions from the c-gtp-1 gene family of different thermophylic Campylobacter species.

RINVSHORT: G1–G3 enclosed region from domain 1 of the c-gtp-1 gene of *C. jejuni* (SEQ ID NO 1, nucleot. pos 892to 1044)

SEQ ID NO 3–23: G1–G3 enclosed region from domain 1 of the c-gtp-1 gene of additional *C. jejuni* isolates (SEQ ID 3 to 10), of *C. coli* isolates (SEQ ID NO 11 to 16), of *C. lari* isolates (SEQ ID NO 17 to 21) and of *C. upsaliensis* isolates (SEQ ID NO 22 and 23), LIO numbers correspond to the ones in Table 2.

CJGTP2-13: =SEQ ID NO 82=G1–G3 enclosed region from domain 2 of the c-gtp-1 gene of *C. jejuni* (SEQ ID NO 1, nucleot. pos 1498 to 1608)

Figure 9:
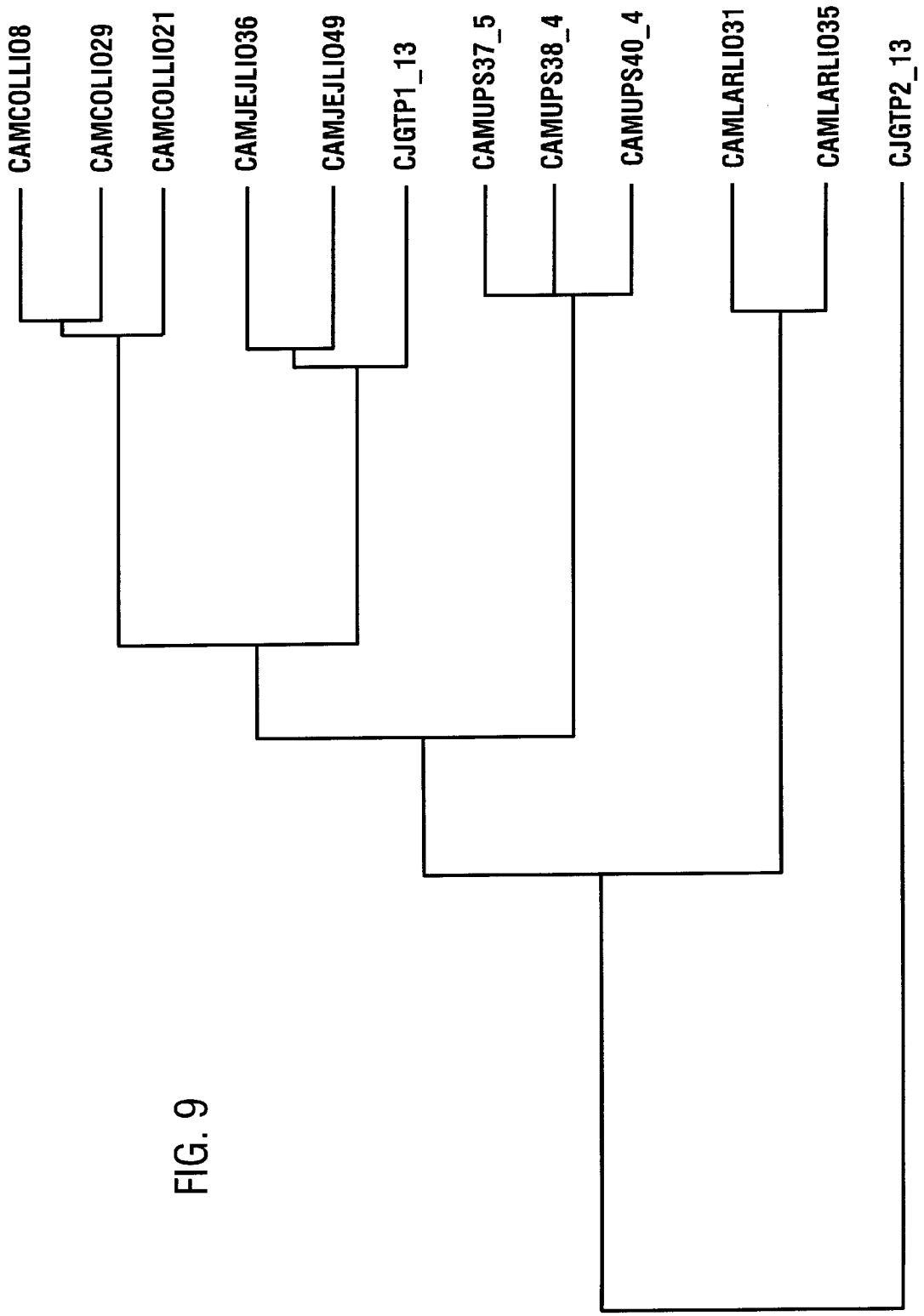

FIG. 9: Phylogenetic tree resulting from the alignment in FIG. 8.

cjgtp1__13=910–1026 from RINVSHORT.

Figure 10:
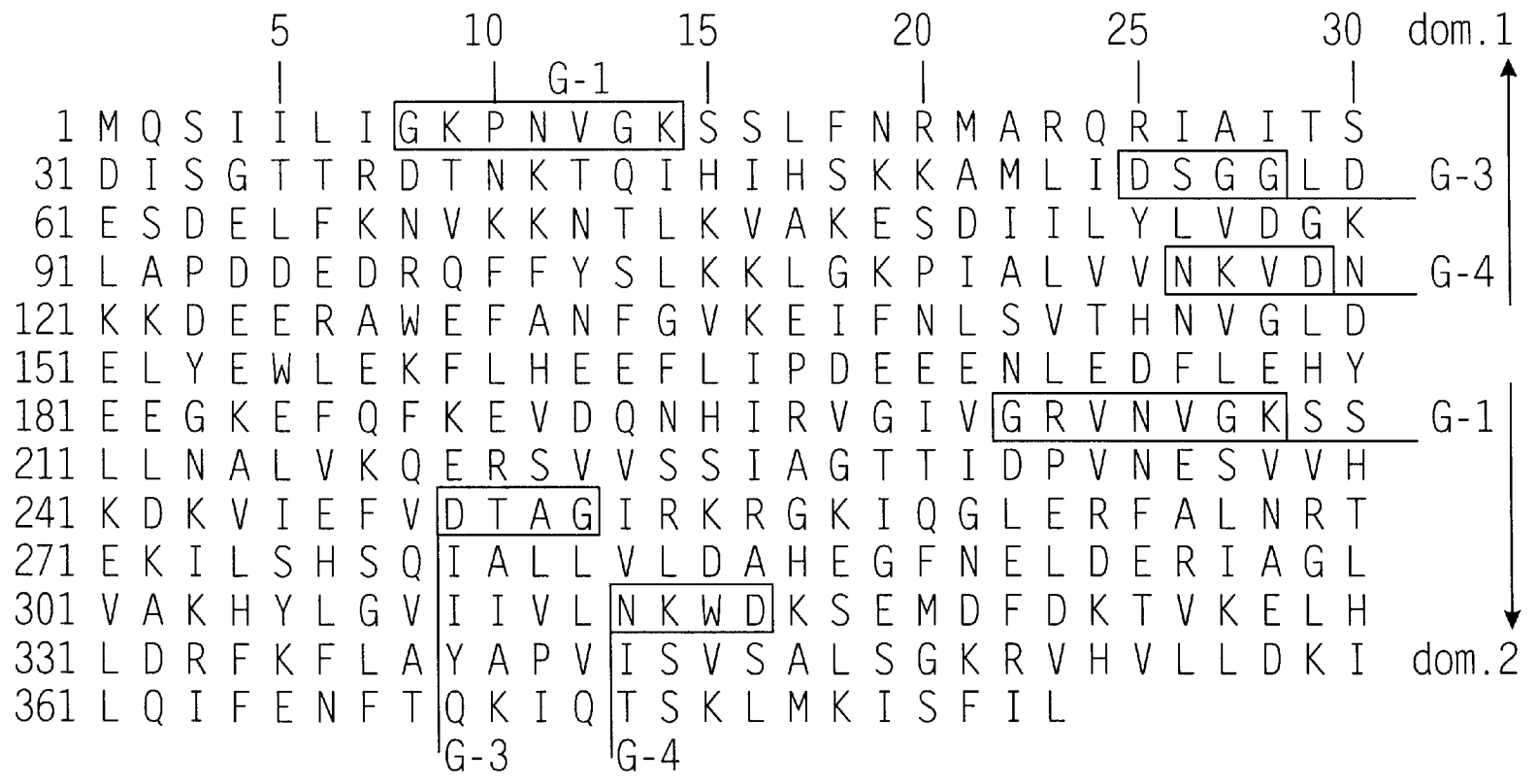

FIG. 10: Deduced amino acid sequence of the c-gtp-1 gene of *C. jejuni*. GTP-binding motifs from domain 1 and domain 2 are boxed. APS is underlined.

FIG. 11: Alignment of the deduced amino acid sequences from
(1) the c-gtp-1 gene of *C. jejuni*,
(2) a *Haemophilus influenzae* hypothetical protein HI0136 (Genbank access, No U32699)
(3) a *Mycobacterium leprae* hypothetical protein u0247e (Genbank access, No U00021).
"*" perfectly conserved residue
"." well conserved residue FIG. 12: Schematic representation of the alignment of FIG. 11.

Figure 13:
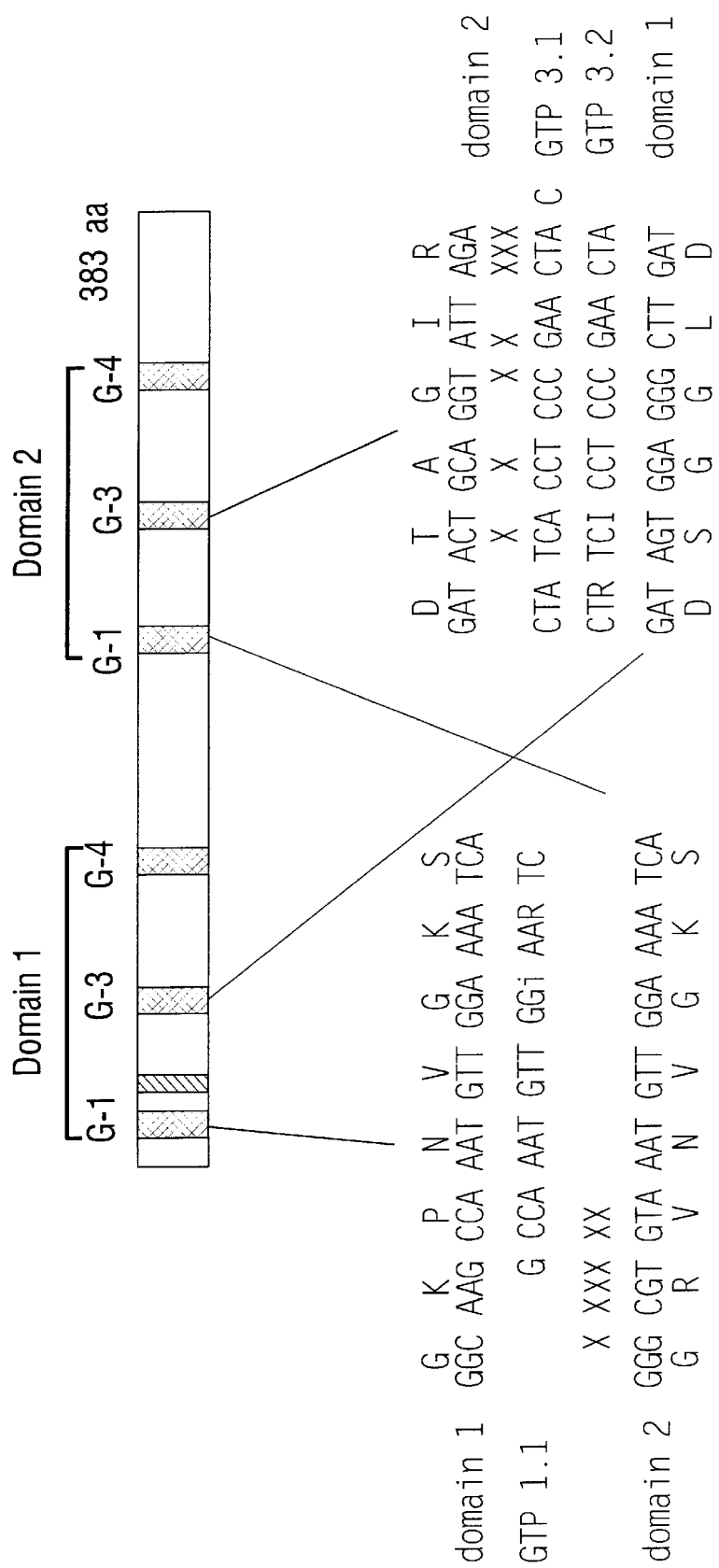

FIG. 13: Alignment of GTP-based primers as used in primerset B, with G-1 and G-3 sites from domain 1 and 2 of the c-gtp-1 protein of *C. jejuni*. Sequences of the GTP 3.1 and is GTP 3.2 primers are noted in the antisense direction (=reverse complements from the sequences in Table 3).

Figure 14:
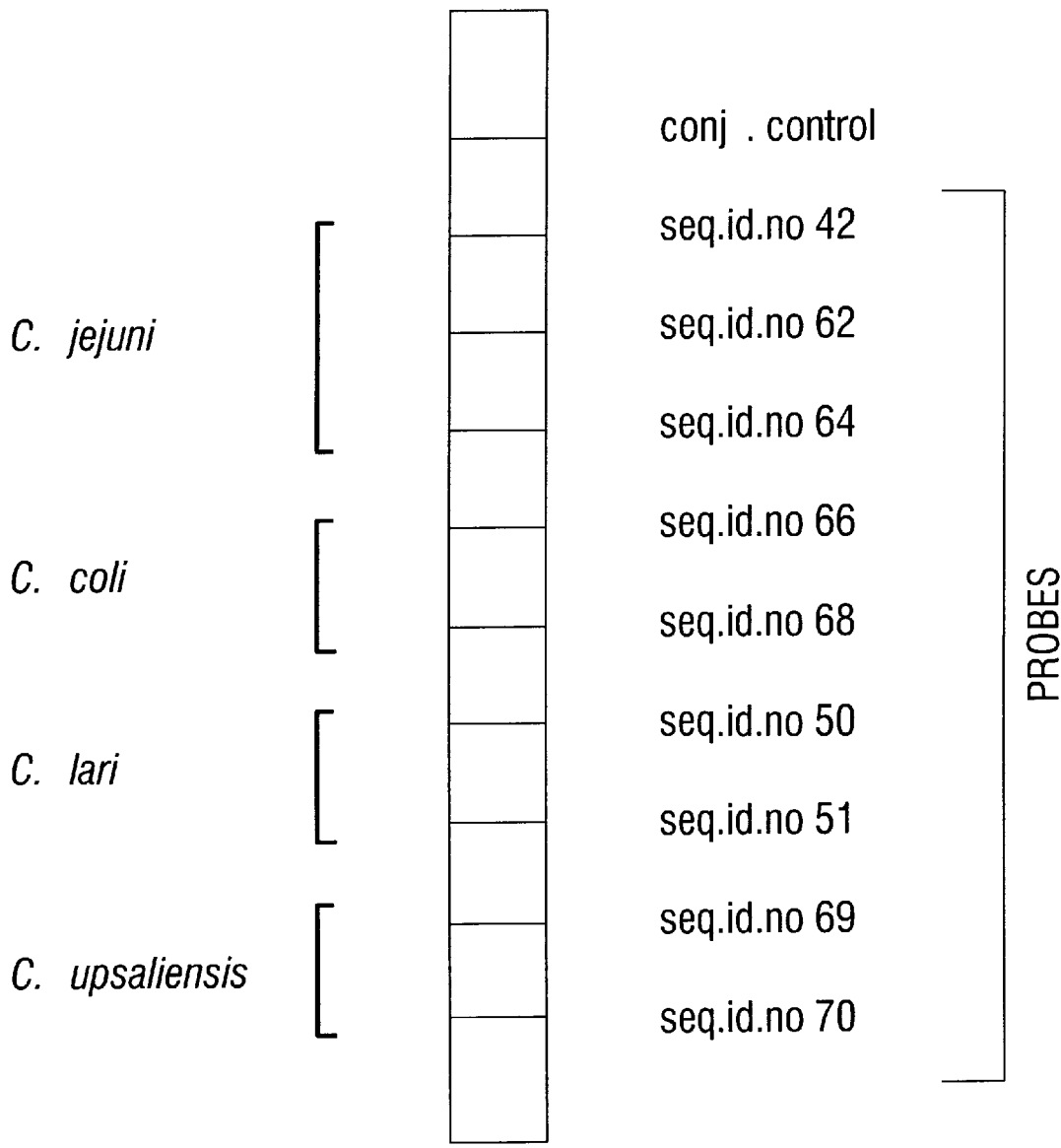

FIG. 14: Outline of a LiPA for differentiation of thermophylic Campylobacter species.

Figure 15:
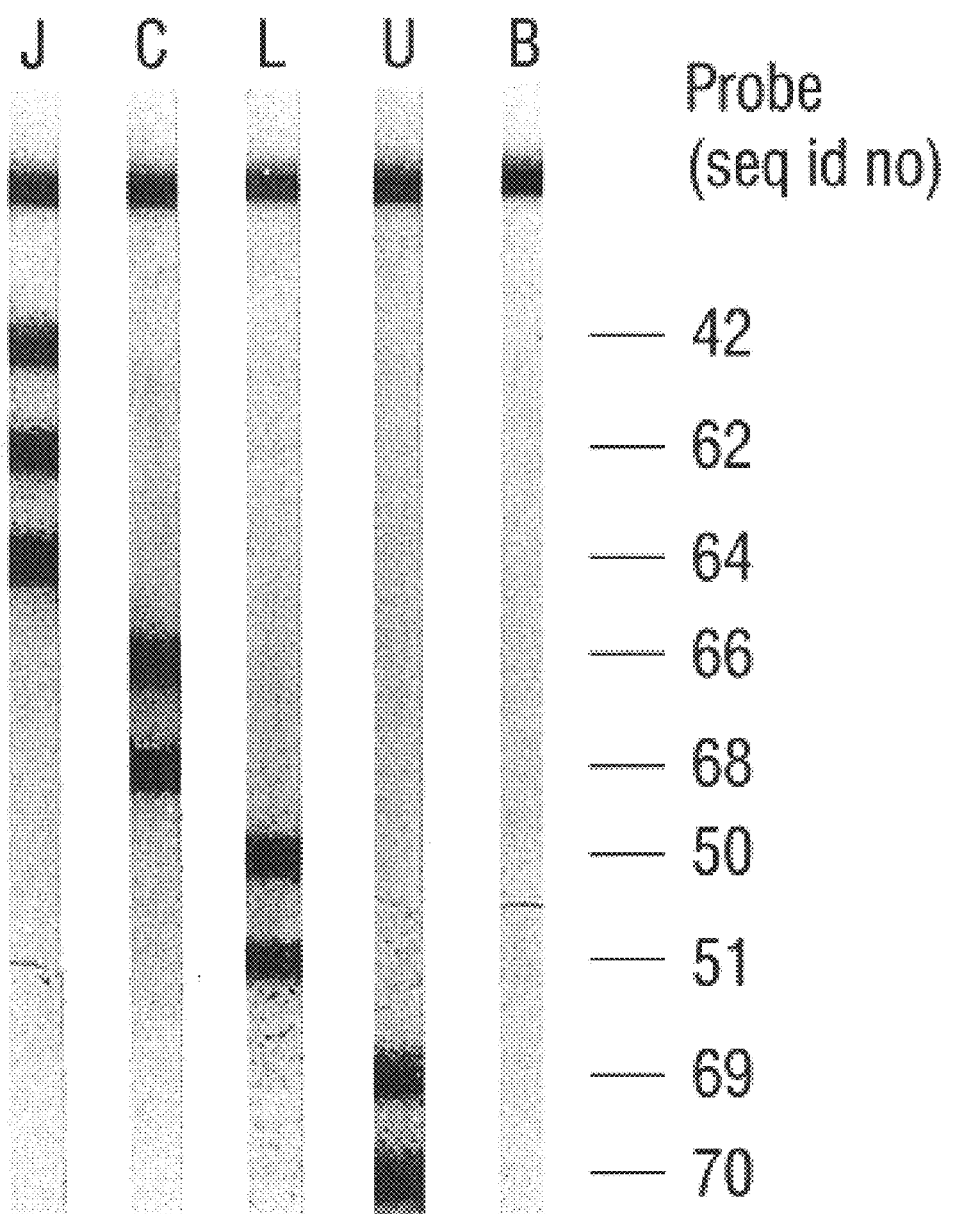

FIG. 15: Experimental results obtained with a LiPA as outlined in FIG. 14.
lane J=hybridized to *C. jejuni* amplified DNA
lane C=hybridized to *C. coli* amplified DNA
lane L=hybridized to *C. lari* amplified DNA
lane U=hybridized to *C. upsaliensis* amplified DNA
lane B=negative control lane FIG. 16: Alignment of c-gtp-2 gene fragments amplified with primerset B from different organisms:
"*": character which is perfectly conserved
".": character which is well conserved
C.fetus17__b=*Campylobacter fetus* LMG 6442
C.fetus__16=*Campylobacter fetus* ATCC 33246
C.fetus18__B =*Campylobacter fetus* LMG 6569
Crect7__13=*Campylobacter rectus* LMG 7614
Chyoi14__13=*Campylobacter hyointestinalis* LMG 9276

Acin=Acinetobacter spp. various clinical isolates, classified according to Tjernberg and Ursing (1989) by DNA-DNA hybridization (DNA group between brackets): Acin2627 (13), Acin2284 (13), Acin468 (3), Acin1163 (3), Acin45 (8), Acin548 (8), Acin 549 (8).

HI0393=G1–G3 enclosed region from *Haemophilus influenzae* hypothetical protein HI0393, Genbank accession number L45034

ECPTHGSH=G1–G3 enclosed region from *Escherichia coli* K12 hypothetical GTP-binding protein ECPTHGSH Genbank accession number X61941. Corresponding protein sequence, accession number P31316^Z FIG. 17: Alignment of the deduced amino acid sequences from the nucleic acid sequences in FIG. 16.

FIG. 18: *H. influenzae* c-gtp-2 like protein (HI0393) sequence retrieved from Genbank (accession number L45034), G-1 and G-3 like sequences are indicated.

EXAMPLES

Example I

Isolation and Sequencing of a 630 bp Fragment of the c-gtp-1 Gene of *Campylobacter jejuni*

Introduction

*Campylobacter jejuni* is an important cause of diarrhea and, at present, more frequently isolated from stool specimens than Salmonella spp. and Shigella spp. together (Skirrow and Blaser, 1992). This necessitates fast and sensitive detection methods for this organism.

The conventional differentiation between all species of the genus Campylobacter is based on biochemical tests, antimicrobial resistance patterns and optimal growth temperatures. The identification of all these Campylobacters can be difficult because strains have relatively fastidious growth requirements, are asaccharolytic, and only a limited number of biochemical tests provide adequate discrimination. For instance, the hydrolysis of hippurate which is normally used to distinguish *C. jejuni* from *C. coli*, is not completely reliable (Roop et al., 1984).

To allow more cost-effective and specific detection and identification of Campylobacter species, methods other than the conventional biochemical tests, such as latex agglutination tests (LATs) and procedures based on DNA homologies have been developed. The more powerful methods, based on DNA homologies, can be applied for both taxonomical classification of Campylobacter species, culture confirmation and detection in clinical material (Goossens and Butzler, 1992; Wesley et al., 1991). In the 1980's. several groups have developed DNA probes, some of which are based on the 16S rRNA, for colony typing (Picken et al., 1987; Korolik et al., 1987; Ezaki et al., 1988; Romaniuk and Trust, 1989; Zhou and Wang, 1989). These probe-based methods also have the disadvantage that their sensitivity, estimated at $10^5$–$10^7$ cfu/g faecal material, is relatively low and can lead to false-negative results for samples with a low infectious dose (Thorne et al., 1990; Taylor and Hiratsuka, 1990; Olive et al., 1990). Tenover et al. (1990) and Popovic-Uroic et al. (1991) evaluated the commercially available Accu Probe Assay System (Gen-probe Inc.) based on DNA probes labelled with acridinium esters, for confirmation of cultures from faecal samples. This system generated good results but unfortunately, the sensitivity of the assay was not estimated in these studies.

At present a few PCR assays for the detection of Campylobacter in food, environmental and clinical samples have been described. Oyofo et al. (1992) developed a PCR based on the 5' end of the flaA gene of *C. coli* VC167. Wegmüller et al. (1993) designed a PCR assay based on the intergenic sequence between the flagellin genes flaA and flaB. Stonnet & Guesdon (1993) developed a PCR test specific for *C. jejuni*, based on a DNA fragment isolated from a *C. jejuni* CIP70.2 cosmid library. Van Camp et al. (1993) used the 16S rRNA gene and described a PCR assay that could not discriminate between the different thermophilic Campylobacter species. Eyers et al. (1993), however, developed a Campylobacter species-specific PCR assay based on the region located between helices 43 and 69 of the 23S rRNA.

The polymerase chain reaction (PCR) can also be used for genetic fingerprinting by random selection of primer annealing sites (Jayarao et al., 1992; Mc Millin and Muldrow, 1992; Walsh and Mc Clelland, 1991). These primer binding sites are distributed throughout the entire genome and amplification generates DNA fragments which differ in length. Numerous examples of this so-called PCR fingerprinting for determining relationships among strains and species of microorganisms have been published (for a review see Van Belkum, 1994).

For Campylobacter spp., PCR fingerprinting has been used in epidemiological studies of *C. jejuni* and *C. upsaliensis* (Giesendorf et al., 1994). Besides the generation of isolate-specific fragments, also species-specific fragments were selected that could be used as DNA probes on Southern blots containing genomic DNA from Campylobacter spp. and other microorganisms (Giesendorf et al., 1993). This species-specificity indicated the presence of unique sequences in the selected probe fragments.

One such fragment, selected for *C. jejuni*, was further characterised. The DNA fragment was cloned, the nucleic acid sequence was determined and similarity to known sequences was investigated. The fragment contained an open reading frame (ORF) coding for the N-terminal part (95 amino acids) of a protein. Screening of the Swiss protein library with the 95 amino acid sequence deduced from the ORF indicated similarity to the *Escherichia coli* Ras-like (Era) protein, a protein containing three GTP-binding sites (Ahnn et al., 1986). Similarity was highest at two possible GTP-binding sites present in the probe fragment. PCR primers, based on the GTP-binding sites, were used to investigate the conserved nature of these sites in other Campylobacter species. Furthermore, the nucleic acid sequence of the region flanked by the GTP binding sites (GTP-sites enclosed region) was determined in order to investigate the possibility to develop species-specific probes selected from this region.

Materials and Methods

Bacterial strains. Reference serotype strains of *Campylobacter jejuni, C. coli* and *C. lari*, used for DNA sequencing of the GTP-sites enclosed region, were obtained from H. Goossens (University Hospital Antwerp, Belgium), Strains were biotyped and serotyped according to Lior's scheme (Lior et al., 1982; Lior, 1984). A survey is presented in Table 2. *Campylobacter upsaliensis* strains used for sequencing were isolated from stool specimens of patients (St. Pieters Hospital, Brussels, Belgium).

A variety of other, non-reference Campylobacter strains were used for evaluating the PCR amplification reaction with different sets of primers (cfr. FIGS. 3–7). These strains were obtained from the Diagnostic Centre SSDZ, Delft, The Netherlands; the state Institute for Quality Control of Agricultural Products (RIKILT-DLO), Wageningen, The Netherlands; the National Institute of Public Health and Environmental Production (RIVM), Bilthoven. The Netherlands; the American Type Culture Collection (ATCC), Rockville Md. USA; the National Collection of Type Cultures (NCTC), London, England; the Culture Collection of the Laboratory for Microbiology, Ghent (LMG). Belgium; and the Slotervaart Hospital, Amsterdam, The Netherlands.

DNA isolation. DNA was isolated from pure cultures by standard procedures as described before (Giesendorf et al. 1993). After ethanol precipitation, the concentration of the DNA solution was estimated by electrophoresis on a 1% agarose gel in comparison with known amounts of lambda DNA as reference.

Isolation, cloning and sequence analysis of the *C. jejuni* specific fragment. The *C. jejuni* specific fragment was obtained after amplification of *C. jejuni* DNA with primers REP1R-1 and REP-2 as described before (Giesendorf et al., 1993). After electrophoresis the fragment was excised from the gel and purified by the Geneclean kit (Bio 101, La Jolla, Calif.). The purified 630 bp fragment was cloned into plasmid pGEM-T (Promega) which was transformed into *Escherichia coli* JM109. Sequence analysis was performed using the Pharmacia T7 sequencing system (Pharmacia, Uppsala, Sweden) using.[$^{35}$S]-dATP (Amersham). Gels were dried oil a Biorad vacuum gel dryer model 583 and exposed to Cronex 4 films (Dupont) at room temperature for 24–48 h. Sequence analysis was performed with the PCGene software (Intelligenetics, Mountain View, Calif., USA).

PCR. The PCR reaction mixtures (total volume of 100 µl) consisted of 10 mM Tris-HCl (pH 9.0), 50 mM KCl, 2.5 mM $MgCl_2$, 0.01% gelatin and 0.1% Triton X-100. Deoxyribonucleotide triphosphates were used at a final concentration of 0.2 mM. Per reaction, 0.25 U Super Taq DNA polymerase (Sphaero Q, Leiden, The Netherlands) was added.

Primers based on the GTP-binding sites. G-1 and G-3, and degenerated primers based on G-1 and G-3, were used (Table 3). Three different PCR programmes were used which involved 40 cycles of consecutive denaturation (1 min 94° C.), primer annealing (1 min 50° C. 45° C. or 40° C. for the three different programmes, respectively) and chain extension (1 min 74° C.). A Biomed thermocycler model 60 (Biomed. Germany) was used in all experiments. Primers were used at a concentration of 50 pmol per reaction. The following primersets were used: A. GTP3+GTP1, B. GTP1.1+(GTP3.1+GTP3.2); and C. GTP1.2+(GTP3.1+GTP3.2) (see Table 3).

Sequence analysis of the PCR fragments. After separation of PCR products, generated with primers GTP-3 and GTP-1, on a 2% low melting point agarose gel the DNA fragment of approximately 150 bp was excised from the gel and dissolved in 250 µl binding and washing buffer (B&W: 10 mM Tris-HCl (pH 7.5) 1 mM EDTA, 2 M NaCl) and 50 µl Dynabeads M-280 Streptavidin (Dynal) in B&W buffer (10 mg/ml) at 65° C. for 15 min. The beads were washed once with B&W buffer at 65° C. once with B&W buffer at room temperature and once with 10 mM Tris, 0.1 mM EDTA pH 7.5 (TE). Next, the beads were incubated with 50 µl 0.1 N NaOH, 10 min at room temperature, for denaturation of the DNA. The supernatant was transferred to a new tube and DNA was precipitated with 5 µl 3M NaCl, 1 µl polyA (20 mg/ml) and 100 µl 96% ethanol. After centrifugation for 10 min at 12000 g, the pellet was washed twice with 1 ml 70% ethanol, dried, suspended in 20 µl TE and stored at −20° C. for sequencing.

The beads were washed once with 50 µl 0.1 NaOH and twice with 100 µl TE. Finally the beads were suspended in 20 µl TE. Ten µl were used for sequence analysis using the Pharmacia T7 Sequencing Kit.

Results

Sequence determination of the 630 bp *C. jejuni* specific fragment. Three independent clones containing the *C. jejuni* specific 630 bp fragment were sequenced. No differences between the sequences obtained from these clones were found. The sequence of the 630 bp fragment is delineated with arrows in FIG. 2 (nucl. pos. 521 to 1149).

The following nucleotide sequence databases were screened for sequences homologous to the selected *C. jejuni* specific fragment: PDB (Brookhaven Protein Data Bank, April 1994)+GBUpdate (GenBank cumulative daily updates to EMBLUpdate+EMBL). GenBank vector (Vector subset of Genbank, April 1994)+repbase (Human and other primers Alu repeats, June 1994)+alu (select Alu repeats from REPBASE)+kabatnuc (Kabat Sequences of Nucleic Acid of Immunological Interest, August 1992)+epd (Eukaryotic Promotor Database Release 35, June 1993)+dbest (Database of Expressed Sequence Tag Release 2.29. August 1994)+dbst (Database of Sequenced Tags Sites Release 1.3. August 1994). No significant homologies were found.

Furthermore, the fragment sequence was screened for the presence of one or more ORFs. The start of an ORF was identified with an ATG initiation-codon (see position 865 on FIG. 2) and upstream of the ATG codon a sequence homologous to the 16S rRNA binding site consensus sequence (5' AGGAAA 3', position 856 on FIG. 2). Furthermore, a sequence homologous to the Pribnow consensus sequence also seems to be in a correct position (5'TATAAT 3', position 845 on FIG. 2).

The following peptide sequence databases were screened for similarities to the 95 amino acid sequences deduced from the ORF, using the BLASTP 1.3.13MP (June 1994) software (4.59); PDB (Brookhaven Protein Data Bank, April 1994)+ SwissProt (Release 29.0, June 1994)+PIR (Release 41.0, June 1994)+spupdate (SwissProt cumulative weekly update)+genpept (CDS translations from GenBank (R) Release 84.0, August 1994)+gpupdate (cumulative daily updates to the major release of genpept)+kabatpro (Kabat Sequences of Proteins of Immunological Interest Release 5.0, August 1992)+TFD (TFD transcription factor (protein) database Release 7.0, June 1993)+acr (Ancient Conserved Region subset of Swiss-Prot, December 1993)+alu (Translation of select Alu repeats from REPBASE). Some similarity was found with the *Escherichia coli* Ras-like (Era) protein, a protein containing three GTP binding sites (Ahnn et al., 1986). Similarity was highest at two putative GTP binding sites present in the fragment, located in the corresponding polynucleic acid sequence between positions 886–906 and 1027–1038 respectively (see FIG. 1 (G-1 and G-3) and FIG. 2). the rest of the protein showed no substantial homology.

Development of the GTP-PCR. Primers based on the GTP-binding sites G-1 and G-3 from the 630 bp fragment were selected: primers GTP-1 and GTP-3 (Table 3). Also degenerate primers, based on G-1 and G-3 were designed. Several primer combinations were evaluated on DNA from a selection of thermophylic Campylobacter strains at different annealing temperatures. The results are represented in FIGS. 3–7. The sequences of the primers and primer combinations are represented in Table 3.

Primersets B and C yielded a single PCR product of approximately 150 bp for each of the Campylobacter isolates at an annealing temperature of 50° C., whereas primerset A resulted in a more complex pattern with additional DNA fragments at the same annealing temperature. Lower annealing temperatures resulted in less specific amplification, or more complex patterns.

Sequence alignment of the GTP-sites enclosed region from the different Campylobacter species, and selection of species-specific probes. After amplification with primers GTP-1 and GTP-3, the nucleic acid sequence of the region enclosed by G-1 and G-3 from a selection of Campylobacter reference strains was determined as described in Material and Methods. FIG. 8 shows the sequence alignment of the region enclosed by G-1 and G-3 from several strains belonging to the following thermophylic Campylobacter species: *C. jejuni, C. coli, C. lari* and *C. upsaliensis*. A high degree of sequence variation between the different species is present whereas only few differences were found within a species. This enabled the design of a variety of species-specific probes from the GTP-sites enclosed region. for the different thermophylic Campylobacter species mentioned above, and also a probe specific for the group of thermophylic Campylobacter species. Among others, the following probe sequences can be used for the specific identification of the following Campylobacteria: general probe for thermophylic Campylobacteria:

SEQ ID NO 40: ACWAGAGATACMAATAAAA
specific probes for *C. jejuni:*
SEQ ID NO 41: CAGGTACAACTAGAGATACA (=CR1-probe described in Example 1)
SEQ ID NO 42: TTAATAGAATGGCAAGACAA
SEQ ID NO 61: TTTTTAATAGAATGGCAAGAC
SEQ ID NO 62: CTTTTTAATAGAATGGCAAGACAAAG
SEQ ID NO 43: TAGAATGGCAAGACAAAGAA
SEQ ID NO 44: ATATTTCAGGYACAACTAGA
SEQ ID NO 45: ATTCAAAAAAAGCCATGCTT
SEQ ID NO 63: CATTCAAAAAAAGCCATGCTT
SEQ ID NO 64: TTCATATTCATTCAAAAAAAGCCATGCTT
specific probes for *C. coli:*
SEQ ID NO 46: TCAAGTTTATTTAACAGAAT
SEQ ID NO 65: ATCAAGTTTATTTAACAGAATGG
SEQ ID NO 66: ATCAAGTTTATTTAACAGAATGCAAG
SEQ ID NO 47: AAATTTCAGGTACTACAAGA
SEQ ID NO 48: TAAAACAGAAGTTTTTATAA
SEQ ID NO 67: CAATAAAACAGAAGTTTTTATAA
SEQ ID NO 68: CCAATAAAACAGAAGTTTT-TATAAATTC
specific probes for *C. lari:*
SEQ ID NO 49: CTTTTTAATAGACTTGCAAG
SEQ ID NO 50: GACTTGCAAGAAAGCGCATA
SEQ ID NO 51: ACATAAGTGGAACCACAAGA
SEQ ID NO 52: TCACCAGTGACATAAGTGGA
SEQ ID NO 53: TGGAACCACAAGAGATACCA
SEQ ID NO 54: TGATGGCAAAAAAGCCTTGC
SEQ ID NO 55: GCATAGCTATCACCAGTGAC
SEQ ID NO 56: CAATAAAATAGAAGTACAAA
specific probes for *C. upsaliensis:*
SEQ ID NO 57: CGCATAGCAAGGCAAAGAAT
SEQ ID NO 69: TAATCGCATAGCAAGGCAA
SEQ ID NO 58: TTTCAGGCACGACTAGAGAT
SEQ ID NO 59: CAATGGTAAAGAAGCCTTGC
SEQ ID NO 70: TATCAATGGTAAAGAAGCCTT
SEQ ID NO 60: AAGAATCGCCATCACAAGTG The probe sequences were selected such that there are a minimum of 2 mismatches with respect to the target sequences of other organisms. It is known to the man skilled in the art that, under appropiate hybridization and wash conditions, even 1 mismatch between probe and target sequence can be reliably detected. Hence all probes specified should be able to discriminate homologous target sequences from non-homologous target sequences. By way of an example, the results obtained with one these probes (SEQ ID NO 41) are discussed below. A further evaluation of these probes in a reverse hybridization assay can be found in Example IV.

Hybridization results with probe CR1. After PCR, using primerset A and annealing temperature 50° C., and agarose gel electrophoresis, the fragments were blotted onto a membrane and hybridized with probe CR1.

The hybridisation medium consisted of 5×SSC, 5×Dernhardt's solution, 5 mM EDTA, 0.5% SDS, 0.1 mg/ml herring sperm DNA. The specific activity of the labelled CR1-probe used was $10^6$ counts/ml. The hybridisation temperature was 42° C. and hybridisation was carried out overnight (16 u). Washing occurred also at 42° C. (15 min) in a medium consisting of 2×SSC and 0.1% SDS.

Species-specificity for the CR1-probe for *C. jejuni* (SEQ ID NO 41) is demonstrated in FIG. 3*b,* lanes 36 and 42–47. Those *C. jejuni* isolates showing a weaker hybridization contain a single mismatch to CR1 (see also alignment FIG. 8).

The above-demonstrated "thermophylic Campylobacter"—universal nature of the primers derived from the GTP-binding sites, combined with the species-specificity of the above-mentioned probes, allows the development of a rapid and reliable assay, consisting of the simultaneous amplification of DNA from different Campylobacter species, followed by the hybridization of the amplified fragment to a set of species-specific probes. This assay would be extremely useful for Campylobacter diagnostics in clinical, environmental and food samples.

TABLE 2

Campylobacter reference serotype strains used in this study

| Biotype | Serovar | Strain | Source |
| --- | --- | --- | --- |
| *C. jejuni* I | LIO4 | 1/NCTC 11168 | Human |
| *C. jejuni* III | LIO30 | 1215/A 1616 | Human |
| *C. Jejuni* III | LIO61 | 5778/AP 39849 | Human |
| *C. jejuni* III | LIO38 | 2418/Y 438 | Human |
| *C. jejuni* II | LIO36 | 2074 | Human |
| *C. jejuni* I | LIO39 | 3238/AP 14R81 | Human |
| *C. jejuni* II | LIO49 | 3235/AP 11R81 | Human |
| *C. jejuni* II | LIO23 | 720 | Human |
| *C. jejuni* I | LIO28 | 1180 | Human |
| *C. jejuni* I | LIO7 | 35 | Human |
| *C. jejuni* II | LIO16 | 728 | Human |
| *C. coli* I | LIO8 | 52 | Human |
| *C. coli* II | LIO29 | 1982/SL 11 | — |
| *C. coli* II | LIO78 | 8681/FR 119 | Human |
| *C. coli* I | LIO21 | 699 | Chicken |
| *C. coli* II | LIO24 | 1213/PC 349 | Human |
| *C. coli* I | LIO80 | 8723/PERU PT 0412 | Chicken |
| *C. coli* I | LIO47 | 3067/CA 72 | — |
| *C. coli* I | LIO12 | 264 | Human |
| *C. lari* I | LIO31 | 729 | Human |
| *C. lari* I | LIO35 | 1728/MBS 25428 | Sea gull |
| *C. lari* I | LIO73 | 8351/HAM 17735 | Human |
| *C. lari* I | LIO64 | 5181/MBS 25453 | Sea gull |
| *C. lari* I | LIO56 | 3331/BC 1135 | Human |

TABLE 3

Primers and primersets derived from the GTP-binding sites of the c-gtp-1 gene of *Campylobacter jejuni*. All primer sequences are shown from 5' to 3' in the sense direction. It should be stressed however that these primers can be used both as sense or as anti-sense primers. In the latter case, the sequences as shown here should be converted to the reverse complement.

G-1 site primers

| GTP1 | CCAAATGTTGGAAAATCA | SEQ ID NO 24 |
| --- | --- | --- |
| GTP1.1 | GCCAAATGTTGGiAARTC | SEQ ID NO 25 |

TABLE 3-continued

Primers and primersets derived from the GTP-binding sites of the c-gtp-1 gene of *Campylobacter jejuni*. All primer sequences are shown from 5' to 3' in the sense direction. It should be stressed however that these primers can be used both as sense or as anti-sense primers. In the latter case, the sequences as shown here should be converted to the reverse complement.

| GTP1.2 | AAiCCAAATGTTGGiAAR | SEQ ID NO 26 |
| --- | --- | --- |
| GTP1.3 | GGCAAiCCAAATGTiGG | SEQ ID NO 27 |

G-3 site primers

| GTP3 | GATAGTGGAGGGCTTGAT | SEQ ID NO 32 |
| --- | --- | --- |
| GTP3.1 | GAYAGiGGAGGGCTTGAT | SEQ ID NO 33 |
| GTP3.2 | GAYAGiSSAGGiCTiGAT | SEQ ID NO 34 |
| GTP3.3 | GGGCTTGATGAAAGTGAT | SEQ TD NO 35 |

G-4 site primers

| GTP4 | AATAAAGTAGATAATAAAAAA | SEQ ID NO 80 |
| --- | --- | --- |
| GTP4.1 | AAYAARGTIGRIAAYAAAAAA | SEQ ID NO 81 |

Y = T or C
R = G or A
S = G or C
i = inosine

Possible primersets:

A: GTP1 + GTP3
B: GTP1.1 + GTP3.1 + GTP3.2
C: GTP1.2 + GTP3.1 + GTP3.2
D: GTP1.3 + GTP3.1 + GTP3.2
E: GTP1.1 + GTP3.3
F: GTP1.2 + GTP3.3

Example II

Isolation and Characterization of a Genomic DNA Fragment from *Campylobacter jejuni* Encoding the c-gtp-1 Protein Isolation of Homologous Genomic Clones In order to obtain the complete coding sequence of the c-gtp-1 protein, a putative GTP-binding protein of *Campylobacter jejuni,* part of which has been described in Example I, a genomic library of *Campylobacter jejuni* (described in Nuijten et al., 1990; kindly provided by prof. dr. B. A. M. van der Zeijst, University of Utrecht, the Netherlands), was screened with the 630 bp fragment described in Example I as a probe. This fragment was derived from *Campylobacter jejuni* genomic DNA by standard protocols (Sambrook et al., 1989). Screening of approximately 500,000 independent clones led to the isolation of several clones that showed strong hybridization to the 630 bp probe. Two clones were subjected to sequence analysis. A total sequence of 2047 bp was obtained (FIG. 2).

Characterization of the Genomic DNA Fragment

The 630 bp probe fragment is homologous to sequences between position 521 and 1149. Sequences showing homology to the REP1R-I (5'-iiiiCGUCGUCATCiGGC-3') and REP-2 (5'-iCGiCTTATCiGGCCTAC-3') primers, that were used to amplify the 630 bp fragment by PCR fingerprinting, are located between nucleotide positions 521–540 and 1139–1150, respectively.

The following datalibraries were screened for nucleotide sequences homologous to the 2047 bp sequence as shown in FIG. 2 by the Experimental GENINFO (R) BLAST Network Service (Blaster).

PDB (Brookhaven Protein Data Bank, April 1994 release)
Genbank (R) release 90, August 1995.
GBUpdate (GenBank cumulative daily updates)
EMBL Data Library release 43.0, June 1995.
EMBLU (EMBL Data Library cumulative daily updates)
GenBank vector (Vector subset of Genbank, February 1995)
alu (select Alu repeats from REPBASE)
kabatnuc (Kabat Sequences of Nucleic Acid of Immunological Interest) August 1995.
epd (Eukaryotic Promotor Database Release 40, September 1994)
dbest (Database of Expressed Sequence Tags, cumulative daily update)
dbsts (Database of Sequenced Tags Sites Release 1.5, October 1994).

No significant homologies were found.

The organisation of the genomic fragment is shown in FIG. 1. An open reading frame of 383 amino acids is located between nucleotide positions 865 and 2016, the amino acid sequence of this ORF is shown in FIG. 10.

The following datalibraries were screened for homologous amino acid sequences to this ORF using the Experimental GENINFO (R) BLAST Network Service (Blaster).

PDB (Brookhaven Protein Data Bank, April 1994 Release)
Swissprot (SWISS-PROT Release 31.0, March 1995)
PIR (PIR Release 45.0 (complete), Jun. 30, 1995)
Spupdate (SWISS-PROT cumulative weekly update)
Genpept (CDS translations from GenBank(R) Release 90, Aug. 15, 1995).
Gpupdate (cumulative daily updates).
Kabatpro (Kabat Sequences of Proteins of Immunological Interest, June 1995)
TFD (TFD transcription factor (protein) database Release 7.0, June 1993)
ALU (Translations of select Alu repeats from REPBASE)

Similarities were found to a number of proteins, as listed in table IV. The highest similarities were found for a *Haemophilus influenzae* hypothetical protein, a *Mycobacterium leprae* hypothetical protein, putative thiophene and furan oxidation proteins from *Bacillus subtilis, Escherichia coli* and *Pseudomonas putida,* and the *Escherichia coli* Ras-like (Era) protein (Ahnn et al., 1986). These proteins are all GTP-binding proteins.

GTP binding proteins are known to contain 3 to 4 GTP-binding regions each with a consensus sequence and with distinct spacings (Bourne et al., 1991; Dever et al., 1987). The deduced amino acid sequence from the *Campylobacter jejuni* c-gtp-1 gene also contains such regions.

The first GTP-binding motif (G-1, consensus sequence GXXXXGK$^S_T$) was found between amino acid positions 8 to 15 (See FIG. 2).

The second GTP-binding motif (G-2, consensus sequence D(X)$_{10}$T), was found at positions 31–42.

The third GTP-binding motif (G-3, consensus sequence DXXG) was found at positions 55–58.

The fourth motif (G-4, consensus NKXD) was found at positions 116–119.

Moreover, a putative autophosphorylation site (APS), similar to the *E. coli* era gene (ISGTTR), was found at positions 32–37.

Homologies between the deduced *Campylobacter jejuni* sequence, the *Haemophilus influenza* hypothetical protein (Genbank accession number U32699) and the *Mycobacterium leprae* hypothetical protein (Genbank accession number U00021) were further analyzed. Nucleotide sequences show no significant homologies. Also, overall sequence homologies among these proteins are very limited, except at the regions, designated as GTP-binding sites, as shown in the alignment of FIG. 11. The organizational alignment of the three amino acid sequences is shown in FIG. 12.

Remarkably, the conserved GTP-binding domains with the characteristic configuration of G-1 to G-4 motifs are present twice in the three proteins. Each of the proteins seems to contain two separate GTP binding domains.

As summarized in Table V, the spacing between domain 1 and domain 2 varies from 60 amino acids in *Mycobacterium leprae* to 98 amino acids in *Haemophilus influenza*. The spacing between the G-1 and G-3 motifs is 40 amino acids both in region 1 and region 2 in the three proteins. The spacing between the G-3 and G-4 motifs varies from 57 to 61 amino acids.

Since the 2 homologous protein sequences from *M. leprae* and *H. influenzae* show a clear structural relationship to the c-gtp-1 protein from *C. jejuni,* it is highly likely that they belong to the same family of c-gtp-1 gene sequences (c-gtp-1-like genes and proteins).

TABLE 4

Homologous sequences to the c-gtp-1 protein of *Campylobacter jejuni.*

| Accession number | Description | Smallest sum probability P(N) |
|---|---|---|
| U32699 | hypothetical protein H10136 *Haemophilus influenzae* | 9.3 E-46 |
| U00021 | hypothetical GTPbinding protein u0247e *Mycobacterium leprae* | 7.6 E-39 |
| P25811 | Possible thiophene and furan oxidation protein THDF - *Bacillus subtilis* | 8.1 E-14 |
| P25755 | Possible thiophene and furan oxidation protein THDF - *Pseudomonas putida* | 4.2 E-11 |
| P42182 | Bex protein *Bacillus subtilis* | 2.8 E-10 |
| P32559 | Yeast mitochondiral GTPase MSS1 precursor | 3.2 E-10 |
| Z49211 | Mss1p [*Saccharomyces cerevisiae*] | 3.2 E-10 |
| P25522 | Thiophene and furane oxidation protein THDF - *Escherichia coli* | 5.4 E-10 |
| B36933 | Era homolog - *Streptococcus mutans* | 3.5 E-9 |
| M67476 | *Theileria parva* cathepsin L-like cysteine protease and p67 genes | 4.2 E-9 |
| U32781 | Thiophene and furan oxidation protein [*Haemophilus influenzae*] | 5.1 E-9 |
| P37214 | GTP-binding protein era homolog | 8.1 E-8 |
| U32687 | GTP-binding protein [*Haemophilus influenzae*] | 1.4 E-6 |
| L27436 | GTP-binding protein [*Coxiella burnetii*] | 2.9 E-5 |
| P06616 | GTP-binding protein era [*Escherichia coli*] | 5.8 E-5 |

P(N) = factor representing the probability that the homology found between the protein from table 4 and the c-gtp-1 protein of the invention is based on coincidence the smaller this number, the more significant is the homology found.
E = Exponent 10

TABLE 5

Positioning of putative GTP-binding sites G-1 to G-4 in the amino acid sequences from *Campylobacter jejuni* (c-gtp-1 gene), *Haemophilus influenzae* HI0136 and *Mycobacterium leprae* u0247e. See also FIGS. 11 and 12.

| | Domain | | | Domain 2 | | |
|---|---|---|---|---|---|---|
| | G-1 | G-3 | G-4 | G-1 | G-3 | G4 |
| *Campylobacter jejuni* | 8–14 | 55–58 | 116–119 | 202–208 | 249–252 | 313–316 |
| *Haemophilus influenza* | 10–16 | 57–60 | 120–123 | 222–228 | 269–272 | 334–337 |
| *Mycobacterium leprae* | 31–37 | 78–81 | 140–143 | 204–210 | 251–254 | 316–319 |

Comparison Between Domain 1 and Domain 2 Sequences

In order to determine the similarity between domain 1 and domain 2 GTP-binding sequences, a number of sequences were compared. The *Campylobacter jejuni* genomic fragment, domain 1 (CJGTP1_13) and domain 2 (CJGTP2_13) sequences were compared to sequences of fragments obtained from *Campylobacter coli, Campylobacter lari* and *Campylobacter upsaliensis* by amplification of genomic DNA with G-1 and G-3 based primers, as described in example I. The alignment of sequences and the resulting phylogenetic tree are shown respectively in FIGS. 8 and 9. The sequence from domain 2 is clearly distinct from the other sequences. This indicates that the GTP-sites enclosed region sequences, as described in example I are likely to be derived from domain 1.

To determine whether PCR primers GTP 1.1, GTP 3.1 and GTP 3.2 (primerset B, example I), based on G-1 and G-3 sites from domain 1 also allow amplification from G-1 and G-3 sites in domain 2, primer sequences were aligned with both regions. As shown in FIG. 13. G-1 sites from domain 1 and domain 2 are highly similar. Primer GTP 1.1 has only 3 mismatches at the extreme 5' end with the G-1 site from domain 2. However, G-3 sequences from domain 1 and domain 2 are less similar. GTP 3.1 and GTP 3.2 primers have 7 mismatches with the G-3 site from domain 2. Conclusively, GTP 1.1 is likely to anneal efficiently at domain 2 sequences, whereas GTP 1.1 and GTP 3.2 are not likely to recognize G-3 from domain 2. Therefore, primerset B will only amplify domain 1 sequences, and the sequences represented in FIG. 8 (Example I) are corresponding to domain 1 sequences.

Example III

Specificity Testing of GTP-site Based Primers

Introduction

Example I describes the development of PCR amplification of the GTP-sites enclosed region of the c-gtp-1 gene family in different Campylobacter species. Primers were selected from the semi-conserved nucleotide and amino acid sequences of two GTP-binding motifs, G-1 and G-3. These motifs are also present in GTP-binding proteins from various organisms.

The aim of the present example is to describe whether primers, selected from the sequence of GTP-binding sites encoding region in the c-gtp-1 gene of *Campylobacter jejuni* (as described in example I), also allow amplification of GTP-sites enclosed regions from other micro-organisms.

Previous experiments have shown that primerset B. consisting of sense primer GTP 1.1 and antisense primers GTP 3.1 and GTP 3.2, allows optimal amplification of 158 bp GTP-enclosed regions from *Campylobacter jejuni, Campylobacter coli, Campylobacter lari,* and *Campylobacter upsaliensis*. Therefore, the specificity and/or universality of this particular primerset B was further examined for a variety of micro-organisms belonging to the genus Campylobacter (Table 6) and to other prokaryotic genera (Table 8).

Materials and Methods

DNA Isolation

DNA was isolated from bacterial cultures by the following protocol.

1. Bacteria were harvested from plate by suspension in PBS.
2. To 500 µl of the suspension, proteinase K and SDS were added to final concentrations of 100 µg/ml and 0.5%, respectively.
3. The mixture was incubated at 37° C. until the suspension became clear.
4. The sample was extracted twice with phenol:chloroform:isoamylalcolhol (25:24:1).
5. The DNA is precipitated from the aqueous phase by addition of 1/10 volume 3M NaAc and 2 volumes of ethanol.
6. The DNA is resuspended in 100 µl water.

PCR Amplification

Amplification with primerset B was performed according to the following protocol.

| | |
|---|---|
| 1–10 µl | DNA |
| 10 µl | 10x PCR buffer (final concentrations: 10 mM Tris-HCl (pH 9.0), 50 mM KCl, 2.5 mM MgCl$_2$, 0.01% gelatin and 0.1% Triton X-100). |
| 20 µl | dNTP's (final concentration 200 µM each) |
| 50 pmoles | sense primer GTP 1.1 |
| 25 pmoles | antisense primer GTP 3.1 |
| 25 pmoles | antisense primer GTP 3.2 |
| 1 µl | Taq DNA polymerase (0.25 units: SpphaeroQ, Leiden, the Netherlands) |
| ... µl | water |
| 100 µl | total volume |

PCR Program 2 min. 95° C. preheating 40 cycles, consisting of 1 min. at 95° C., 2 min. at 50° C., 2 min. at 74° C.

5 min. 74° C., final extension.

Samples were analyzed on standard 2% agarose TBE gels.

Results

1. Specificity of Primerset B Among Campylobacter spp.

Amplification of genomic DNA isolated from the Campylobacter spp. listed in Table 6 yielded results as specified in Table 7.

All amplification products were also analyzed by reverse hybridization on a Line Probe Assay (LiPA) as described in example IV. The results of the LiPA are also provided in Table 7: they are confirming the species-specifity of the Campylobacter species probes on the LiPA strip. One species, C. hoyilei, shows an aberrant hybridization pattern, since it hybridizes with the probe for C. coli. However, there are several indications based on other taxonomic criteria (e.g. protein pattern analysis, genome homologies . . . ) that C. hoyilei is very closely related and possibly identical to C. coli.

2. Specificity of Primerset B Among Other Micro-organisms

DNA from all bacterial species, as listed in table 8, were subjected to PCR amplification with primerset B.

Results are summarized in table 8. The majority of the samples yielded no visible amplification products. Several bacterial species yielded DNA fragments of various sizes. To examine whether these fragments contain homologous sequences to the Campylobacter species-specific probes, all isolates that yielded any visible DNA fragment, were subjected to reverse hybridization as described in example IV. None of the tested non-Campylobacter bacterial species resulted in a detectable hybridization signal.

This confirms the specificity of the Campylobacter species-specific probes, present on the LiPA.

Conclusions

1. Primerset B results in amplification of a 158 bp fragment in C. jejuni, C. coli, C. lari, C. upsaliensis and C. hoyilei.
2. Primerset B results in amplification of a DNA fragment of ±200 bp in C. mucosalis.
3. Primerset B results in amplification of a DNA fragment of ±210 bp in C. fetus, C. rectum, C. hyointestinalis, Haemophilus influenzae and Acinetobacter spp.
4. Only amplified fragments from Campylobacter jejuni, C. coli, C. lari, and C. upsaliensis yield specific reverse hybridization patterns on LiPA. DNA fragments from C. fetus, C. rectum, C. hyointestinalis, C. mucosalis, as well as from non-Campylobacter bacteria did not result in any detectable reverse hybridization signal.

This example describes the use of primerset B for amplification of the G1–G3 enclosed region of GTPase-gene fragments in different prokaryotic organisms. Primerset B seems to be semi-conserved: some organisms show an amplified fragment (of varying size), other organisms show no detectable fragment after PCR. It should be stressed that, in an analogous way, other types of amplification could be carried out:

amplifications with a more or a less universal character:
By adapting the primer sequences (and possibly using degenerate primer sequences) amplifications can be made more specific (e.g. species or genus specific) or more universal. Less conserved primers can be chosen outside the GTP-binding site regions, resulting in more specific amplifications:

e.g. primersets for species specific amplification of
Campylobacter jejuni: SEQ ID NO 28 and SEQ ID NO 36
Campylobacter coli: SEQ ID NO 29 and SEQ ID NO 37
Campylobacter lari: SEQ ID NO 30 and SEQ ID NO 38
Campylobacter upsaliensis: SEQ ID NO 31 and SEQ ID NO 39 amplification of other GTP-sites enclosed regions (G1–G4, G3–G4):
by chosing the right primer combinations, other GTP-sites enclosed regions, can be amplified.

TABLE 6

Campylobacter spp. tested with primerset B

| | |
|---|---|
| Campylobacter jejuni | LMG 6629 |
| Campylobacter jejuni | ATCC 33250 |
| Campylobacter lari | LMG 8846 |
| Campylobacter coli | LMG 6440 |
| Campylobacter mucosalis | LMG 8499 |
| Campylobacter mucosalis | LMG 8806 |
| Campylobacter rectus | LMG 7614 |
| Campylobacter sputorum | LMG 6447 |
| Campylobacter sputorum | ATCC 33491 |
| Campylobacter concisus | LMG 7789 |
| Campylobacter concisus | LMG 7963 |
| Campylobacter concisus | LMG 7967 |
| Campylobacter hyointestinalis | LMG 7538 |
| Campylobacter hyointestinalis | LMG 9276 |
| Campylobacter showae | LMG 8543 |
| Campylobacter fetus | ATCC 33246 |
| Campylobacter fetus | LMG 6442 |
| Campylobacter fetus | LMG 6569 |
| Campylobacter fetus | LMG 6727 |
| Campylobacter fetus | LMG 6571 |
| Campylobacter curvus | LMG 7609 |
| Campylobacter hoyilei | LMC 15882 |
| Campylobacter upsaliensis | clinical isolate (stool) |

TABLE 7

Results of amplification of Campylobacter spp DNA with primerset B.

| Campylobacter sp. | size (bp) | reverse hybridization pattern (LiPA) |
|---|---|---|
| C. jejuni | 158 | C. jejuni |
| C. lari | 158 | C.lari |
| C. coli | 158 | C.coli |
| C. upsaliensis | 158 | C. upsaliensis |
| C. mucosalis | ±200 | — |
| C. rectus | ±210 | — |
| C. sputorum | none | — |
| C. concisus | aspecific | — |
| C. hyointestinalis | ±210 | — |
| C. showae | none | — |
| C. fetus | ±210 | — |
| C. curvus | none | — |
| C. hoyilei | 158 | C.coli |

TABLE 8

Non-Campylobacter bacterial species tested with primerset B - = no amplification product detectable on ethidium bromide stained agarose gel

| species | source | PCR result |
|---|---|---|
| 1. Neisseria gonorrhoeae | NCTC 8375 | — |
| 2. Neisseria meningitidis | NCTC 10025 | — |
| 3. Neisseria lactamica | NCTC 10616 | — |
| 4. Neisseria cinerea | ATCC 14685 | 160 bp |
| 5. Neisseria polysaccharea | CIP N462 | — |
| 6. Neisseria elongata subsp. elongata | NCTC 10660 | — |
| 7. Kingelia kingae | NCTC 10746 | — |
| 8. Eikenella corrodens | NCTC 10596 | — |
| 9. Neisseria spp. CDC group EF-4a | CDC F191/78 | — |
| 10. Neisseria parelongata (CDC group M-5) | LMG 5354 | — |
| 11. Clostridium perfringens | ATCC 12916 | — |
| 12. Listeria monoytogenes 4B | NCTC 10527 | 300 bp |
| 13. Streptococcus faecalis | 8043 Hoechst | — |
| 14. Streptococcus agalactiae | ATCC 13813 | ±3 kb |
| 15. Salmonella typhimurium | ATCC 29946 | faint smear |
| 16. Staphylococcus aureus | ATCC 6538p | 300 bp |
| 17. Shigella flexneri 2 | RIVM 840947 | faint smear |

TABLE 8-continued

Non-Campylobacter bacterial species tested with primerset B -
= no amplification product detectable on ethidium bromide stained
agarose gel

| species | source | PCR result |
|---|---|---|
| 18. *Staphylococcus epidermidis* | ATCC 12228 | — |
| 19. *Proteus mirabilis* | ATCC 29906 | faint smear |
| 20. *Klebsiella pneumoniae* | ATCC 13883 | faint smear |
| 21. *Salmonella enteritidis* | ATCC 13076 | — |
| 22. Acinetobacter species | clin. isolates | 210 bp |
| 23. *Pseudoinonas aeruginosa* | ATCC 27853 | faint smear |
| 24. *Escherichia coli* | ATCC 11775 | multiple |
| 25. *Enterobacter cloacae* | clin. isol. | faint smear |
| 26. *Bacillus cereus myoides* | ATCC 11778 | 250 bp |
| 27. *Enterobacter agglomerans* | clin. isol. | faint smear |
| 28. *Bacillus subtilis* | ATCC 6633 | 200 bp + ±4 kb |
| 29. Enterococcus sp. | clin. isol. | 350 bp |
| 30. Enterococcus 378016 | " | — |
| 31. Enterococcus 615156 | " | — |
| 32. Enterococcus 320907 | " | — |
| 33. *Mycoplasma pneumoniae* | " | — |
| 34. *Mycoplasma muris* | " | — |
| 35. *Mycoplasma pulmonis* | " | — |
| 36. *Mycoplasma iowae* | " | — |
| 37. *Mycoplasma fermentans* | " | — |
| 38. *Salmonella typhi* 613240 | " | — |
| 39. *Salmonella typhi* 615934 | " | — |
| 40. *Salmonella typhi* | clin. isol. | — |
| 41. *Salmonella typhi* | clin. isol. | — |
| 42. Veillonella species | clin. isol. | — |
| 43. *Haemophilus influenzae* | " | 210 bp |
| 44. *Bacteroides fragilis* | " | ±4 kb |
| 45. *Clostridium freundii* | " | — |
| 46. *Helicobacter pylori* | ATCC 43504 | — |
| 47. *Proteus mirabilis* | clin. isol. | — |
| 48. *Listeria monocytogenes* 4b | NTCT 10527 | — |
| 49. *Klebsiella pneumoniae* | clin. isol. | — |
| 50. *Enterobacter cloacae* | clin. isol. | — |
| 5i. *Enterobacter agglomerans* | clin. isol. | — |
| 52. *Clostridium perfringens* | ATCC 12916 | — |
| 53. *Campylobacter laridis*, stam 2 | clin. isol. | — |
| 54. *Shigella flexneri* | clin. isol. | — |
| 55. *Salmonella enteritidis* | clin. isol. | — |

Example IV

Development of a Reverse Hybridization Assay for Campylobacter Species

Introduction

Example I describes the amplification of parts of the c-gtp-1 gene by PCR using various primersets. Primersets B and C resulted in the production of 158 bp fragments in *C. jejuni, C. coli, C. lari,* and *C. upsaliensis.* Primerset B has been used for further experiments. Sequence analysis of the PCR products obtained revealed consistent sequence conservation within each species as well as sequence diversity between different species. This observation led to the design of Campylobacter species-specific probes, that allow discrimination of at least the four species, mentioned above. This example describes the development of such probes for each of these four species. Furthermore, these probes were used in a reverse hybridization assay format, that allows identification of each PCR product by a single hybridization step.

Probe Design

Sequences, obtained from *Campylobacter jejuni, C. coli, C. lari,* and *C. upsaliensis* by PCR using primerset B, are shown in FIG. 8 of example I. Based on this sequence information, species-specific probes were synthesized, as listed in Table 9. Probes were designed such the probe sequences show a maximal conservation within a species, and a maximal divergence towards the sequence of the closest taxonomical neighbour from which the species should be differentiated. The probes, theoretically derived from the alignment, were then tested experimentally under different hybridization and wash conditions. Little modifications were necessary for some of the probes to obtain maximal sensitivity and specificity.

The probes performing optimally in a LiPA test at 50° C. hybridization temperature are marked with an asterisk in Table 9. It should be understood however that, depending on the experimental test conditions, other probe sequences, or variants of the ones shown in Table 9, may be equally functional.

LiPA-assay

An outline of the LiPA reverse hybridization format, containing the probes marked with an asterisk (*) is represented in FIG. 14. The LiPA was carried out according to the protocol described in International Application WO 94/12670. Primerset B was used for amplification, with the primers biotinylated at the 5' end in order to allow detection of the hybrids formed. PCR reactions and programme were as described in example III. Hybridization was carried out at 50° C. Stringent wash at 50° C. in 2×SSC/0.1% SDS.

Results

Typical examples of developed LiPA strips are shown in FIG. 15. Results show that reactivity is as expected for the reference Campylobacter strains. These reactivities were also confirmed with a number of clinical isolates from the different Campylobacter species. Each probe line resulted in comparable signal intensities at 50° C.

Signal intensities are markedly reduced at 55° C. No aspecific reactivities were observed with other Campylobacter or non-Campylobacter strains.

TABLE 9

Species-specific probes tested in reverse hybridization LiPA

| SEQ ID NO | Campylobacter sp. | Probe sequence (5' to 3') | 45° C. | 50° C. |
|---|---|---|---|---|
| 42 | C. jejuni | TTAATAGAATGGCAAGACAA(*) | C/L | OK |
| 61 | C. jejuni | TTTTTAATAGAATGGCAAGAC | NT | weak |
| 62 | C. jejuni | CTTTTTAATAGAATGGCAAGACAAAG(*) | NT | OK |
| 45 | C. jejuni | ATTCAAAAAAAGCCATGCTT | L | NT |
| 63 | C. jejuni | CATTCAAAAAAAGCCATGCTT | NT | weak |
| 64 | C. jejuni | TTCATATTCATTCAAAAAAAGCCATGCTT(*) | NT | OK |

TABLE 9-continued

Species-specific probes tested in reverse hybridization LiPA

| SEQ ID NO | Campylobacter sp. | Probe sequence (5'to 3') | 45° C. | 50° C. |
|---|---|---|---|---|
| 46 | C. coli | ATCAAGTTTATTTAACAGAAT | OK | neg |
| 65 | C. coli | ATCAAGTTTATTTAACAGAATGG | NT | weak |
| 66 | C. coli | ATCAAGTTTATTTAACAGAATGGCAAG(*) | NT | OK |
| 48 | C. coli | AAAACAGAAGTTTTTATAA | OK | neg |
| 67 | C. coli | CAATAAAACAGAAGTTTTTATAA | NT | weak |
| 68 | C. coli | CCAATAAAACAGAAGTTTTTATAAATTC(*) | NT | OK |
| 50 | C. lari | GACTTGCAAGAAAGCGCATA(*) | OK | OK |
| 51 | C. lari | ACATAAGTGGAACCACAAG(*) | OK | OK |
| 57 | C. upsaliensis | CGCATAGCAAGGCAAAGAA | C | NT |
| 69 | C. upsaliensis | TAATCGCATAGCAAGGCAA(*) | NT | OK |
| 59 | C. upsaliensis | CAATGGTAAAGAAGCCTTGC | L | NT |
| 70 | C. upsaliensis | TATCAATGGTAAAGAAGCCTT(*) | NT | OK |

Abbreviations and symbols:
C/L/U/J: means false positive reactions with resp. C. coli. C. lari. C. upsaliensis. C. jejuni
neg: means no visable hydridization product
weak: means only weakly detectable hybridization product
NT: Not tested
(*)probes selected as being the most optimal for a reverse hydridization test at 50° C.
45° C. and 50° C.: hybridization temperatures

Example V

Isolation and Sequencing of Fragments of the c-gtp-2 Gene Family and Use of Said Gene Fragments for the Discrimination of Veterinary Campylobacter Species Campylobacter spp. can be divided into at least two clinically important entities.

First, the thermophilic Campylobacter species, comprising C. jejuni, C. coli, C. lari, and C. upsaliensis, are important pathogens for humans. The use of GTP-based primers and specific probes for discrimination between the thermophilic species has been amply described in examples I to IV.

The second group comprises C. hyointestinalis, C. fetus and C. mucosalis, which are important in veterinary infections. This example describes the use of GTP primers to discriminate between these non-thermophilic Campylobacter species.

I. Amplification with GTP-based Primerset B

Amplification of C. rectus, C. hyointestinalis, C. fetus with primerset B did not yield a fragment of 158 bp as observed in thermophilic Campylobacter species, but resulted in production of a 210 bp fragment (see table 8). In addition, amplification of DNA from Acinetobacter spp. and Haemophilus influenzae with primerset B yielded a 210 bp fragment. Furthermore, C. mucosalis yielded a fragment of ±200 bp.

2. Sequence Analysis of PCR Products

In order to determine whether there was any significant degree of homology between the 210 bp fragments obtained from the different organisms (C. fetus, C. hyointestinalis, C. rectus, Haemophilus influenzae, and Acinetobacter), the amplicons were subjected to direct sequence analysis. Alignment of the nucleotide sequences is shown in FIG. 16. The alignment of the deduced amino acid sequences is shown in FIG. 17.

Both alignments indicate a significant degree of similarity between the sequences, and it is likely that they are derived from analogous genes, from now on called c-gtp-2 genes, clearly different from the c-gtp-1 gene family sequences described in examples I–IV. Since the genome of Haemophilus influenzae has been completely sequenced, the sequence from the 210 bp amplified fragment was compared with the sequence datalibrary by the GenInfo Blast server. The 210 bp fragment was completely homologous to the Haemophilus influenzae sequence deposited in Genbank with accession number L45034. This sequence encodes a hypothetical protein HI0393. the amino acid sequence of which is shown in FIG. 18.

In addition, a homologous c-gtp-2 like gene sequence from E. coli was retrieved from the Genbank datalibrary, under accession number X61941. This sequence encodes a hypothetical GTP-binding protein (ECPTHGSH). The sequence of the corresponding fragment of this E. coli gene (and protein) is shown in the respective alignments of FIGS. 16 and 17.

The amplification results mentioned above show that primers derived from the G-1 and G-3 sites from the c-gtp-1 gene from Campylobacter jejuni, and more particularly primerset B as described in example I, are sufficiently conserved to allow the amplification of other GTPase genes in other organisms. In particular, a fragment from another putative GTPase gene, c-gtp-2, is amplified in veterinary Campylobacter species, in Acinetobacter species, and in

*Haemophilus influenzae.* Moreover, it is highly likely that a corresponding fragment would be amplified in other species, like e.g. in *E. coli,* where a c-gtp-2 homologous gene is shown to exist.

The following scheme shows an alignment of primerset B, containing primers GTP1.1, GTP3.1 and GTP3.2, with the G-1 and G-3 like sequences from the HI0393 protein (gene). G-1 and G-3-like sequences were found between amino acid positions 9 to 15 and 72 to 75, respectively. Although some mismatches occur, especially in the G-3 like sequences, amplification is still possible. The intervening sequence is 56 amino acids, and the total amplification product has a calculated size of 209 bp. No G-4 (NKVD)-like sequence could be detected.

G-1-like Sequence (Bold AA are Consensus)

```
aa9         G   L   P   N   V   G   K   S   T   aa17
nt 24       GGA TTG CCA AAT GTC GGC AAA TCT ACT
                                x
GTP 1.1         G CCA AAT GTT GGI AAR TC
```

G-3-like Sequence

```
aa72        D   I   A   G   L   V   aa 77
            GAC ATC GCA GGC TTA GTT nt 232
            x   x   x x x   x
GTP 3.1     GAY AGI GGA GGG CTT GAT
            x           x   x
GTP 3.2     GAY AGI SSA GGI CTI GAT
```

3. Selection of Species Specific Probes for Veterinary Campylobacter Species

From the alignment on FIG. 16 probe regions could be delineated for the specific determination of *Campylobacter fetus* and *Campylobacter hyointestinalis,* as specified below:

```
Specific probes
for C. fetus:

TTTTAATGCGTTAACAAAAC      (SEQ ID NO 71)

CTAGCAATGCAGAATCTGCA      (SEQ ID NO 72)

CTATCCATTTTGCACTATAG      (SEQ ID NO 73)

ATAGTTCCGGTTCCAGATAT      (SEQ ID NO 74)

TCCAGATATACGCTTAAATG      (SEQ ID NO 75)

Specific probes
for C. hyointestinalis

TTTTAATGCTCTAACAAAAC      (SEQ ID NO 76)

CTAGTAACGCAGAGGCNGCA      (SEQ ID NO 77)

CTATCNGTTTTGTACTATNG      (SEQ ID NO 78)

TNNTGATGCGCGTTTGAATG      (SEQ ID NO 79)
```

REFERENCES

Agarwal et al. 1972. Agnew. Chem. Int. Ed. Engl. 11: 451.

Ahnn J., March P. E., Takiff H. E., and Isouye M. 1986. A GTP-binding protein of *Escherichia coli* has homology to yeast RAS proteins. Proc. Natl. Acad. Sci. USA 83:8849–8853.

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Bej A, Mahbubani M, Miller R, Di Cesare J, Haff L, Atlas R (1990) Mutiplex PCR amplification and immobilized capture probes for detection of bacterial pathogens and indicators in water. Mol Cell Probes 4:353–365.

Baeucage et al. 1981. Tetrahedron Letters 22: 1859–1862.

Bernstein H et al. (1989) Nature 340, 482–486.

Boom R, Sol C, Salimans M, Jansen C, Wertheim van Dillen P and van der Noordas J (1990) Rapid and simple method for purification of nucleic acids. J Clin Microbiol 28:495–503.

Bourne H, Sanders D and McCormick F (1991) The GTPase superfamily: conserved structure and molecular mechanism. Nature, 349, 117–127.

Compton J (1991). Nucleic acid sequence-based amplification. Nature, 350:91–92.

Dever T E, Glynias M J, and Merrick W C, GTP-binding domain: Three consensus sequence elements with distinct spacing. Proc. Natl. Acad. Sci. USA. 1987, 84:1814–1818.

Duck P (1990). Probe amplifier system based on chimeric cycling oligonucleotides. Biotechniques 9, 142–147.

Eyers, M., S. Chapelle, G. Van Camp, H. Goossens, and R. De Wachter, 1993. Discrimination among thermophilic Campylobacter species by polymerase chain reaction amplification of 23S rRNA gene fragments. J. Clin. Microbiol. 31:3340–3343.

Ezaki, T., N. Takeuchi, S. L. Liu, A. Kai, H. Yamamoto, and E. Yabuuchi, 1988. Small-scale DNA preparation for rapid genetic identification of Campylobacter species without radioisotope. Microbiol. Immunol. 32:141–150.

Giesendorf B. A., Goossens H., Niesters H. G., Van Belkum A., Koeken A., Endtz H. P., Stegeman H., and Quint W. G., 1994. Polymerase chain reaction-mediated DNA fingerprinting for epidemiological studies on Campylobacter spp. J. Med. Microbiol. 40:141–147.

Giesendorf B. A., Quint W. G., Henkens M. H., Stegeman H., Huf F. A., and Niesters H. G. 1992. Rapid and sensitive detection of Campylobacter spp. in chicken products by using the polymerase chain reaction. Appl. Environ. Microbiol. 58:3804–3808.

Giesendorf B. A., Van Belkum A., Koeken A., Stegeman H., Henkens M. H., Van der Plas J., Goossens H., Niesters H. G., and Quint W. G. 1993. Development of species-specific DNA probes for *Campylobacter jejuni, Campylobacter coli,* and *Campylobacter lari* by polymerase chain reaction fingerprinting. J. Clin. Microbiol. 31:1541–1546.

Gill D. Hatfull G and Salmond G (1986) Molec. Gen. Genet. 205, 134–145.

Goossens, H. and J.-P. Butzler, 1992. Isolation and identification Campylobacter spp. p. 93–103. In I. Nachamkin, M. J. Blaser, and L. S. Tompkins (eds.). *Campylobacter jejuni,* current status and future trends. American Society for Microbiology, Washington DC.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Hsiung et al. 1979, Nucleic Acid Res. 6:1371.

Jayarao B. M., Bassem B. J., Caetano-Anoliès G., Gresshoff P. M., and Oliver S. P. 1992. Subtyping of *Streptococcus uberis* by DNA amplification fingerprinting. J. Clin. Microbiol. 30:1347–1350.

Korolik, V., P. J. Coloe, and V. Krishnapillai, 1988. A specific DNA probe for the identification of *Campylobacter jejuni.* J. Gen. Microbiol. 134:521–529.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173–1177.

Kwok S, Kellogg D, McKinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Landgren U, Kaiser R, Sanders J, Hood L (1988). A ligase-mediated gene detection technique. Science 241:1077–1080.

Laursen R, L'Italien J, Nakargatti S and Miller D (1981). J. Biol. Chem. 256, 8102–8109.

Lior H., Woodward D. L., Edgar J. A., Laroche L. J., and Gill P. 1982. Serotyping of *Campylobacter jejuni* by slide agglutination based on heat-labile antigenic factors. J. Clin. Microbiol. 15:761–768.

Lior H, 1984, New, extended biotyping scheme for *Campylobacter jejuni, Campylobacter coli* and "*Campylobacter laridis*". J. Clin. Microbiol. 20:636–640.

Lizardi P, Guerra C, Lomeli H, Tussie-Luna I, Kramer F (1988) Exponential amplification of recombinant RNA hybridization probes. Bio/Technology 6:1197–1202.

Lomeli H, Tyagi S, Printchard C, Lisardi P, Kramer F (1989) Quantitative assays based on the use of replicatable hybridization probes. Clin Chem 35: 1826–1831.

March P and Inouye M (1985). J. Biol. Chem. 260, 7206–7213.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

McMillin D. E., and Muldrow L. L. 1992. Typing of toxic strains of *Clostridium difficile* using DNA fingerprints generated with arbitrary polymerase chain reaction primers. FEMS Microbiol. Lett. 71:5–9.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134–43.

Nielsen P, Egholm M, Berg R, Buchardt O (1991) Sequence-selective recognition of DNA by strand displacement with a thymine-substituted polyamide. Science 254(5037): 1497–500.

Nielsen P, Egholm M, Berg R, Buchardt O (1993) Sequence specific inhibition of DNA restriction enzyme cleavage by PNA. Nucleic-Acids-Res. 21(2):197–200.

Nuyten P J M, van Asten F J A M, Gaastra W, van der Zeijst B A M, structural and functional analysis of two *Campylobacter jejuni* flagellin genes. J. Biol. Chem. 1990, 265,29: 17798–17804.

Olive D. M., M. Johny, and S. K. Sethi, 1990. Use of an alkaline phosphatase-labeled synthetic oligonucleotide probe for detection of *Campylobacter jejuni* and *Campylobacter coli*. J. Clin. Microbiol. 28:1565–1569.

Oyofo, B. A., S. A. Thornton, D. H. Burr, T. J. Trust, O. R. Pavlovskis and P. Guerry, 1992. Specific detection of *Campylobacter jejuni* and *Campylobacter coli* by using polymerase chain reaction. J. Clin. Microbiol. 30:2613–2619.

Oyofo B. A. and Rottins D. M. 1993. Efficacy of filter types for detecting *Campylobacter jejuni* and *Campylobacter coli* in environmental water sample by polymerase chain reaction. Appl. Environ. Microbiol. 59:4090–4095.

Oyofo B. A., Thornton S. A., Burr D. H., Trust T. J., Pavlovskis O. R., and Guerry P. 1992. Specific detection of *Campylobacter jejuni* and *Campylobacter coli* by using polymerase chain reaction. J. Clin. Microbiol. 30:2613–2619.

Picken, R. N., Z. Wang, and H. L. Yang, 1987. Molecular cloning of a species-specific DNA probe for *Campylobacter jejuni*. Mol. Cell Probes. 1:245–259.

Popovic-Uroic, T., C. M. Patton, I. K. Wachsmuth, and P. Roeder, 1991. Evaluation of an oligonucleotide probe for identification of Campylobacter species. Lab. Med. 22:533–539.

Romaniuk, P. J. and T. J. Trust, 1989. Rapid identification of Campylobacter species using oligonucleotide probes to 16S ribosomal RNA. Mol. Cell Probes. 3:133–142.

Römisch K et al. (1989) Nature 340, 478–482.

Roop, R. M., R. M. Smibert, J. L. Johnson, and N. R. Krieg, 1984. Differential characteristics of catalase-positive campylobacters correlated with DNA homology groups. Can. J. Microbiol. 30:938–951.

Sacerdot C. Desen P., Hershey J. Plumbridge J and Grunberg-Manago M (1984). Proc. Natl. Acad. Sci. USA. 81. 7787–7791.

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239: 487–491.

Sambrook J, Fritsch E F, Maniatis T, 1989. Molecular cloning, a laboratory manual 2nd edition. Cold Spring Harbor Laboratory Press.

Skirrow M. B., Blase M. J., 1992. Clinical and eopidemiological considerations. P. 3–8. In I. Nachamkin, M. J. Blaser, L. S. Tompkins (ed.) *Campylobacter jejuni*, current status and future trends. American Society for Microbiology, Washington DC.

Stonnet, V. and J. L. Guesdon, 1993. *Campylobacter jejuni*: specific oligonucleotides and DNA probes for use in polymerase chain reaction-based diagnosis. FEMS Immunol. Med. Microbiol. 7:337–344.

Taylor, D. E. and K. Hiratsuka, 1990. Use of non-radioactive DNA probes for detection of *Campylobacter jejuni* and *Campylobacter coli* in stool specimens. Mol. Cell Probes. 4:261–271.

Tenover, F. C., L. Carlson, S. Barbagallo, and I. Nachamkin, 1990. DNA probe culture confirmation assay for identification of thermophilic Campylobacter species. J. Clin. Microbiol. 38:1284–1287.

Thorne, G. M., A. Macone, and D. A. Goldmann, 1990. Enzymatically labelled nucleic acid (NA) probe assays for detection of Campylobacter spp. in human faecal specimens and in culture. Mol. Cell. Probes. 4:133–142.

Tjernberg and Ursing (1989). Clinical strains of Acinetobacter classified by DNA-DNA hybridization. APMIS, 97, 595–605.

Trach K and Hoch J (1989). J. Bact. 171. 1362–1371 (1989).

Van Camp, G., H. Fierens, P. Vandamme, H. Goossens, A. Huygebaert, and R. De Wachter, 1993. Identification of enteropathogenic Campylobacter species by oligonucleotide probes and polymerase chain reaction based on 16S rRNA genes. System Appl. Microbiol. 16:30–36.

Van Belkum A. 1994. DNA fingerprinting of medically important microorganisms by use of PCR. Clin. Microbiol. Rev. 7:174–184.

Walker G, Little M, Nadeau J, Shank D (1992). Isothermal in vitro amplification of DNA by a restriction enzyme/DNA polymerase system. Proc Natl Acad Sci USA 89:392–396.

Wegmüller, B., J. Lüthy, and U. Candrian, 1993. Direct polymerase chain reaction detection of *Campylobacter jejuni* and *Campylobacter coli* in raw milk and dairy products. Appl. Environ. Microbiol. 59:2161–2165.

Wegmüller B. Lüthy J. and Candrian U. 1999. Direct polymerase chain reaction detection of *Campylobacter coli* in raw milk and dairy products. Appl. Environ. Microbiol. 59:2161–2165.

Welsch J., and McClelland M. 1991. Genomic fingerprinting using arbitrarily primed PCR and a matrix of pairwise combinations of primers. Nucleic. Acids. Res. 19:5275–5279.

Wesley, I. V., R. D. Wesley, M. Cardella, F. E. Dewhirst, and B. J. Paster, 1991. Oligodeoxynucleotide probes for *Campylobacter fetus* and *Campylobacter hyointestinalis* based on 16S rRNA sequences. J. Clin. Microbiol. 29:1812–1817.

Wu D. Wallace B (1989). The ligation amplification reaction (LAR)—amplification of specific DNA sequences using sequential rounds of template-dependent ligation. Genomics 4:560–569. Barany F (1991). Genetic disease detection and DNA amplification using cloned thermostable ligase. Proc Natl Acad Sci USA 88: 189–193.

Zengel J, Archer R and Lindahl, L (1984). Nucleic Acid Res. 12, 2181–2192.

Zhou, Y. T. and S. Q. Wang. 1989. Application of a biotin-labelled DNA probe to detect Campylobacter. Int. J. Med. Microbiol. 272:186–190.

What is claimed is:

1. A polynucleic acid comprising at least one of the following sequences:
   (i) the polynucleic acid sequence extending from nucleotide position 865 to position 2016 of SEQ ID NO 1, or
   (ii) one of the polynucleic acid sequences represented by SEQ ID NO 12, 19, or 22, or
   (iii) a polynucleic acid sequence showing at least 95% identity to any of the sequences as specified in (i) or (ii), or
   (iv) a polynucleic acid sequence consisting of a fragment containing at least 8 contiguous nucleotides of any of the sequences as specified in (i) to (iii), or
   (v) a polynucleic acid sequence complementary to any of the sequences as specified in (i) to (iv), or
   (vi) a polynucleic acid sequence as specified in any of (i) to (v) wherein T is replaced by U.

2. An oligonucleotide primer comprising from 10 to 30 contiguous nucleotides of a polynucleic acid according to claim 1; wherein said primer can function to allow amplification of part of said polynucleic acid.

3. An oligonucleotide probe comprising from 10 to 30 contiguous nucleotides of a polynucleic acid according to claim 1; wherein said oligonucleotide probe hybridizes to said polynucleic acid in a hybridization medium comprising 5×SSC at a hybridization temperature between 40° C. and 50° C.

4. A polynucleic acid comprising at least one of the following sequences:
   (i) the polynucleic acid sequence extending from nucleotide position 865 to position 2016 of SEQ ID NO 1, or
   (ii) one of the polynucleic acid sequences represented by SEQ ID NO 1, 12, 19, 22, 25–27, 33, 34, and 81,
   (iii) a polynucleic acid sequence showing at least 95% identity to any of the sequences as specified in (i) or (ii), or
   (iv) polynucleic acid sequence complementary to any of the sequences as specified in (i) to (iii), or
   (v) a polynucleic acid sequence as specified in any of (i) to (iv) wherein T is replaced by U.

5. An oligonucleotide primer according to claim 2 comprising an oligonucleotide sequences represented by any of SEQ ID NOS 24, 25, 26, 27, 28, 29, 30, 31, 32, 33, 34, 35, 36, 37, 38, 39, 80 or 81 or functionally equivalent variants of these primers; wherein each variant shares at least 95% sequence identity with at least one of said SEQ ID NOs and said variant can function to amplify part of a polynucleic acid, as described in claim 1.

6. A set of primers comprising at least one of the following sets of primers:
   A: SEQ ID NO 24 and SEQ ID NO 32
   B: SEQ ID NO 25 and (SEQ ID NO 33 and SEQ ID NO 34)
   C: SEQ ID NO 26 and (SEQ ID NO 33 and SEQ ID NO 34)
   D: SEQ ID NO 27 and (SEQ ID NO 33 and SEQ ID NO 34)
   E: SEQ ID NO 25 and SEQ ID NO 35
   F: SEQ ID NO 26 and SEQ ID NO 35
   or variants of these respective primers; wherein each variant shares at least 95% sequence identity with the respective SEQ ID NO, and wherein each set of primers can function to allow amplification of a polynucleic acid according to claim 1.

7. An oligonucleotide probe obtainable by a process comprising the steps of:
   a) amplifying, using a pair of primers according to any of claims 5, 6 or 2, a GTP-sites enclosed region present in the GTPase gene of the organism to be determined, and repeating the same for a number of other organisms, phylogenetically closely related to the organism to be determined (=closest neighbors), or suspected of being present in the same type of sample as the organism to be determined.
   b) determining the sequences of the amplified regions,
   c) aligning the sequences obtained to allow mutual comparison, and selecting a region in the sequence of the organism to be determined, said region being characterized by a maximal sequence conservation with the organism to be determined, and a maximal sequence divergence (minimum 1 basepair mismatch) towards the other organisms,
   d) generating a probe comprising a sequence of at least 8 contiguous nucleotides from the region selected in (c),
   e) defining the hybridization conditions required to obtain the desired hybridization characteristics for the probe selected in (d).

8. An oligonucleotide probe according to claim 3, hybridizing specifically to the DNA of thermophylic Campylobacter species, and comprising at least one of the sequences represented by SEQ ID NO 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70, or a fragment of at least 8 contiguous nucleotides of any of the sequences represented by SEQ ID NO 1, 12, 19, or 22; wherein said fragment hybridizes specifically to DNA of thermophylic Campylobacter species, or a variant of said probe which has at least 95% sequence identity with said probe, and provided that said variant still hybridizes specifically to the DNA of thermophylic Campylobacter species in a hybridization medium containing 5×SSC at a hybridization temperature between 40° C. and 50° C.

9. An oligonucleotide probe according to claim 8, hybridizing specifically to the DNA of *Campylobacter jejuni*, and comprising at least one of the sequences represented by SEQ ID NO 41, 42, 43, 44, 45, 61, 62, 63, 64, or a fragment of at least 8 contiguous nucleotides of the sequence represented by SEQ ID NO 1, wherein said fragment hybridizes specifically to *C. jejuni* DNA, or a variant of said probe which has at least 95% identity to said probe; wherein said variant still hybridizes specifically to the DNA of *C. jejuni*, in a hybridization medium containing 5×SSC at a hybridization temperature between 40° C. and 50° C.

10. An oligonucleotide probe according to claim 8, hybridizing specifically to the DNA of *C. coli* and comprising at least one of the sequences represented by SEQ ID NO 46, 47, 48, 65, 66, 67, 68, or a fragment of at least 8 contiguous nucleotides of the sequence represented by SEQ ID NO 12; wherein said fragment hybridizes specifically to DNA of *C. coli*, or a variant of said probe which has at least 95% sequence identity with said probe, and provided that said variant still hybridizes specifically to the DNA of *C. coli* in a hybridization medium containing 5×SSC at a hybridization temperature between 40° C. and 50° C.

11. An oligonucleotide probe according to claim 8, hybridizing specifically to the DNA of *C. lari* and comprising at least one of the sequences represented by SEQ ID NO 49, 50, 51, 52, 53, 54, 55, 56, or a fragment of at least 8 contiguous nucleotides of the sequence represented by SEQ ID NO 19; wherein said fragment hybridizes specifically to DNA of *C. lari*, or a variant of said probe which has at least 95% sequence identity with said probe, and provided that said variant still hybridizes specifically to the DNA of *C. lari* in a hybridization medium containing 5×SSC at a hybridization temperature between 40° C. and 50° C.

12. An oligonucleotide probe according to claim 8, hybridizing specifically to the DNA of *C. upsaliensis* and comprising at least one of the sequences represented by SEQ ID NO 57, 58, 59, 60, 69, 70, or a fragment of at least 8 contiguous nucleotides of the sequence represented by SEQ ID NO 22; wherein said fragment hybridizes specifically to DNA of *C. upsaliensis*, or a variant of said probe which has at least 95% sequence identity with said probe, and provided that said variant still hybridizes specifically to the DNA of *C. upsaliensis* in a hybridization medium containing 5×SSC at a hybridization temperature between 40° C. and 50° C.

13. A method for the detection and identification of at least one prokaryotic micro-organism, or the simultaneous detection and differentiation of several prokaryotic micro-organisms in a biological sample, said method comprising the steps of:
   (i) releasing, isolating or concentrating the polynucleic acids present in the sample,
   (ii) if need be, amplifying the polynucleic acids present in the sample, with a set of primers according to any of claims 5, 6, or 2,
   (iii) hybridizing the polynucleic acids of (i) or (ii) with at least one of the probes according to any of claims 7–9 or 3,
   (iv) detecting the hybrids formed in step (iii) with each of the probes under appropriate hybridization and wash conditions,
   (v) identifying the micro-organisms present in the sample from the differential hybridization signals obtained in (iv).

14. A method according to claim 13, for detection and/or differentiation of thermophylic Campylobacter species with said primer set of step (ii), of claim 13, comprising a set of primers according to claim 6 and with said probes of step (iii), of claim 13, comprising at least one probe according to claim 8.

15. A method according to claim 13 or 14, wherein said probes are immobolized on a solid support.

16. A kit for detection and identification of at least one prokaryotic micro-organism, or the simultaneous detection and/or differentiation of several prokaryotic micro-organisms in a sample, comprising the following components:
   (i) when appropriate, at least one suitable primer or primer set according to any of claims 5, 6, or 2,
   (ii) at least one of the probes according to claims 7, 8, 9, or 3,
   (iii) possibly a buffer or components necessary to produce the buffer enabling a hybridization reaction between these probes and the nucleic acids present in the sample,
   (iv) possibly a solution or components necessary to produce the solution, enabling washing of the hybrids formed, in step (iii), under the appropriate wash conditions,
   (v) when appropriate, a means of detecting the hybrids resulting from the preceding hybridization.

17. A kit according to claim 16, for detection and/or differentiation of thermophylic Campylobacter species in a sample, wherein said primer set comprises a set of primers according to claim 6, and wherein said probes comprise at least one probe according to claim 8.

18. A process for the detection and/or differentiation of thermophylic Campylobacter species, employing a nucleic acid based assay comprising: using a polynucleic acid, according to claim 1, as a target sequence specific for the thermophylic Campylobacter species.

19. A method for selecting and generating an oligonucleotide probe comprising the steps of:

a) amplifying, using a pair of primers according to any of claims 5, 6, or 2, a GTP-sites enclosed region present in the GTPase gene of the organism to be determined, and repeating the same for a number of other organisms, phylogenetically closely related to the organism to be determined (=closest neighbors), or suspected of being present in the same type of sample as the organism to be determined.

b) determining the sequences of the amplified regions, c) aligning the sequences obtained to allow mutual comparison, and selecting a region in the sequence of the organism to be determined, said region being characterized by a maximal sequence conservation with the organism to be determined, and a maximal sequence divergence (minimum 1 basepair mismatch) towards the other organisms, d) generating a probe comprising a sequence of at least 8 contiguous nucleotides from the region selected in (c), e) defining the hybridization conditions required to obtain the desired hybridization characteristics for the probe selected in (d).

* * * * *

```
                         SEQUENCE LISTING (1) GENERAL INFORMATION:

(iii) NUMBER OF SEQUENCES: 96

(2) INFORMATION FOR SEQ ID NO: 1:

(i) SEQUENCE CHARACTERISTICS:
        (A) LENGTH: 2047 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 864..2016

(ix) FEATURE:
        (A) NAME/KEY: mat_peptide
        (B) LOCATION: 864..2013

(xi) SEQUENCE DESCRIPTION: SEQ ID NO: 1:

GATATCAAGC TTTAGTGACA TGAATTTGAT AAATGGTGCC TAAAGTTCCC ATAATGGCAA      60

TGATAAGCCA AGCTGTAAGA CTTGGCATCA CAAAAGGTGC TAGAATGAAA TCTAAATGTA     120

AAGAATCAAG ATGCTGTGGT TCAAAAAATT CAGCACTGAT CATAGAAATT AAAGGCATTA     180

AGGTTCCTAA AAGGATAAAA GAAAAGGCAA TTTGTTCTGT AGTGTAAGAT TTTCTAAGTT     240

CTCTTACACT TGTAAGAGCT AAGCAGCTAA AAATCCACTC GTGATACCTA TAACTGAATT     300

TTTTAAATCA AAGCCTGAAT GATTTAAATT AATGAGCCCA AGGCTGAGCA ATTAAAAGCA     360

CTCCACCAAA TGCTATTAAA ATTCCTACTC CAGCCTTTGA TGCCAATATT TTCTTTAAAA     420

ACAACAAAAG CTATTAAAGT AATAAAAATA GGAGCAGTTT TTTGAAAAGC AAAAGCTCCG     480

CCTAGTGTAA TATTTGAAAC ATTATAGAAA AACATATATA GTGAAAGCGT GCCTACTACT     540

CCACGAAATA CCAAGAGCCA AAAATGTCCC CCTTCTTTAT GTGCCTTAGA TCGTTTTAAA     600

AGATAGACTA TGAAAAAAAT TCCTATGATA TTTCTAAAAA CATAATTTCT ATAGAACTCA     660

TTTCCTTGCT AAGAATTTTT CCACAAGCNC CCATAAGTGC AAAATCCAAA CATGCTAAAA     720

TCATGAAATA AATTCCTAAA TTATGCTTGA TTACTTTTAG CATTTTTTTT CCTTGACTAA     780

AATCTGTGTT AATTCTAGTC TTTTTTTGCT TAATATTAAG CCAAATTTTA TATAATTTTA     840

AAAATATAAT TTTCTAGGAA AAAAATGCAA AGCATCATAC TTATAGGCAA GCCAAATGTT     900

GGAAAATCAA GTCTTTTTAA TAGAATGGCA AGGCAAAGAA TAGCTATTAC AAGTGATATT     960
```

```
TCAGGTACAA CTAGAGATAC AAATAAAACG CAAATTCATA TTCATTCAAA AAAAGCCATG   1020

CTTATTGATA GTGGAGGGCT TGATGAAAGT GATGAACTTT TTAAAAATGT GAAAAAAAAC   1080

ACTTTAAAAG TAGCTAAAGA AAGCGATATC ATACTTTATC TAGTTGATGG AAATTAGCG    1140

CCTGATGATG AGGATAGACA GTTTTTTTAT TCTTTAAAAA AACTTGGAAA ACCTATAGCC   1200

TTAGTGGTTA ATAAAGTAGA TAATAAAAAA GATGAAGAAA GGGCTTGGGA GTTTGCAAAT   1260

TTTGGAGTAA AGGAAATCTT CAATCTTTCA GTAACCCATA ATGTAGGCTT AGATGAACTT   1320

TATGAATGGC TTGAAAAATT TTTACATGAA GAGTTTTTAA TCCCTGATGA AGAAGAAAAT   1380

TTAGAAGATT TTTTAGAGCA TTATGAAGAA GGAAAAGAAT TTCAATTTAA AGAAGTCGAT   1440

CAAAATCATA TCAGAGTGGG TATTGTAGGG CGTGTAAATG TTGGAAAATC AAGTCTTTTA   1500

AATGCTTTGG TTAAACAAGA ACGCAGTGTT GTAAGTTCTA TCGCAGGAAC TACTATAGAT   1560

CCTGTTAATG AAAGTGTAGT TCATAAAGAT AAAGTGATGA AATTTGTTGA TACTGCAGGT   1620

ATTAGAAAAA GGGGTAAAAT TCAAGGACTC GAACGCTTTG CCCTAAATCG CACGGAAAAA   1680

ATTTTATCTC ATTCTCAAAT AGCACTTTTG GTTTTAGATG CGCATGAGGG CTTTAACGAA   1740

CTTGATGAAC GCATTGCTGG GCTTGTGGCT AAGCATTATT TGGGTGTGAT TATTGTTTTA   1800

AATAAATGGG ATAAAGTGA GATGGATTTT GATAAAACTG TAAAAGAATT GCATCTTGAT   1860

CGTTTTAAAT TTCTAGCTTA CGCACCTGTG ATTAGCGTAT CGGCTTTAAG TGGAAAAAGG   1920

GTGCATGTTT TACTCGATAA AATTTTGCAA ATTTTTGAGA ATTCACTCA AAAAATCCAA    1980

ACTTCTAAGC TTATGAAAAT TCTTTCATA CTTTAAATTT AGGGGTGAAT TACATTTTAC    2040

CAGGAGC                                                             2047

(2) INFORMATION FOR SEQ ID NO: 2:

(i) SEQUENCE CHARACTERISTICS:
        (A) LENGTH:  383 amino acids
        (B) TYPE: amino acid
        (D) TOPOLOGY: linear (ii) MOLECULE TYPE: protein (xi) SEQUENCE DESCRIPTION: SEQ ID NO: 2:

Met Gln Ser Ile Ile Leu Ile Gly Lys Pro Asn Val Gly Lys Ser Ser
 1               5                  10                  15

Leu Phe Asn Arg Met Ala Arg Gln Arg Ile Ala Ile Thr Ser Asp Ile
                20                  25                  30

Ser Gly Thr Thr Arg Asp Thr Asn Lys Thr Gln Ile His Ile His Ser
            35                  40                  45

Lys Lys Ala Met Leu Ile Asp Ser Gly Gly Leu Asp Glu Ser Asp Glu
        50                  55                  60

Leu Phe Lys Asn Val Lys Lys Asn Thr Leu Lys Val Ala Lys Glu Ser
65                  70                  75                  80

Asp Ile Ile Leu Tyr Leu Val Asp Gly Lys Leu Ala Pro Asp Asp Glu
                85                  90                  95

Asp Arg Gln Phe Phe Tyr Ser Leu Lys Lys Leu Gly Lys Pro Ile Ala
            100                 105                 110

Leu Val Val Asn Lys Val Asp Asn Lys Lys Asp Glu Glu Arg Ala Trp
        115                 120                 125

Glu Phe Ala Asn Phe Gly Val Lys Glu Ile Phe Asn Leu Ser Val Thr
    130                 135                 140

His Asn Val Gly Leu Asp Glu Leu Tyr Glu Trp Leu Glu Lys Phe Leu
145                 150                 155                 160
```

```
His Glu Glu Phe Leu Ile Pro Asp Glu Glu Asn Leu Glu Asp Phe
            165                 170                 175

Leu Glu His Tyr Glu Glu Gly Lys Glu Phe Gln Phe Lys Glu Val Asp
            180                 185                 190

Gln Asn His Ile Arg Val Gly Ile Val Gly Arg Val Asn Val Gly Lys
            195                 200                 205

Ser Ser Leu Leu Asn Ala Leu Val Lys Gln Glu Arg Ser Val Val Ser
    210                 215                 220

Ser Ile Ala Gly Thr Thr Ile Asp Pro Val Asn Glu Ser Val Val His
225                 230                 235                 240

Lys Asp Lys Val Ile Glu Phe Val Asp Thr Ala Gly Ile Arg Lys Arg
                245                 250                 255

Gly Lys Ile Gln Gly Leu Glu Arg Phe Ala Leu Asn Arg Thr Glu Lys
                260                 265                 270

Ile Leu Ser His Ser Gln Ile Ala Leu Leu Val Leu Asp Ala His Glu
                275                 280                 285

Gly Phe Asn Glu Leu Asp Glu Arg Ile Ala Gly Leu Val Ala Lys His
            290                 295                 300

Tyr Leu Gly Val Ile Ile Val Leu Asn Lys Trp Asp Lys Ser Glu Met
305                 310                 315                 320

Asp Phe Asp Lys Thr Val Lys Glu Leu His Leu Asp Arg Phe Lys Phe
                325                 330                 335

Leu Ala Tyr Ala Pro Val Ile Ser Val Ser Ala Leu Ser Gly Lys Arg
                340                 345                 350

Val His Val Leu Leu Asp Lys Ile Leu Gln Ile Phe Glu Asn Phe Thr
                355                 360                 365

Gln Lys Ile Gln Thr Ser Lys Leu Met Lys Ile Ser Phe Ile Leu
                370                 375                 380

(2) INFORMATION FOR SEQ ID NO: 3:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

AGCCTTTTTA ATAGAATGGC AAGACAAAGA ATAGCTATTA CAAGTGATAT TTCAGGCACA    60

ACTAGAGATA CAAATAAAAC GCAAAT                                        86

(2) INFORMATION FOR SEQ ID NO: 4:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

AGTCTTTTTA ATAGAATGGC AAGACAAAGA ATAGCTATTA CAAGTGATAT TTCAGGTACA    60

ACTAGAGATA CAAATAAAAC GCAAATTCAT ATTCATTCAA AAAAGCCAT GCTTATT      117

(2) INFORMATION FOR SEQ ID NO: 5:
```

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

AGCCTTTTTA ATAGAATGGC AAGACAAAGA ATAGCTATTA CAAGTGATAT TTCAGGTACA       60

ACTAGAGATA CAAATAAAAC GCAAATTCAT ATTCATTCAA AAAAAGCCAT GCTTATT          117

(2) INFORMATION FOR SEQ ID NO: 6:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 6:

AGTCTTTTTA ATAGAATGGC AAGACAAAGA ATAGCTATTA CAAGTGATAT TTNAGGTACA       60

ACTAGAGATA CAAATAAAAC GCAAATTCAT ATTCATTCAA AAAAAGCCAT GCTTATT          117

(2) INFORMATION FOR SEQ ID NO: 7:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 7:

AGCCTTTTTA ATAGAATGGC AAGACAAAGA ATAGCTATTA CAAGTGATAT TTCAGGCACA       60

ACTAGAGATA CAAATAAAAC GCAAATTCAT ATTCATTCAA AAAAAGCCAT GCTTATT          117

(2) INFORMATION FOR SEQ ID NO: 8:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 8:

AGTCTTTTTA ATAGAATGGC AAGACAAAGA ATAGCTATTA CAAGTGATAT TTCAGGCACA       60

ACTAGAGATA CAAATAAAAC AGAAATTCAT ATTCATTCAA AAAAAGCCAT GCTTATT          117

(2) INFORMATION FOR SEQ ID NO: 9:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 9:

```
AGCCTTTTTA ATAGAATGGC AAGACAAAGA ATAGCTATTA CAAGTGATAT TTCAGGTACA        60

ACTAGAGATA CAAATAAAAC AGAAATTCAT ATTAATTCAA AAAAAGCCAT GCTTATT         117
```

(2) INFORMATION FOR SEQ ID NO: 10:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
AGTCTTTTTA ATAGAATGGC AAGACAAAGA ATAGCTATTA CAAGTGATAT TTNAGGTACA        60

ACTAGAGATA CAAATAAAAC AGAAAT                                            86
```

(2) INFORMATION FOR SEQ ID NO: 11:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
AGTTTATTTA ACAGAATGGC AAGGCAAAGA ATAGCTATTA CAAGTGAAAT TNNAGGTACT        60

ACAAGAGATA CNAATAAAAC AGAAGT                                            86
```

(2) INFORMATION FOR SEQ ID NO: 12:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
AGTTTATTTA ACAGAATGGC AAGGCAAAGA AGAGCTATTA CAAGTGAAAT TTCAGGTACT        60

ACAAGAGATA CCAATAAAAC AGAAGTTTTT ATAAATTCTA AAAAAGCCCT ATTGATT         117
```

(2) INFORMATION FOR SEQ ID NO: 13:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
AGTTTATTTA ACAGAATGGC AAGGCAAAGA ATAGCTATTA CAAGTGAAAT TTCAGGTACT        60

ACAAGAGATA CCAATAAAAC AGAAGTTTTT ATAAATTCTA AAAAAGCCCT ATTGATT         117
```

(2) INFORMATION FOR SEQ ID NO: 14:

(i) SEQUENCE CHARACTERISTICS:
        (A) LENGTH: 117 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 14:

```
AGTTTATTTA ACAGAATGGC AAGGCAAAGA ATAGCTATTA CAAGTGAAAT TTCAGGTACT    60

ACAAGAGATA CCAATAAAAC AGAAGTTTTT ATAAATTCGA AAAAGCCCT ATTGATC       117
```

(2) INFORMATION FOR SEQ ID NO: 15:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
AGTTTATTTA ACAGAACGGC AAGGCAAAGA ATAGCTATTA CAAGTGAAAT TTCAGGTACT    60

ACAAGAGATA CCAATAAAAC AGAAGTTTTT ATAAATTCTA AAAAGCCCT ATTGATT       117
```

(2) INFORMATION FOR SEQ ID NO: 16:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
AGTTNNTTTA ACAGAATGGC AAGGCAAAGA ATAGCTATTA CAAGTGAAAT TNNAGGTACT    60

ACAAGAGATA CNAATAAAAC AGAAGT                                        86
```

(2) INFORMATION FOR SEQ ID NO: 17:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
AGTCTTTTTA ATAGACTTGC AAGAAAGCGC ATAGCTATNA CNAGTGACAT NNGTGGAACN    60

ACAAGAGATA CNAATAAAAT AGAAGTT                                       87
```

(2) INFORMATION FOR SEQ ID NO: 18:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
AGTCTTTTTA ATAGACTTGC AAGAAAGCGC ATAGCTATNA CNAGTGACAT AAGTGGAACN    60

ACAAGAGATA CNAATAAAAT AGAAGTA                                       87
```

(2) INFORMATION FOR SEQ ID NO: 19:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

AGTCTTTTTA ATAGACTTGC AAGAAAGCGC ATAGCTATCA CCAGTGACAT AAGTGGAACC    60

ACAAGAGATA CCAATAAAAT AGAAGTACAA ATTGATGGCA AAAAGCCTT GCTTATA      117

(2) INFORMATION FOR SEQ ID NO: 20:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

AGTCTTTTTA ATAGACTTGC AAGAAAGCGC ATAGCTATCA CCAGTGACAT AAGTGGAACC    60

ACAAGAGATA CCAATAAAAT AGAAGTACAA ATTSATGGCA AAAAGCCTT GCTTATA      117

(2) INFORMATION FOR SEQ ID NO: 21:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

AGTCTTTTTA ATAGACTTGC AAGAAAGCGC ATAGCTATNA CNAGTGACAT AAGTGGAACN    60

ACAAGAGATA CNAATAAAAT AGAAGT                                         86

(2) INFORMATION FOR SEQ ID NO: 22:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

AGCCTTTTTA ATCGCATAGC AAGGCAAAGA ATCGCCATCA CAAGTGAAAT TTCAGGCACG    60

ACTAGAGATA CAAATAAAAT AAAAGTTAAT ATCAATGGTA AGAAGCCTT GCTTATC      117

(2) INFORMATION FOR SEQ ID NO: 23:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

AGCCTTTTTA AACGCATAGC AAGGCAAAGA ATCGCCATCA CAAGTGAAAT TTCAGGCACG        60

ACTAGAGATA CAAATAAAAT AAAAGTTAAT ATCAATGGTA AGAAGCCTT GCTTATT          117

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

CCAAATGTTG GAAAATCA                                                    18

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 13
        (D) OTHER INFORMATION: /mod_base= i (xi) SEQUENCE DESCRIPTION: SEQ ID NO: 25:

GCCAAATGTT GGNAARTC                                                    18

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO: 26:

AANCCAAATG TTGGNAAR                                                    18

(2) INFORMATION FOR SEQ ID NO: 27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6

(D) OTHER INFORMATION: /mod_base= i (ix) FEATURE:
            (A) NAME/KEY: modified_base
            (B) LOCATION: 15
            (D) OTHER INFORMATION: /mod_base= i (xi) SEQUENCE DESCRIPTION: SEQ ID NO: 27:

GGCAANCCAA ATGTNGG                                                     17

(2) INFORMATION FOR SEQ ID NO: 28:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 28:

ATGTTGGAAA ATCAAGYC                                                    18

(2) INFORMATION FOR SEQ ID NO: 29:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 29:

ATCAAGTTTA TTTAAC                                                      16

(2) INFORMATION FOR SEQ ID NO: 30:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 30:

TAGACTTCGA AGAAAGCGC                                                   19

(2) INFORMATION FOR SEQ ID NO: 31:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 31:

CATAGCAAGG CAAAGAATCG CC                                               22

(2) INFORMATION FOR SEQ ID NO: 32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 32:

GATAGTGGAG GGCTTGAT                                                                18

(2) INFORMATION FOR SEQ ID NO: 33:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: modified_base
                (B) LOCATION: 6
                (D) OTHER INFORMATION: /mod_base= i (xi) SEQUENCE DESCRIPTION: SEQ ID NO: 33:

GAYAGNGGAG GGCTTGAT                                                                18

(2) INFORMATION FOR SEQ ID NO: 34:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: modified_base
                (B) LOCATION: 6
                (D) OTHER INFORMATION: /mod_base= i (ix) FEATURE:
                (A) NAME/KEY: modified_base
                (B) LOCATION: 12
                (D) OTHER INFORMATION: /mod_base= i (ix) FEATURE:
                (A) NAME/KEY: modified_base
                (B) LOCATION: 15
                (D) OTHER INFORMATION: /mod_base= i (xi) SEQUENCE DESCRIPTION: SEQ ID NO: 34:

GAYAGNSSAG GNCTNGAT                                                                18

(2) INFORMATION FOR SEQ ID NO: 35:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 35:

GGGCTTGATG AAAGTGAT                                                                18

(2) INFORMATION FOR SEQ ID NO: 36:

(i) SEQUENCE CHARACTERISTICS:
                (A) LENGTH: 24 base pairs
                (B) TYPE: nucleic acid
                (C) STRANDEDNESS: single (D) TOPOLOGY: linear (ii) MOLECULE TYPE: DNA (genomic)

(xi) SEQUENCE DESCRIPTION: SEQ ID NO: 36:

GGCTTTTTTT GAATGAATAT GAAT                                              24

(2) INFORMATION FOR SEQ ID NO: 37:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 37:

CCCTCCACTA TCAATAATAG                                                   20

(2) INFORMATION FOR SEQ ID NO: 38:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 38:

GCCATCAATT TGTACTTCTA                                                   20

(2) INFORMATION FOR SEQ ID NO: 39:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 39:

TTAAAAGCTC AGGCTTC                                                      17

(2) INFORMATION FOR SEQ ID NO: 40:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 40:

ACWAGAGATA CMAATAAAA                                                    19

(2) INFORMATION FOR SEQ ID NO: 41:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 41:

CAGGTACAAC TAGAGATACA                                        20

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

TTAATAGAAT GGCAAGACAA                                        20

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

TAGAATGGCA AGACAAAGAA                                        20

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

ATATTTCAGG YACAACTAGA                                        20

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

ATTCAAAAAA AGCCATGCTT                                        20

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

TCAAGTTTAT TTAACAGAAT                                        20

(2) INFORMATION FOR SEQ ID NO: 47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

AAATTTCAGG TACTACAAGA                                      20

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

TAAAACAGAA GTTTTTATAA                                      20

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

CTTTTTAATA GACTTGCAAG                                      20

(2) INFORMATION FOR SEQ ID NO: 50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

GACTTGCAAG AAAGCGCATA                                      20

(2) INFORMATION FOR SEQ ID NO: 51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

ACATAAGTGG AACCACAAGA                                      20

(2) INFORMATION FOR SEQ ID NO: 52:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 52:

TCACCAGTGA CATAAGTGGA                                               20

(2) INFORMATION FOR SEQ ID NO: 53:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 53:

TGGAACCACA AGAGATACCA                                               20

(2) INFORMATION FOR SEQ ID NO: 54:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 54:

TGATGGCAAA AAAGCCTTGC                                               20

(2) INFORMATION FOR SEQ ID NO: 55:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 55:

GCATAGCTAT CACCAGTGAC                                               20

(2) INFORMATION FOR SEQ ID NO: 56:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 56:

CAATAAAATA GAAGTACAAA                                               20

(2) INFORMATION FOR SEQ ID NO: 57:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 57:

CGCATAGCAA GGCAAAGAAT                                                           20

(2) INFORMATION FOR SEQ ID NO: 58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

TTTCAGGCAC GACTAGAGAT                                                           20

(2) INFORMATION FOR SEQ ID NO: 59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

CAATGGTAAA GAAGCCTTGC                                                           20

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

AAGAATCGCC ATCACAAGTG                                                           20

(2) INFORMATION FOR SEQ ID NO: 61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

TTTTTAATAG AATGGCAAGA C                                                         21

(2) INFORMATION FOR SEQ ID NO: 62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

```
CTTTTTAATA GAATGGCAAG ACAAAG                                          26

(2) INFORMATION FOR SEQ ID NO: 63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

CATTCAAAAA AAGCCATGCT T                                               21

(2) INFORMATION FOR SEQ ID NO: 64:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

TTCATATTCA TTCAAAAAAA GCCATGCTT                                       29

(2) INFORMATION FOR SEQ ID NO: 65:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

ATCAAGTTTA TTTAACAGAA TGG                                             23

(2) INFORMATION FOR SEQ ID NO: 66:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

ATCAAGTTTA TTTAACAGAA TGGCAAG                                         27

(2) INFORMATION FOR SEQ ID NO: 67:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 67:

CAATAAAACA GAAGTTTTTA TAA                                             23
```

(2) INFORMATION FOR SEQ ID NO: 68:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

CCAATAAAAC AGAAGTTTTT ATAAATTC                                28

(2) INFORMATION FOR SEQ ID NO: 69:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

TAATCGCATA GCAAGGCAA                                         19

(2) INFORMATION FOR SEQ ID NO: 70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

TATCAATGGT AAAGAAGCCT T                                      21

(2) INFORMATION FOR SEQ ID NO: 71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

TTTTAATGCG TTAACAAAAC                                        20

(2) INFORMATION FOR SEQ ID NO: 72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

CTAGCAATGC AGAATCTGCA                                        20

(2) INFORMATION FOR SEQ ID NO: 73:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

CTATCCATTT TGCACTATAG                                              20

(2) INFORMATION FOR SEQ ID NO: 74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 74:

ATAGTTCCGG TTCCAGATAT                                              20

(2) INFORMATION FOR SEQ ID NO: 75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 75:

TCCAGATATA CGCTTAAATG                                              20

(2) INFORMATION FOR SEQ ID NO: 76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 76:

TTTTAATGCT CTAACAAAAC                                              20

(2) INFORMATION FOR SEQ ID NO: 77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

CTAGTAACGC AGAGGCNGCA                                              20

(2) INFORMATION FOR SEQ ID NO: 78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 78:

CTATCNGTTT TGTACTATNG                                               20

(2) INFORMATION FOR SEQ ID NO: 79:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 79:

TNNTGATGCG CGTTTGAATG                                               20

(2) INFORMATION FOR SEQ ID NO: 80:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 80:

AATAAAGTAG ATAATAAAAA A                                             21

(2) INFORMATION FOR SEQ ID NO: 81:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: modified_base
            (B) LOCATION: 9
            (D) OTHER INFORMATION: /mod_base= i (ix) FEATURE:
            (A) NAME/KEY: modified_base
            (B) LOCATION: 12
            (D) OTHER INFORMATION: /mod_base= i (xi) SEQUENCE DESCRIPTION: SEQ ID NO: 81:

AAYAARGTNG RNAAYAAAAA A                                             21

(2) INFORMATION FOR SEQ ID NO: 82:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 82:

AGTCTTTTAA ATGCTTTGGT TAAACAAGAA CGCAGTGTTG TAAGTTCTAT CGCAGGAACT     60

ACTATAGATC CTGTTAATGA AAGTGTAGTT CATAAAGATA AAGTGATAGA ATTTGTT       117

(2) INFORMATION FOR SEQ ID NO: 83:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..168

(ix) FEATURE:
        (A) NAME/KEY: mat_peptide
        (B) LOCATION: 2..168

(xi) SEQUENCE DESCRIPTION: SEQ ID NO: 83:

```
AACGACTTTT AATGCGTTAA CAAAAGCTAG CAATGCAGAA TCTGCAAACT ATCCATTTTG      60

CACTATAGAG CCAAATAAAG CCATAGTTCC GGNTCCAGAT ATACGCTTAA ATGAGCTWRC     120

AAAAATAGTA AATCCAAATA AAATCCAACA TTCGACTATC GAATTTGTA               169
```

(2) INFORMATION FOR SEQ ID NO: 84:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 84:

```
Thr Thr Phe Asn Ala Leu Thr Lys Ala Ser Asn Ala Glu Ser Ala Asn
1               5                  10                  15

Tyr Pro Phe Cys Thr Ile Glu Pro Asn Lys Ala Ile Val Pro Xaa Pro
                20                  25                  30

Asp Ile Arg Leu Asn Glu Xaa Xaa Lys Ile Val Asn Pro Asn Lys Ile
            35                  40                  45

Gln His Ser Thr Ile Glu Phe Val
    50                  55
```

(2) INFORMATION FOR SEQ ID NO: 85:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..169

(ix) FEATURE:
        (A) NAME/KEY: mat_peptide
        (B) LOCATION: 2..169

(xi) SEQUENCE DESCRIPTION: SEQ ID NO: 85:

```
AACCACATTT AACGCGCTAA CGAAGGCGCA AAACGCCGAG AGCGCGAACT ATCCGTTYTG      60

CACGATCGAG CCRAATAAAG CCGTCGTGCC GGTGCCCGAT AAGCKCCTAG GCNTGCTARC     120

CAAAATCGTA AATCCAAATA AAATCCAATA CTCCACTATC GAATTCGTC                169
```

(2) INFORMATION FOR SEQ ID NO: 86:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 86:

Thr Thr Phe Asn Ala Leu Thr Lys Ala Gln Asn Ala Glu Ser Ala Asn
1               5                   10                  15

Tyr Pro Xaa Cys Thr Ile Glu Xaa Asn Lys Ala Val Val Pro Val Pro
            20                  25                  30

Asp Lys Xaa Leu Gly Xaa Leu Xaa Lys Ile Val Asn Pro Asn Lys Ile
        35                  40                  45

Gln Tyr Ser Thr Ile Glu Phe Val
50                  55

(2) INFORMATION FOR SEQ ID NO: 87:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..125

(ix) FEATURE:
        (A) NAME/KEY: mat_peptide
        (B) LOCATION: 2..125

(xi) SEQUENCE DESCRIPTION: SEQ ID NO: 87:

AACGACTTTT AATGCTCTAA CAAAAGCTAG TAACGCAGAG GCNGCAAACT ATCNGTTTTG      60

TACTATNGAG CCAAATAAAG CTATAGTTNN TGTTNNTGAT GCGCGTTTGA ATGAGCTTTC     120

AAAAA                                                                125

(2) INFORMATION FOR SEQ ID NO: 88:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO: 88:

Thr Thr Phe Asn Ala Leu Thr Lys Ala Ser Asn Ala Glu Xaa Ala Asn
1               5                   10                  15

Tyr Xaa Phe Cys Thr Xaa Glu Pro Asn Lys Ala Ile Val Xaa Val Xaa
            20                  25                  30

Asp Ala Arg Leu Asn Glu Leu Ser Lys
        35                  40

(2) INFORMATION FOR SEQ ID NO: 89:

(i) SEQUENCE CHARACTERISTICS:
        (A) LENGTH: 165 base pairs
        (B) TYPE: nucleic acid
        (C) STRANDEDNESS: single
        (D) TOPOLOGY: linear

```
    (ii) MOLECULE TYPE: DNA (genomic)

(ix) FEATURE:
         (A) NAME/KEY: CDS
         (B) LOCATION: 2..165

(ix) FEATURE:
         (A) NAME/KEY: mat_peptide
         (B) LOCATION: 2..165

(xi) SEQUENCE DESCRIPTION: SEQ ID NO: 89:

TACCCTTTTC AATGCATTAA CGAAAGCAGC GATTGCAGCG GAAAACTTCC CTTTCTGTAC      60

CATTGAACCA AACACAGGTA TTGTTCCTGT ACCAGATCCA CGTTTAGACA AACTTGCTGC     120

GATTGTTAAA CCACAGCGTA TTTTGCCAAC CACAATGGAA TTTGT                    165

(2) INFORMATION FOR SEQ ID NO: 90:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO: 90:

Thr Leu Phe Asn Ala Leu Thr Lys Ala Ala Ile Ala Ala Glu Asn Phe
  1               5                  10                  15

Pro Phe Cys Thr Ile Glu Pro Asn Thr Gly Ile Val Pro Val Pro Asp
              20                  25                  30

Pro Arg Leu Asp Lys Leu Ala Ala Ile Val Lys Pro Gln Arg Ile Leu
          35                  40                  45

Pro Thr Thr Met Glu Phe
     50

(2) INFORMATION FOR SEQ ID NO: 91:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 2..165

(ix) FEATURE:
         (A) NAME/KEY: mat_peptide
         (B) LOCATION: 2..165

(xi) SEQUENCE DESCRIPTION: SEQ ID NO: 91:

TACCCTTTTC AATGCATTAA CGAAAGCAGC GATTGCAGCG GAAAACTTCC CTTTCTGTAC      60

CATTGAACCA AACACAGGTA TTGTTCCTGT ACCAGATCCA CGTTTAGACA AACTTGCTGC     120

GATTGTTAAA CCACAGCGTA TTTTGCCAAC WACAATGGAA TTTGT                    165

(2) INFORMATION FOR SEQ ID NO: 92:

(i) SEQUENCE CHARACTERISTICS:
        (A) LENGTH: 54 amino acids
        (B) TYPE: amino acid
        (D) TOPOLOGY: linear (ii) MOLECULE TYPE: protein
```

(xi) SEQUENCE DESCRIPTION: SEQ ID NO: 92:

Thr Leu Phe Asn Ala Leu Thr Lys Ala Ala Ile Ala Ala Glu Asn Phe
1               5                   10                  15

Pro Phe Cys Thr Ile Glu Pro Asn Thr Gly Ile Val Pro Val Pro Asp
            20                  25                  30

Pro Arg Leu Asp Lys Leu Ala Ala Ile Val Lys Pro Gln Arg Ile Leu
        35                  40                  45

Pro Xaa Thr Met Glu Phe
    50

(2) INFORMATION FOR SEQ ID NO: 93:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..166

(ix) FEATURE:
        (A) NAME/KEY: mat_peptide
        (B) LOCATION: 2..166

(xi) SEQUENCE DESCRIPTION: SEQ ID NO: 93:

TACCCTTTTC AATGCATTAA CGAAAGCAGC GATTGCAGCG GAAAACTTCC CTTTCTGTAC      60

CATTGAACCA AACACAGGTA TTGTTCCTGT ACCAGATCCA CGTTTAGACA AACTTGCTGC     120

GATTGTTAAA CCACAGCGTA TTTTGCCAAC ATACAATGGA ATTTGT                    166

(2) INFORMATION FOR SEQ ID NO: 94:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO: 94:

Thr Leu Phe Asn Ala Leu Thr Lys Ala Ala Ile Ala Ala Glu Asn Phe
1               5                   10                  15

Pro Phe Cys Thr Ile Glu Pro Asn Thr Gly Ile Val Pro Val Pro Asp
            20                  25                  30

Pro Arg Leu Asp Lys Leu Ala Ala Ile Val Lys Pro Gln Arg Ile Leu
        35                  40                  45

Pro Thr Tyr Asn Gly Ile Cys
    50                  55

(2) INFORMATION FOR SEQ ID NO: 95:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..165

-continued

```
    (ix) FEATURE:
          (A) NAME/KEY: mat_peptide
          (B) LOCATION: 2..165

(xi) SEQUENCE DESCRIPTION: SEQ ID NO: 95:

TACACTTTTC AATGCCTTAA CCAAAGCTGC TATTGCTGCA GAAAACTTCC CTTTCTGTAC      60

GATCGAACCA AACACCGGGA TTGTACCTGT TCCTGATCCA CGTTTAGACA AATTGACCGC     120

AATTGTTAAA CCGCAACGTG TTATTCCGAC TTCTATGGAA TTTGT                    165

(2) INFORMATION FOR SEQ ID NO: 96:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO: 96:

Thr Leu Phe Asn Ala Leu Thr Lys Ala Ala Ile Ala Ala Glu Asn Phe
1                 5                  10                  15

Pro Phe Cys Thr Ile Glu Pro Asn Thr Gly Ile Val Pro Val Pro Asp
             20                  25                  30

Pro Arg Leu Asp Lys Leu Thr Ala Ile Val Lys Pro Gln Arg Val Ile
         35                  40                  45

Pro Thr Ser Met Glu Phe
         50
```